United States Patent
Tawara et al.

(10) Patent No.: US 8,492,119 B2
(45) Date of Patent: Jul. 23, 2013

(54) ANTIBODY TO HUMAN IL-3 RECEPTOR ALPHA CHAIN

(75) Inventors: Tomonori Tawara, Machida (JP); Shinichiro Takayanagi, Machida (JP); Yoshimasa Inagaki, Machida (JP)

(73) Assignee: Kyowa Hakko Kirin Co., Ltd, Tokyo (JP)

( * ) Notice: Subject to any disclaimer, the term of this patent is extended or adjusted under 35 U.S.C. 154(b) by 0 days.

(21) Appl. No.: 13/266,603

(22) PCT Filed: Apr. 27, 2010

(86) PCT No.: PCT/JP2010/057510
§ 371 (c)(1),
(2), (4) Date: Dec. 1, 2011

(87) PCT Pub. No.: WO2010/126066
PCT Pub. Date: Nov. 4, 2010

(65) Prior Publication Data
US 2012/0070448 A1    Mar. 22, 2012

Related U.S. Application Data

(60) Provisional application No. 61/172,923, filed on Apr. 27, 2009.

(51) Int. Cl.
*C07K 16/28* (2006.01)
*A61K 39/395* (2006.01)
*C12N 15/63* (2006.01)

(52) U.S. Cl.
USPC ................. 435/69.6; 424/143.1; 530/388.22

(58) Field of Classification Search
None
See application file for complete search history.

(56) References Cited

U.S. PATENT DOCUMENTS

| | | | |
|---|---|---|---|
| 5,639,605 | A | 6/1997 | Kitamura et al. |
| 6,177,078 | B1 | 1/2001 | Lopez |
| 6,733,743 | B2 | 5/2004 | Jordan |
| 2009/0252742 | A1 | 10/2009 | Bergstein |
| 2011/0052574 | A1 | 3/2011 | Dick et al. |

FOREIGN PATENT DOCUMENTS

| | | |
|---|---|---|
| WO | 97/24373 A1 | 7/1997 |
| WO | 01/66139 A1 | 9/2001 |
| WO | 2009070844 A1 | 6/2009 |
| WO | 2011038467 A1 | 4/2011 |
| WO | 2012021934 A1 | 2/2012 |

OTHER PUBLICATIONS

Lederman et al (1991), Molecular Immunology, vol. 28, No. 11, pp. 1171-1181.*
Li et al. (2004), International Immunology, vol. 4, pp. 693-708.*
Panka et al. Proc. Natl. Acad. Sci. USA vol. 85, pp. 3080-3084 (May 1988).*
Rudikoff et al. Proc. Natl. Acad. Sci. USA vol. 79, pp. 1979-1983 (Mar. 1982).*
Amit et al. Science, Vot. 233, pp. 747-753, (Aug. 1986).*
Roberts, Andrew W. et al. "A Phase 1 and Correlative Biological Study of CSL360 (anti-CD123 mAb) in AML", vol. 112, No. 11, Nov. 2008, pp. 1015-1016, XP009161393.
European Patent Office, Communication issued Aug. 7, 2012 in counterpart European Application No. 10769764.1.
Jin et al. "Monoclonal Antibody-Mediated Targeting of CD123, IL-3 Receptor a Chain, Eliminates Human Acute Myeloid Leukemic Stem Cells," Cell Stem Cell, vol. 5, pp. 31-42, Jul. 2, 2009.
Barry et al. "Roles of the N and C terminal domains of the interleukin-3 receptor a chain in receptor function," Blood, Feb. 1, 2007, vol. 89, No. 3, pp. 842-852.
Chen et al. "A new isoform of interleukin-3 receptor a with novel differentiation activity and high affinity binding mode," J. Biol. Chem., Feb. 27, 2009, vol. 284, No. 9, pp. 5763-5773.
Jordan et al. "The interleukin-3 receptor alpha chain is a unique marker for human acute myelogenous leukemia stem cells," Leukemia, Oct. 2000, vol. 14, pp. 1777-1784.
Munoz et al., "Interleukin-3 receptor a chain (CD123) is widely expressed in hematologic malignancies," Haematologica, Dec. 2001, vol. 86, No. 12, pp. 1261-1269.
Sun et al., Monoclonal antibody 7G3 recognizes the N-terminal domain of the human interleukin-3 (IL-3) receptor alpha-chain and functions as a specific IL-3 receptor antagonist, Blood, Jan. 1996, vol. 87, No. 1, pp. 83-92.
Du et al., "New Immunotoxins Targeting CD123, a Stem Cell Antigen on Acute Myeloid Leukemia Cells," J. Immunother., Sep. 2007, vol. 30, No. 6, pp. 607-613.
Shitara et al., "Potelligent Antibodies as Next Generation Therapeutic Antibodies,"Yakugaku Zasshi, Jan. 2009, vol. 129, No. 1, pp. 3-9.

* cited by examiner

*Primary Examiner* — Prema Mertz
(74) *Attorney, Agent, or Firm* — Sughrue Mion, PLLC

(57) ABSTRACT

The present invention provides an antibody to human IL-3Rα chain, which does not inhibit IL-3 signaling and binds to B domain of the human IL-3Rα chain but does not bind to C domain of the human IL-3Rα chain; a composition for preventing or treating a blood tumor in which a cell expressing IL-3Rα is found in bone marrow or peripheral blood of a subject, which comprises the antibody to human IL-3Rα as an active ingredient; and a method for treating a blood tumor in which a cell expressing IL-3Rα is found in bone marrow or peripheral blood, which comprises administering, to a subject, a composition comprising the IL-3Rα antibody as an active ingredient.

7 Claims, 10 Drawing Sheets

Fig. 4

```
                    10        20        30        40        50
                    |         |         |         |         |
            ATGGTCCTCCTTTGGCTCACGCTGCTCCTGATCGCCCTGCCCTGTCTCCTGCAAACGAAG    60
             M  V  L  L  W  L  T  L  L  L  I  A  L  P  C  L  L  Q  T  K    20
            GAAGATCCAAACCCACCAATCACGAACCTAAGGATGAAAGCAAAGGCTCAGCAGTTGACC   120   Region
             E  D  P  N  P  P  I  T  N  L  R  M  K  A  K  A  Q  Q  L  T    40      1
            TGGGACCTTAACAGAAATGTGACCGATATCGAGTGTGTTAAAGATGCCGACTATTCTATG   180
Region       W  D  L  N  R  N  V  T  D  I  E  C  V  K  D  A  D  Y  S  M    60
  2         CCGGCATGAACAATAGCTATTGCCAGTTGGAGCAATTTCCTTATGTGAAGTGACCAAC    240   Region
             P  A  Y  N  N  S  Y  C  Q  F  G  A  I  S  L  C  E  V  T  N           3
            TACACCGTCCGAGTGGCCAACCCACCATTCTCCACGTGGATCCTCTTCCCTGAAAACAGT   300
             Y  T  V  R  V  A  N  P  P  F  S  T  W  I  L  F  P  E  N  S   100
            GGGAAGCCTTGGGCAGGTGCGGAGAATCTGACCTGCTGGATTCATGACGTGGATTTCTTG           Region
             G  K  P  W  A  G  A  E  N  L  T  C  W  I  H  D  V  D  F  L   120      4
Region      AGCTGCAGCTGGGCGGTAGGCCCCGGGGCCCCCGCGGACGTCCAGTACGACCTGTACTTG   420
  5          S  C  S  W  A  V  G  P  G  A  P  A  D  V  Q  Y  D  L  Y  L   140
            AACGTTGCCAACAGGCGTCAACAGTACGAGTGTCTTCACTACAAAACGGATGCTCAGGGA   480
             N  V  A  N  R  R  Q  Q  Y  E  C  L  H  Y  K  T  D  A  Q  G   160
            ACACGTATCGGGTGTCGTTTCGATGACATCTCTCGACTCTCCAGCGGTTCTCAAAGTTCC   540
Region       T  R  I  G  C  R  F  D  D  I  S  R  L  S  S  G  S  Q  S  S   180
  6         CAGATCCTGGTGCGGGGCAGGAGCGCAGCCTTGGGTATCCCCTGCACAGATAAGTTTGTC   600
             H  I  L  V  R  G  R  S  A  A  F  G  I  P  C  T  D  K  F  V   200
            GTCTTTTCA
             V  F  S                         Region
                                               7
```

ANTIBODY TO HUMAN IL-3 RECEPTOR ALPHA CHAIN

TECHNICAL FIELD

This invention relates to an antibody to human IL-3Rα protein (another name: human CD123). The invention also relates to an invention of a therapeutic agent and diagnostic agent for myelocytic malignant tumors, particularly acute myeloid leukemia (AML), which comprises a human IL-3Rα antibody as an active ingredient.

BACKGROUND OF THE INVENTION

Regarding Malignant Tumor:

A malignant tumor (cancer) is the first leading cause of death in Japan and the number of patients is increasing every year, and the development of a drug and a therapeutic method having high efficacy and safety is strongly desired. As the cause of forming a malignant tumor, there is a mutation of DNA by radiation, ultraviolet rays and various carcinogenic substances. Studies on malignant tumors have been focused on molecular biological identification of these genetic changes. As a result, it is considered that tumorigenic transformation is induced by accumulation of a large number of mutations and the like. It has been shown by a cell line model and the like that some decisive mutations directly connected with the tumorigenic transformation. Regarding leukemia as one of the objective diseases of the invention, many chromosomal abnormalities have been identified and classified. In many of the case, translocation of chromosome is found and the some genes associated with chromosomal translocation have already been identified in principle chromosomal translocations. By analyses of functions of the translocation related genes, a case has been found that these genes are concerned in the onset of leukemia.

Regarding Cancer Stem Cell:

On the other hand, a so-called cancer stem cell hypothesis has been proposed for a long time from the viewpoint of cell biology, stating that stem cell is the origin of a malignant tumor similar to the normal tissue. The stem cell is defined as a cell having autonomous replication ability and pluripotency and generally divided roughly into totipotency stem cell and tissue stem cell. Tissue stem cells are originated from specific tissues and organs such as of blood system, liver, nerve system and the like and present at an extremely low frequency. Among them, hematopoietic stem cell has been studied most frequently. It has been reported that a hematopoietic system can be reconstructed over a long period of time by transplanting one hematopoietic stem cell into a mouse in which the hematopoietic system was destructed by a lethal dose of irradiation (Non-patent Document 1). Different from the normal stem cell, studies on cancer stem cells have been delayed for a prolonged period of time since their true nature could not been found. However, a cancer stem cell has been identified for the first time in acute myeloid leukemia, in 1997 by Dick et al. Thereafter, the presence of cancer stem cells has been reported in various malignant tumors. In summing up, cancer stem cells are present at a frequency of several % or less of the whole tumor and rare as well as normal stem cells. It is considered that the remaining cells which form the tumor are tumor precursor cells in which proliferation ability is limited or tumor cells.

By these reports, it was shown that hierarchy is present even in tumor similar to the normal tissue, and the cancer stem cell residing at this peak (origin) has strong tumor forming ability.

Characteristics and Therapeutic Problems of Cancer Stem Cells:

In summing up many reports, it is considered that cancer stem cells are maintaining various characteristics possessed by the normal stem cells. Examples of similarities include the rarity of the cells, a microenvironment (niche) in which the cell exists, expression of a multiple drug resistance gene, cell cycle arrest, and the like.

Particularly, the characteristics that they express a group of multiple drug resistance genes and are at the interphase of cell cycle similar to the normal stem cells could become a therapeutically great problem. A multiple drug resistance gene BCRP is a pump which impairs the drug efficacy by eliminating various antitumor agents into outside of cells, and a method for collecting stem cells making use of the activity has been reported (Non-patent Document 2). In addition, their presence at the interphase of cell cycle under a state of "arresting" (Non-patent Document 3) is causing reduction of sensitivity for many antitumor agents and radiations which targets the quick cell growth of cancer (Non-patent Documents 4 and 5).

Based on the above characteristics, it is considered that the cancer stem cell which exhibiting resistance to the therapy is a cause of tumor regeneration.

Regarding molecular target drug

Three main courses of the treatment of a malignant tumor include of antitumor agent therapy, radiation therapy and surgical excision. The blood tumor is limited to the antitumor agent therapy and radiation therapy, and as described in the above, the cancer stem cell can have a resistance to these treatments. Another problem is that side effects are large since these two treatments affect the entire body. It is a molecular target drug that is expected as a resolving means for this problem. It has a possibility to reduce side effects by exhibiting its drug efficacy only in the cell expressing the target molecule.

Examples of typical drugs of the molecular target drug in the field of blood diseases include imatinib and rituximab. Imatinib targets at a leukemia-causing factor called Bcr-Abl produced by a chromosomal abnormality (Philadelphia chromosome) which is observed in 95% of CML patients. This is a low molecular weight drug which induces suicide of leukemia cell by inhibiting function of Bcr-Abl. Rituximab is a therapeutic antibody which recognizes CD20 as a surface molecule on a B cell and has an antitumor effect on a malignant tumor of B cell (non-Hodgkin lymphoma and the like). On the other hand, molecular target drugs for AML are few, and there is only an agent gemtuzumab•ozogamicin (Mylotarg) in which an antibiotic calicheamicin is linked to a monoclonal antibody for CD33 known as an AML cell surface antigen. However, it is the present situation that the use of Mylotarg is limited because of its strong toxicity which is considered to be derived from calicheamicin in addition to the problem that therapeutic range is narrow. Based on the above, it can be said that discovery of a new target gene and development of a therapeutic agent for this are important inventions which directly lead to the possibility of therapy and expansion of the choices of therapy.

As the embodiment of molecular target drugs, various substances have been studied and developed such as a therapeutic antibody and a low molecular weight drug, as well as a peptide drug, a biological protein preparation such as cytokine, an siRNA, aptamer and the like. When an antibody is used as a therapeutic agent, due to its specificity, it is useful in treating pathological conditions in which the disordered cell expresses a specific antigen. The antibody binds to a protein expressing on the cell surface as its antigen and effectively acts upon the bound cell. The antibody has a characteristic of long blood half life and high specificity for its antigen and is also markedly useful as an antitumor agent. For example, when an antibody targets at a tumor-specific antigen, it can be expected that the administered antibody accumulates into the tumor and thereby attacks the tumor cell via complement-dependent cytotoxicity (CDC) and antibody-dependent cellular cytotoxicity (ADCC). In addition, by binding a radioactive substance, a cytotoxic substance and the like to an antibody, it becomes possible to transfer an agent efficiently to the tumor part and thereby to allow to act thereon. At the same time, it can decrease the amount of the reached agent to non-specific other tissues and reduction of side effects can also be expected Inhibition of tumor growth or regression of tumor can be expected by administering an antibody having agonistic activity when a tumor-specific antigen has an activity to induce cell death, or by administering an antibody having neutralization activity when a tumor-specific antigen relates to in the growth and survival of cells. Due to the above characteristics, it is considered that antibodies are suited in applying as antitumor agents.

Regarding therapeutic antibodies:

In the original antibody preparation, a mouse was used as the animal to be immunized. However, use of mouse antibodies as drugs is limited due to a large number of reasons. A mouse antibody which can be recognized as a foreign substances in the human body can induce so-called "human anti-mouse antibody" namely "HAMA" response (Non-patent Document 6). Further, the Fc region of mouse antibody is not effective for the attack on disease cells via human complement or human immune cells.

As one of the approaches for avoiding such problems, a chimeric antibody has been developed (Patent Documents 1 and 2). The chimeric antibody contains parts of antibodies derived from two or more species (mouse antibody variable region, human antibody constant region and the like). An advantageous point of such a chimeric antibody is that it keeps the characteristics of mouse antibody but can activate human complement or human immune cells since it has human Fc. However, it is known that such a chimeric antibody still induces "human anti-chimeric antibody" namely "HACA" response (Non-patent Document 7).

Further, it has been developed a recombinant antibody in which only a complementarity determining regions ("CDRs") of a part of an antibody were substituted (Patent Documents 3 and 4). By the use of a CDR grafting technique, an antibody comprising mouse CDR and human variable region framework and human constant region, so-called "humanized antibody" (Non-patent Document 8). Further, by the use of a human antibody producing mouse or by a screening using a human antibody library, broadly utilized techniques have been provided also regarding preparation of complete human antibodies (Non-patent Documents 9 and 10).

Regarding IL-3Rα:

IL-3Rα is the α chain of IL-3 receptor, belongs to a cytokine receptor family and shows weak affinity for IL-3 as its ligand. By forming a hetero receptor with its β chain (CD131, hereinafter also referred to as IL-3Rβ), an IL-3 receptor has a strong binding and transfers a signal such as growth, differentiation and the like into a cell through intracellular region of the β chain. IL-5 receptor α chain and GM-C SF receptor α chain share the β chain in common.

IL-3Rα is a type I membrane protein of single-pass transmembrane, and it is known based on the sequence that an IL-3 binding site and a fibronectin type III site are present in the extramembrane region. It is known that there is no structure which can transfer a signal in the intramembrane region. Though three-dimensional structure of IL-3Rα has not been analyzed yet, it can be assumed that structures of cytokine receptors are similar between families since position of cysteine residue which forms the structurally important S—S bond is preserved in most cases. Among the same cytokine receptors, crystalline structures of IL-13 receptor α chain, IL-4 receptor α chain and GM-CSF receptor a chain have been analyzed. Based on the information of these cytokine receptor families, it can be assumed that the extramembrane region of IL-3Rα is roughly divided into 3 domains (A-α-C domains). It is known that an antibody 7G3 which recognizes A domain of human IL-3Rα blocks IL-3 signaling (Non-patent Document 11). In addition, expression of an A domain-deficient IL-3Rα molecule has been reported (Non-patent Document 12), and as a matter of course, an antibody which recognizes A domain cannot recognize A domain-deficient IL-3Rα. In addition, it is considered that C domain is the root of IL-3Rα molecule and has a high possibility to three-dimensionally inhibit association of IL-3Rβ with IL-3Rα.

IL-3 is the only a ligand which is known as a ligand of IL-3Rα. IL-3 is a hematopoietic factor which is known to accelerate colony formation of the following: erythrocyte, megakaryocyte, neutrophil, eosinophil, basophil, mast cell and a monocyte system cell. It is known that IL-3 also stimulates a precursor cell having pluripotency, but IL-3 is rather said to accelerate a differentiation of not an immature stem cell having autonomous replication ability but a precursor cell committed to differentiation.

It is known that IL-3Rα relates to the growth and differentiation of myeloid cells by forming a heterodimer with β chain and thereby transferring the IL-3 signaling into the cell via the Serine/Threonine phosphorylation pathway. It is known that IL-3Rα is expressed in Granulocyte-Macrophage Progenitor (GMP) or Common Myeloid Progenitor (CMP) among hematopoietic precursor cells and induces growth and differentiation into neutrophil and macrophage systems via the IL-3 signaling. On the other hand, it has been reported that the Megakaryocyte Erythroid Progenitor (MEP) presenting in the downstream of CMP does not express IL-3Rα different from the GMP which is also present in the downstream.

Regarding the AML stem cell, Bonnet and Dick have reported that the AML stem cell is present in the CD34 positive CD38 negative fraction (Non-patent reference 13). Further, by comparing with the same fraction (CD34 positive CD38 negative) of normal stem cell, Jordan et al. have found that IL-3Rα is highly expressed in the AML stem cell (Non-patent reference 14). A high potential of IL-3Rα as a marker of not only AML stem cell but also leukemia stem cell has also been reported in the plural of reports thereafter (Non-patent references 15 and 16). In the treatment of cancers including leukemia, it is important that only the cancer cells are removed without injuring normal cells as many as possible, and it is considered that this difference in the expression of IL-3Rα between normal stem cell and leukemia stem cell is useful in the treatment targeting at the leukemia stem cell.

Regarding IL-3Rβ which forms a heterodimer with IL-3Rα, there is no report that IL-3Rβ is highly expressed leukemia stem cell, and also in the case of a microarray in which expression of mRNA in leukemia stem cell and normal stem cell is compared in fact, IL-3Rβ is not identified as a molecule in which its expression is increased in leukemia stem cell (Non-patent reference 17).

Regarding IL-3Rβ which forms a heterodimer with IL-3Rα, there is no report that IL-3Rβ is highly expressed leukemia stem cell, and also in the case of a microarray in which expression of mRNA in leukemia stem cell and normal stem cell is compared in fact, IL-3Rβ is not identified as a molecule of which expression is increased in leukemia stem cell (Non-patent reference 18).

The presence of a leukemia cell which depends on IL-3 has been known for a long time, and the old studies are studies focused on a blast cell which occupies most of the leukemia cells. According to the recent studies on leukemia stem cell, it is said that the leukemia stem cell acquires antitumor agent resistance by exhaustively suppressing its growth. In addition, it is considered that an IL-3 reactive blast cell has high proliferation ability so that it is assumed that such a cell is effective in the general treatment using an antitumor agent.

As a candidate of the agent targeting at an IL-3R receptor, the IL-3 itself was administered for a long time to patients of hematopoietic insufficiency but it did not become a drug as a result. A clinical trial for a fusion protein in which diphtheria toxin is added to IL-3 is in progress aiming leukemia as a target of the disease. Regarding the IL-3 and diphtheria toxin-IL-3 fusion, these are not suitable as the agents which are targeting at cells in which expression of IL-3Rα is specifically increased, since IL-3 binds strongly not a protein of IL-3Rα alone but a hetero protein of IL-3Rα and β due to properties of IL-3. On the other hand, as a candidate of an agent targeting at IL-3Rα, a first phase result of an IL-3Rα human mouse chimeric antibody 7G3 has been reported (Non-patent Document 19). Since the 7G3 chimeric antibody uses for the purpose of blocking of IL-3 signaling as the mechanism of AML therapy, this is not an agent aimed at removing IL-3Rα positive cells. Also, although some other IL-3Rα antibodies are known (9F5 (Becton Dickinson), 6H6 (SANTA CRUZ BIOTECHNOLOGY) and AC 145 (Miltenyi-Biotech)), these do not have the ability to remove the cells highly expressing IL-3Rα.

Citation List
Patent Document
  Patent Document 1: EP Published Patent Application 120694
  Patent Document 2: EP Published Patent Application No. 125023
  Patent Document 3: GB Patent application No. GB2188638A
  Patent Document 4: U.S. Pat. No. 5,585,089
Non-Patent Document
  Non-patent Document 1: Osawa M et al., *Science.* 273:242-5 (1996)
  Non-patent Document 2: Goodell M A et al., *J Exp Med.* 183: 1797-806 (1996)
  Non-patent Document 3: Yamazaki S et al., *EMBO J.* 25: 3515-23 (2006)
  Non-patent Document 4: Ishikawa F et al., *Nat. Biotechnol.* 25:1315-21. (2007)
  Non-patent Document 5: Bao S et al., *Nature.* 444: 756-60 (2006)
  Non-patent Document 6: Schiff et al., *Canc. Res.,* 45, 879-885 (1985)
  Non-patent Document 7: Bruggemann et al., *J. Exp. Med.,* 170:2153-2157 (1989)
  Non-patent Document 8: Riechmann et al., *Nature,* 332: 323-327 (1988)
  Non-patent Document 9: Ishida I et al., *Cloning Stem Cells.* 4:91-102 (2002)
  Non-patent Document 10: Wu et al., *J Mol Biol.* 19:151-62 (1999)
  Non-patent Document 11: Sun et al., *Blood,* 87:83 (1996)
  Non-patent Document 12: Chen et al., *J Biol Chem,* 284: 5763 (2009)
  Non-patent Document 13: Bonnet et al., *Nat Med,* 1997; 3: 730
  Non-patent Document 14: Jordan et al., *Leukemia,* 2000; 14: 1777
  Non-patent Document 15: *Haematologica,* 2001; 86:1261
  Non-patent Document 16: LeukLymphoma, 2006; 47:207
  Non-patent Document 17: Majeti et al., *Proc Natl Acad Sci USA.* 2009; 106:3396
  Non-patent Document 18: Majeti et al., *Proc Natl Acad Sci USA.* 106:3396 (2009)
  Non-patent Document 19: *Blood,* 2008 112 (11): Abstract 2956

SUMMARY OF THE INVENTION

Technical Problems

An object of the invention is to provide a therapeutic agent which can remove leukemia stem cells alone and also can hardly exhibit adverse effects upon normal cells (shows fewer side effects). Specifically, the present invention provides an antibody to human IL-3Rα chain, which does not inhibit IL-3 signaling and binds to B domain of human IL-3Rα chain but does not bind to C domain; a composition comprising the antibody; and a therapeutic method or detection method comprising the antibody.

Solution to Problems

The invention relates to the following (1) to (9).

(1) An antibody to a human IL-3Rα chain, which does not inhibit IL-3 signaling and binds to B domain of human IL-3Rα chain but does not bind to C domain.

(2) The antibody described in the above-mentioned (1), further having high antibody-dependent cellular cytotoxicity (ADCC).

(3) The antibody described in the above-mentioned (1) or (2), wherein the high antibody-dependent cellular cytotoxicity (ADCC) shows a specific lysis rate of 10% at an antibody concentration of 0.01 µg/ml, by a Colon-26/hCD123 ADCC assay method which uses PBMC cultured with IL-2.

(4) The antibody described in any one of the above-mentioned (1) to (3), which comprises amino acid sequences of CDRs of heavy chain and CDRs of light chain selected from the group consisting of the following (a) to (e);
(a) CDR 1 to 3 of heavy chain are the amino acid sequences of SEQ ID NOs:113 to 115, respectively, and CDR 1 to 3 of light chain are the amino acid sequences represented by SEQ ID NOs:131 to 133, respectively,
(b) CDR 1 to 3 of heavy chain are the amino acid sequences of SEQ ID NOs:116 to 118, respectively, and CDR 1 to 3 of light chain are the amino acid sequences represented by SEQ ID NOs:134 to 136, respectively,
(c) CDR 1 to 3 of heavy chain are the amino acid sequences of SEQ ID NOs:119 to 121, respectively, and CDR 1 to 3 of light chain are the amino acid sequences represented by SEQ ID NOs:137 to 139, respectively,
(d) CDR 1 to 3 of heavy chain are the amino acid sequences represented by SEQ ID NOs:122 to 124, respectively, and CDR 1 to 3 of light chain are the amino acid sequences represented by SEQ ID NOs:140 to 142, respectively, and
(e) CDR 1 to 3 of heavy chain are the amino acid sequences represented by SEQ ID NOs:125 to 127, respectively, and CDR 1 to 3 of light chain are the amino acid sequences represented by SEQ ID NOs:143 to 145, respectively.

(5) The antibody described in any one of the above-mentioned (1) to (4), which comprises the heavy chain variable region and light chain variable region selected from the group consisting of the following (a) to (f);

(a) a heavy chain variable region comprising an amino acid sequence from glutamine (Q) at position 20 to serine (S) at position 139 in the amino acid sequence of SEQ ID NO:53 and a light chain variable region comprising an amino acid sequence from valine (V) at position 23 to lysine (K) at position 129 in the amino acid sequence of SEQ ID NO:55;

(b) a heavy chain variable region comprising an amino acid sequence from glutamine (Q) at position 20 to serine (S) at position 139 in the amino acid sequence represented by SEQ ID NO:57 and a light chain variable region comprising an amino acid sequence from valine (V) at position 23 to lysine (K) at position 129 in the amino acid sequence of SEQ ID NO:59;

(c) a heavy chain variable region comprising an amino acid sequence from glutamine (Q) at position 20 to serine (S) at position 139 in the amino acid sequence represented by SEQ ID NO:61 and a light chain variable region comprising an amino acid sequence from aspartic acid (D) at position 23 to lysine (K) at position 129 in the amino acid sequence of SEQ ID NO:63;

(d) a heavy chain variable region comprising an amino acid sequence from glutamine (Q) at position 20 to serine (S) at position 139 in the amino acid sequence of SEQ ID NO:65 and a light chain variable region comprising an amino acid sequence from aspartic acid (D) at position 23 to lysine (K) at position 129 in the amino acid sequence of SEQ ID NO:67;

(e) a heavy chain variable region comprising an amino acid sequence from glutamine (Q) at position 20 to serine (S) at position 138 in the amino acid sequence represented by SEQ ID NO:69 and a light chain variable region comprising an amino acid sequence from aspartic acid (D) at position 23 to lysine (K) at position 129 in the amino acid sequence of SEQ ID NO:71; and (f) a heavy chain variable region and/or light chain variable region, which comprise amino acid sequences in which 1 to 3 amino acid residues are deleted, substituted, added or inserted in the heavy chain variable region and/or light chain variable region shown by the above (a) to (e).

(6) A composition for preventing or treating a blood tumor in which a cell expressing IL-3Rα is found in bone marrow or peripheral blood of a subject, which comprises the IL-3Rα antibody described in any one of (1) to (5) as an active ingredient.

(7) A method for treating a blood tumor in which a cell expressing IL-3Rα is found in bone marrow or peripheral blood, which comprises administering, to a subject, a composition comprising the IL-3Rα antibody described in any one of (1) to (5) as an active ingredient.

(8) A composition for detecting a blood tumor in which a cell expressing IL-3Rα is found in bone marrow or peripheral blood of a biological sample from a subject, which comprises the IL-3Rα antibody described in any one of (1) to (5).

(9) The composition or method described in any one of (1) to (5), wherein the aforementioned blood tumor is acute myeloid leukemia (AML).

Advantageous Effect of the Invention

The invention can provide an antibody to human IL-3Rα chain, which does not inhibit IL-3 signaling and binds to B domain of human IL-3Rα chain but does not bind to C domain; a composition which comprises said antibody and a therapeutic method or detection method using said antibody.

BRIEF DESCRIPTION OF THE DRAWINGS

FIG. 4 is a graph in which, among the nucleotide and amino acid sequences of A and B domains of human IL-3Rα molecule, parts of regions in which the regions 1 to 7 arranged on the outside of the molecule are substituted by the GM-CSFRα sequence are shown by dotted lines.

MODE FOR CARRYING OUT THE INVENTION

Detailed Description of Specified Desirable Embodiments

Figure 1:
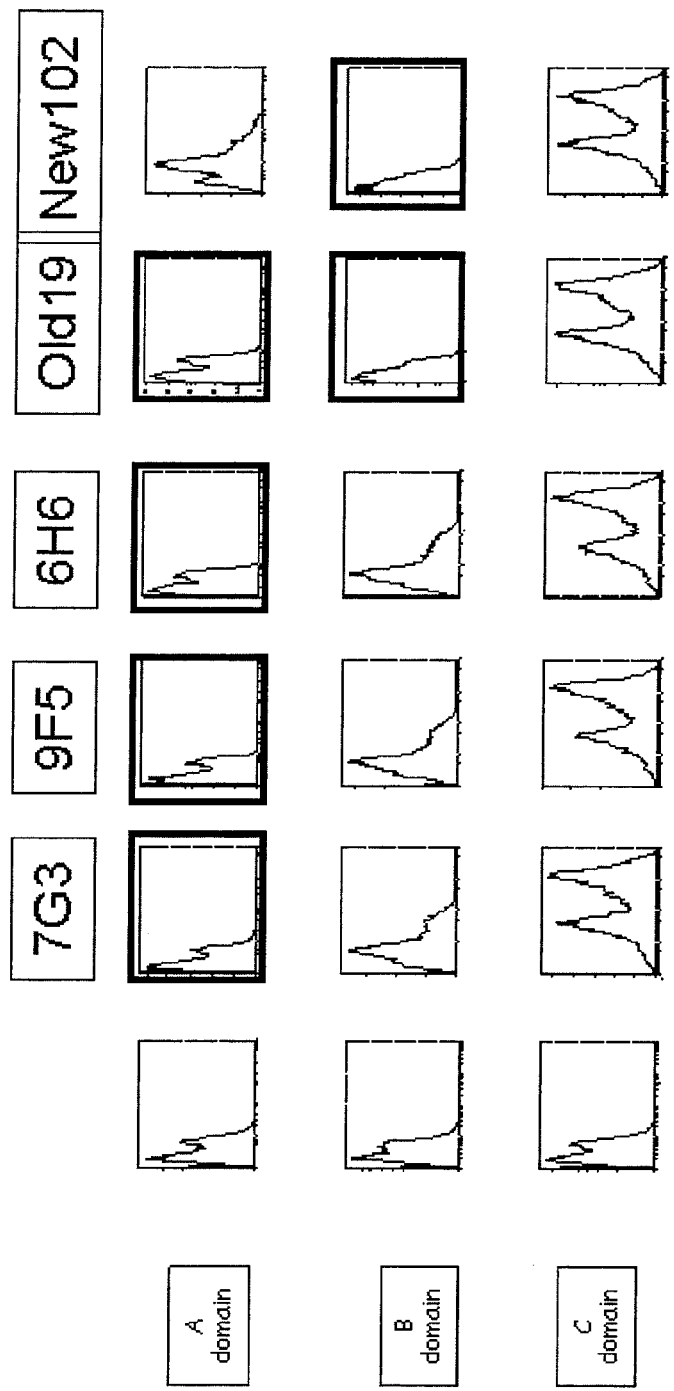
FIGS. 1 and 2 are results of a flow cytometry analysis of a cell expressing an IL-3Rα/GM-CSFRα chimeric protein using a labeled anti-IL-3Rα antibody.

Headings of the sections to be used in this specification are only for the purpose of organization and should not be interpreted as limitation to the main subject to be described. All of the cited references cited in this application are clearly incorporated by references into this specification for optional purposes.

(Outline)

This invention relates to an antibody to human IL-3Rα chain, which does not inhibit IL-3 signaling and binds to B domain of human IL-3Rα chain (hereinafter referred to as IL-3Rα) but does not bind to C domain.

IL-3 receptors (hereinafter referred to as IL-3R), particularly IL-3Rα, are expressed on the cell surface of a leukemia stem cell. In general, IL-3 receptor β chain (hereinafter referred to as IL-3Rβ) transfers IL-3 signaling into the cell and therefore induces growth and differentiation.

Accordingly, there is a possibility that inhibition of IL-3 signaling cause side effects such as inhibition of normal hematopoietic action by a normal stem cell. Thus, as a new therapeutic method which targets at leukemia stem cell, it is preferable that the method targets at IL-3Rα and also does not inhibit IL-3 signaling.

(IL-3Rα)

A protein encoded by IL-3Rα gene is a type I transmembrane protein which belongs to a cytokine receptor family. In normal cells, the IL-3Rα molecule is expressed on a part of hematopoietic precursor cells, basophil, a part of dendritic cells and the like. In the case of tumors, it is known to be expressed in a hematopoietic system cancer and leukemia. As examples of tumors which express IL-3Rα, it is known that IL-3Rα is expressed on the blast cell of AML and CML in blastic crisis phase, and in the case of a differentiation marker-negative CD34 positive CD38 negative fraction considered to be a leukemia stem cell, in AML, CML, MDS, ALL and SM. In blood, IL-3 which is a known ligand of IL-3Rα is expressed on an activated T cell, a natural killer cell, a mast cell and a part of cells of megakaryocyte system. In addition, the IL-3Rα is also called CD123. The IL-3Rα includes a mammal (e.g., the primates and human) type IL-3Rα. The IL-3Rα sequence includes polymorphic variants. Specific examples of the full length human IL-3Rα include the following amino acid sequences.

```
                                               (SEQ ID NO: 1)
MVLLWLTLLLIALPCLLQTKEDPNPPITNLRMKAKAQQLTWDLNRNVT

DIECVKDADYSMPAVNNSYCQFGAISLCEVTNYTVRVANPPFSTWILF

PENSGKPWAGAENLTCWIHDVDFLSCSWAVGPGAPADVQYDLYLNVAN

RRQQYECLHYKTDAQGTRIGCRFDDISRLSSGSQSSHILVRGRSAAFG

IPCTDKFVVFSQIEILTPPNMTAKCNKTHSFMHWKMRSHFNRKFRYEL

QIQKRMQPVITEQVRDRTSFQLLNPGTYTVQIRARERVYEFLSAWSTP

QRFECDQEEGANTRAWRTSLLIALGTLLALVCVFVICRRYLVMQRLFP

RIPHMKDPIGDSFQNDKLVVWEAGKAGLEECLVTEVQVVQKT
```

Specific examples of amino acid sequence of the extracellular region of human IL-3Rα include the following amino acid sequence.

```
                                               (SEQ ID NO: 2)
MVLLWLTLLLIALPCLLQTKEDPNPPITNLRMKAKAQQLTWDLNRNVT

DIECVKDADYSMPAVNNSYCQFGAISLCEVTNYTVRVANPPFSTWILF

PENSGKPWAGAENLTCWIHDVDFLSCSWAVGPGAPADVQYDLYLNVAN

RRQQYECLHYKTDAQGTRIGCRFDDISRLSSGSQSSHILVRGRSAAFG

IPCTDKFVVFSQIEILTPPNMTAKCNKTHSFMHWKMRSHFNRKFRYEL

QIQKRMQPVITEQVRDRTSFQLLNPGTYTVQIRARERVYEFLSAWSTP

QRFECDQEEGANTRAWRTSL
```

In addition, the extracellular region of IL-3Rα is divided into three domains of A to C.

A domain comprises a region from glutamine (Q) at position 18 to serine (S) at position 100 in the amino acids of SEQ ID NO:2, and B domain comprises from glycine (G) at position 101 to serine (S) at position 203 in the amino acids of SEQ ID NO:2 and C domain that from glutamine (Q) at position 204 to leucine (L) at position 308 in the amino acids of SEQ ID NO:2.

Further, in A domain and B domain, the following 7 regions are arranged on the outside of the molecule.

The region 1 is from aspartic acid (D) at position 55 to proline (P) at position 61 in the amino acids of SEQ ID NO:2, the region 2 is from valine (V) at position 63 to phenylalanine (F) at position 70 in the amino acids of SEQ ID NO:2, the region 3 is from serine (S) at position 91 to glutamic acid (E) at position 98 in the amino acids of SEQ ID NO:2, the region 4 is from proline (P) at position 97 to tryptophan (W) at position 104 in the amino acids of SEQ ID NO:2, the region 5 is from cysteine (C) at position 122 to proline (P) at position 128 in the amino acids of SEQ ID NO:2, the region 6 is from isoleucine (I) at position 182 to serine (S) at position 188 in the amino acids of SEQ ID NO:2 and the region 7 is from glycine (G) at position 192 to lysine (K) at position 198 in the amino acids of SEQ ID NO:2.

Accordingly, examples of the antibody of the invention include an antibody which binds to an amino acid sequence of positions 101 to 203 in the amino acids of SEQ ID NO:2 which is the extracellular region of IL-3Rα, but does not bind to an amino acid sequence of positions 204 to 308, and an antibody which further binds to amino acid sequences of positions 182 to 188 and positions 192 to 198 in the amino acid sequence of SEQ ID NO:2.

The antibody of the invention binds to the above-mentioned specific regions of the extracellular region of IL-3Rα and does not inhibit IL-3 signaling.

The term "does not inhibit IL-3 signaling" as used in the invention means that it does not inhibit the intracellular signal through IL-3R by IL-3, and it includes a case in which the association of IL-3 with IL-3R is not inhibited and the binding of IL-3Rα chain and β chain is not inhibited. Specifically, it means that the cell growth inhibition ratio shown by FIG. 5 according to the analysis in Example 8 is 40% or more, preferably 60% or more, further preferably 80% or more, when the antibody concentration is set to 10 µg/ml. According to this specification, the terms "blocking of IL-3 signaling" and "inhibition of IL-3 signaling" are used as the same meaning and not discriminated, and the blocking activity of IL-3 signaling means the ability to inhibit IL-3 signaling.

Also, the antibody of the invention has high antibody-dependent cellular cytotoxicity (ADCC) in addition to the above-mentioned properties.

The IL-3Rα antibody having ADCC activity means an antibody which binds to a cell expressing IL-3Rα to kill the IL-3Rα-expressing cell via an effector cell having cytotoxicity such as NK cell and the like.

The high ADCC activity means that the specific lysis rate is 10% or more at an antibody concentration of 0.01 µg/ml or less when measured by a Colon-26/hCD123 ADCC assay method which uses PBMC cultured with IL-2.

The specific lysis rate means a value obtained by measuring the lysis rate of a target cell by an antibody and specifically it can be calculated in accordance with the following Example 11.

Examples of the cell expressing IL-3Rα include blood cancer cells (acute myeloid leukemia (AML) cells, chronic myeloid leukemia (CML) cells, myelody splastic syndromes (MDS) cells, acute lymphoid leukemia (ALL) cells, chronic lymphoid leukemia (CLL) cells, multiple myeloma (multiple myeloma: MM) cells, systemic mastocytoma (SM) cells etc.), regulatory T cells (such as CD4-positive CD25-positive cell), antigen presenting cells (such as dendritic cells, monocytes, macrophages and similar cells thereto (hepatic stellate cells, osteoclasts, microglial cells, the major epidermal phagocytic cells, dust cells (alveolar macrophages), etc.)), basophils and the like.

In addition, AML cell, CML cell, ALL cell, CLL cell, MDS cell, SM cell, MM cell, various lymphoma cells include their cancer stem cells.

The cancer stem cell is one of the cell groups constituting tumor. For example, in acute myeloid leukemia (AML) it is represented by Lineage(−)CD34(+)CD38(−) myeloid cell. Accordingly, since the antibody of the invention has high ADCC activity, it induces reduction or elimination of cells expressing IL-3Rα.

Also, the IL-3Rα antibody of the invention includes an IL-3Rα antibody which has CDRs of heavy chain and CDRs of light chain selected from the group consisting of the following (a) to (e);
(a) CDR 1 to 3 of heavy chain are the amino acid sequences represented by SEQ ID NOs:113 to 115, respectively, and CDR 1 to 3 of light chain are the amino acid sequences represented by SEQ ID NOs:131 to 133, respectively, (b) CDR 1 to 3 of heavy chain are the amino acid sequences represented by SEQ ID NOs:116 to 118, respectively, and CDR 1 to 3 of light chain are the amino acid sequences represented by SEQ ID NOs:134 to 136, respectively, (c) CDR 1 to 3 of heavy chain are the amino acid sequences represented by SEQ ID NOs:119 to 121, respectively, and CDR 1 to 3 of light chain are the amino acid sequences represented by SEQ ID NOs:137 to 139, respectively, (d) CDR 1 to 3 of heavy chain are the amino acid sequences represented by SEQ ID NOs:122 to 124, respectively, and CDR 1 to 3 of light chain are the amino acid sequences represented by SEQ ID NOs:140 to 142, respectively, and (e) CDR 1 to 3 of heavy chain are the amino acid sequences represented by SEQ ID NOs:125 to 127, respectively, and CDR 1 to 3 of light chain are the amino acid sequences represented by SEQ ID NOs:143 to 145, respectively.

In addition, the antibody of the invention includes an IL-3Rα antibody which comprises the heavy chain variable region and the light chain variable region selected from the group consisting of the following (a) to (f) (shown in parentheses are names of the antibodies which are described in the following Examples from which each of variable regions are derived);

(a) a heavy chain variable region comprising an amino acid sequence from glutamine (Q) at position 20 to serine (S) at position 139 in the amino acid sequence represented by SEQ ID NO:53 and a light chain variable region comprising an amino acid sequence from valine (V) at position 23 to lysine (K) at position 129 in the amino acid sequence represented by SEQ ID NO:55 (name of antibody: Old4)

(b) a heavy chain variable region comprising an amino acid sequence from glutamine (Q) at position 20 to serine (S) at position 139 in the amino acid sequence represented by SEQ ID NO:57 and a light chain variable region comprising an amino acid sequence from valine (V) at position 23 to lysine (K) at position 129 in the amino acid sequence represented by SEQ ID NO:59 (name of antibody: Old5)

(c) a heavy chain variable region comprising an amino acid sequence from glutamine (Q) at position 20 to serine (S) at position 139 in the amino acid sequence represented by SEQ ID NO:61 and a light chain variable region comprising an amino acid sequence from aspartic acid (D) at position 23 to lysine (K) at position 129 in the amino acid sequence represented by SEQ ID NO:63 (name of antibody: Old17)

(d) a heavy chain variable region comprising an amino acid sequence from glutamine (Q) at position 20 to serine (S) at position 139 in the amino acid sequence represented by SEQ ID NO:65 and a light chain variable region comprising an amino acid sequence from aspartic acid (D) at position 23 to lysine (K) at position 129 in the amino acid sequence represented by SEQ ID NO:67 (name of antibody: Old 19)

(e) a heavy chain variable region comprising an amino acid sequence from glutamine (Q) at position 20 to serine (S) at position 138 in the amino acid sequence represented by SEQ ID NO:69 and a light chain variable region comprising an amino acid sequence from aspartic acid (D) at position 23 to lysine (K) at position 129 in the amino acid sequence represented by SEQ ID NO:71 (name of antibody: New102) and (f) a heavy chain variable region and/or light chain variable region, which comprise amino acid sequences in which 1 to 3 amino acid residues are deleted, substituted, added or inserted in the heavy chain variable region and/or light chain variable region shown by (a) to (e).

(Antibody)

The antibody is used in a most broad sense and includes a monoclonal antibody, a polyclonal antibody, a multivalent antibody, a multispecific antibody (e.g., bispecific antibody) and also antibody fragments as long as these exhibit the desired biological activity.

The antibody contains a mature heavy chain or light chain variable region sequence. In addition, the antibody also includes a modified form and variant form such as substitutions within or outside of a constant region, a complementary determining region (CDR) or a framework (FR) region antibody of a mature heavy or light chain variable region sequence of the antibody, and the like. In a specific embodiment, the substitution includes a conservative amino acid substitution is included in the substitution.

In addition, the antibody also includes a subsequence of the mature heavy chain or light chain variable region sequence. In a specific embodiment, the subsequence is selected from Fab, Fab', F(ab')$_2$, Fv, Fd, single chain Fv (scFv), disulfide bond Fv (sdFv) and VL or VH.

In addition, the antibody also includes a heterogeneous domain. In a specific embodiment, the heterogeneous domain includes a tag, a detectable label or a cytotoxic agent.

Examples of the antibody include a monoclonal antibody and a polyclonal antibody and any isotype or subclass thereof. In a specific embodiment, the aforementioned antibody is an isotype of IgG (e.g., IgG1, IgG2, IgG3 or IgG4), IgA, IgM, IgE or IgD. The "monoclonal" antibody means an antibody that is based upon, obtained from a single clone including a eukaryote clone, a prokaryote clone or a phage clone or derived from a single clone including a eukaryote clone, a prokaryote clone or a phage clone, based on a single clone including a eukaryote clone, a prokaryote clone or a phage clone. Accordingly, the "monoclonal" antibody is a structurally defined substance and not a method by which it is produced.

The IL-3Rα antibody, anti-IL-3Rα and anti-IL-3Rα antibody mean an antibody which specifically binds to IL-3Rα. The specific binding means that it is selective for the epitope presenting in IL-3Rα. The specific binding can be distinguished from non-specific binding using a known assay in the technical field (e.g., immunoprecipitation, ELISA, flow cytometry, Western blotting).

When all or a part of antigen epitopes to which an IL-3Rα antibody specifically binds are present in different proteins, there is a possibility that this antibody can bind to the different proteins. Therefore, there is a possibility that the IL-3Rα antibody specifically binds to other protein having high sequence or structural homology to IL-3Rα epitope depending on the sequence or structural homology to IL-3Rα epitope. Accordingly, there is a possibility that IL-3Rα antibody binds to a different protein when an epitope having sufficient sequence or structural homology is present in the different protein.

The IL-3Rα antibody includes isolated and purified antibodies. The antibody of the invention including an isolated or purified IL-3Rα antibody includes human.

The term "(be) isolated" to be used as a modifier of a composition means that the composition is prepared by the hand of man or separated from one or more other components in vivo environment presenting in nature generally by one or more manipulative steps or processes. In general, a composition separated in this manner does not substantially contain one or more materials with which they normally associate in nature, such as one or more proteins, nucleic acids, lipids, carbohydrates and cell membranes. Because of this, the isolated composition is separated from other biological components in the cells of the organism in which the composition naturally occurs, or from the artificial medium in which it is produced (e.g., by synthesis or cell culture). For example, an isolated IL-3Rα antibody can be obtained from an animal in which the antibody is produced (e.g., non-transgenic mammals or transgenic mammals (rodents (mouse) or the ungulates (cattle)) and is separated from other polypeptides and nucleic acids. Accordingly, it is considered that the serum containing an antibody obtained from such an animal is isolated. The term "(be) isolated" does not exclude alternative physical forms, and for example, an isolated antibody could include antibody subsequences and chimeras, multimers or derivatized forms.

The term "(be) purified" to be used as a modifier of a composition refers to a composition which is free of most of or substantially all of the materials with which it typically associates in nature. In general, a purified antibody is obtained from the components generally presenting in the antibody environment. Because of this, it is considered that an antibody supernatant which is separated from a cell culture mixture of an antibody producing hybridoma is purified. Accordingly, the "(be) purified" does not require absolute purity and is context specific. Furthermore, the "(be) purified" composition can be combined with one or more other molecules. Because of this, the term "(be) purified" does not exclude combination of composition. The purity can be determined by an optional appropriate method such as UV spectrometry, chromatography (e.g., HPLC, gas phase), gel electrophoresis (e.g., silver or Coomassie staining), sequence analysis (peptide and nucleic acid) and the like.

The "(be) purified" protein and nucleic acid include a protein and a nucleic acid which are obtained by a standard purification method. Also, a protein and a nucleic acid obtained by recombination expression in a host cell and chemical synthesis are also included in this term. In addition, the "(be) purified" can also refer to a composition in which the level of contaminants is lower than the level which is acceptable to a regulatory agency for administration to human or non-human animals, such as the Food and Drug Administration (FDA).

The IL-3Rα antibody includes an antibody which binds to IL-3Rα and modulates function or activity of IL-3Rα in vivo or in vitro (e.g., in a subject). In the specification, the "to modulate" and the grammatical variations thereof when used in relation to the activity or function of IL-3Rα mean that the IL-3Rα activity or function is detectably affected, modified or altered but does not include inhibition of IL-3 signaling. Accordingly, the IL-3Rα antibody which modulates the activity or function of IL-3Rα is an antibody that provides influence, modification or alteration such that one or more of the IL-3Rα activity or function can be detected without inhibiting IL-3 signaling, and such an activity or function of IL-3Rα can includes, for example, binding of IL-3Rα with an IL-3Rα ligand (e.g., IL-3), an IL-3Rα-mediated signal transfer or an IL-3Rα-mediated cell response or a cell response that can be modulated by IL-3Rα, or the activity or function of other IL-3Rα described in the specification or, otherwise, is commonly known or can be known.

Examples of various non-limited IL-3Rα activities and functions which can be modulated include IL-3Rα mediated signal transduction or IL-3Rα mediated cellular response, cellular response which can be modulated via IL-3Rα, cell proliferation or cell expansion (e.g., AML cell, CML cell, ALL cell, CLL cell, MDS cell, MM cell, SM cell, various lymphoma cells, monocytes, macrophages, mast cells, basophils, helper T cells, regulatory T cells, natural killer cells, myeloid progenitor cells and lymphoid progenitor cells), cell survival or apoptosis (e.g., AML cell, CML cell, ALL cell, CLL cell, MDS cell, MM cell, SM cell, various lymphoma cells, monocytes, macrophages, mast cells, basophils, helper T cells, regulatory T cells, natural killer cells, myeloid progenitor cells and lymphoid progenitor cells), cytokines (e.g., Th1, Th2 and non-Th1/Th2 cytokines) and interferon expression or production, expression or production of anti-apoptosis protein or proapoptosis protein, treatment, suppression or improvement of disorder, disease, physiological condition, pathological condition and symptom. Specific cytokines to be modulated are not limited and examples include IL-1, IL-2, IL-4, IL-5, IL-6, IL-9, IL-10, IL-14, IL-16, IL-17, IL-23, IL-26, TNF-α, and interferon γ (in vitro or in vivo). Specific anti-apoptosis proteins and proapoptosis proteins are not limited and examples include Bcl-xL, Bcl-2, Bad, Bim, and Mcl-1.

Therefore, examples of anti-IL-3Rα antibody described in the present specification include an antibody which modulates IL-3Rα mediated signal transduction or IL-3Rα mediated cellular response, cellular response which can be modulated via IL-3Rα, cell proliferation or cell growth (e.g., AML cell, CML cell, ALL cell, CLL cell, MDS cell, MM cell, SM cell, various lymphoma cells, monocytes, macrophages, mast cells, basophils, helper T cells, regulatory T cells, natural killer cells, myeloid progenitor cells and lymphoid progenitor cells), cell survival or apoptosis (e.g., AML cell, CML cell, ALL cell, CLL cell, MDS cell, MM cell, SM cell, various lymphoma cells, monocytes, macrophages, mast cells, basophils, helper T cells, regulatory T cells, natural killer cells, myeloid progenitor cells and lymphoid progenitor cells), cytokines (e.g., Th1, Th2 and non-Th1/Th2 cytokines) and interferon expression or production, expression or production of anti-apoptosis protein or proapoptosis protein, treatment, suppression or improvement of disorder, disease, physiological condition, pathological condition and symptom. In the specific embodiments, anti-IL-3Rα antibody of the present invention can modulate expansion or survival of AML cell, number of other blood cancer cell (e.g., CML cell, ALL cell, MDS cell, MM cell, SM cell or various lymphoma cell), growth or survival of non-cancer blood cell such as monocytes, macrophages, mast cells, basophils, helper T cells, regulatory T cells, natural killer cells, myeloid progenitor cells and lymphoid progenitor cells, and reduces, disappears or depletes AML cell, CML cell, ALL cell, CLL cell, MDS cell, MM cell, SM cell, or various lymphoma cells.

The IL-3Rα antibody includes a modified form such as a substitution product (e.g., an amino acid substitution product) which is also called as "variant", an addition product, deletion product (e.g., a subsequence or fragment) and the like. Such modified antibody forms and variants retain at least partial function or activity of the IL-3Rα antibody shown by the invention, such as binding with IL-3Rα, or modulation of activity or function (e.g., IL-3Rα signal transfer) of IL-3Rα. Accordingly, the modified IL-3Rα antibody can retain the ability to modulate, for example, at least partial of IL-3Rα binding or one or more of the IL-3Rα functions or activities (e.g., signal transfer, cell response and the like).

According to this specification, the term "to alter" ("to modify") and the grammatical variations thereof means that the composition derivarates a reference composition. The modified proteins, nucleic acids and other compositions can have higher or lower activities than a reference unmodified protein, nucleic acid or other composition or can have a different function from a reference unmodified protein, nucleic acid or other composition.

Such an antibody containing an amino acid substitution can be encoded by nucleic acid. Accordingly, the present invention also provides a nucleotide sequence encoding an antibody containing an amino acid substitution.

The term "identity" or "identical" means that two or more referenced substances are the same. Accordingly, when two protein sequences (e.g., IL-3Rα antibodies) are identical, they have the same amino acid sequences at least within the referenced regions or portion. The term "identical region" means an identical region of two or more referenced substances. Thus, when two protein sequences are identical over one or more sequence regions, they have identity within the regions. "Substantial identity" means that a molecule is structurally or functionally conserved such that the molecule has or is predicted to have at least partial function or activity of one or more of reference molecule functions or activities or relevant/corresponding region or a portion of the reference molecule to which it shares identity. Thus, polypeptides having substantial identity (e.g., IL-3Rα antibodies) have or are predicted to have at least a part of the activity or function as a referenced polypeptide (e.g., IL-3Rα antibody). For example, in a specific embodiment, it is considered that an IL-3Rα antibody having one or more modifications (e.g., deletion, substitution, addition or insertion of 1 to 3 amino acid residues) which retain at least partial activity or function of the unmodified IL-3Rα antibody has substantial identity to the reference IL-3Rα antibody.

Due to variations between structurally related protein and functionally related protein, the amount of sequence identity required to retain functions or activity on the protein, region and function or activity of the region. In the case of protein, an activity or function can be retained by the presence of merely 30% of amino acid sequence identity, but in general, higher identity of 50%, 60%, 75%, 85%, 90%, 95%, 96%, 97% or 98%, to the reference sequence is present. The extent of identity between two sequences can be verified using a computer program or mathematic algorithm conventionally known in the technical field. In such an algorithm which calculates ratio of sequence identity (homology), in general, sequence gaps and mismatches over the comparison region are accounted. For example, BLAST (e.g., BLAST 2.0) retrieval algorithm (e.g., see Altschul et al., *J. Mol. Biol.*, 215: 403 (1990), publicly available through NCBI) has the following illustrative retrieval parameters: mismatch-2; gap start 5; gap elongation 2. In the polypeptide sequence comparison, the BLASTP algorithm is typically used in combination with a scoring matrix such as PAM 100, PAM 250, BLOSUM 62, BLOSUM50.FASTA (e.g., FASTA 2 and FASTA 3) and the like, and SSEARCH sequence comparison program is also used for determining the extent of identity (Pearson et al., *Proc. Natl. Acad. Sci. USA*, 85: 2444 (1988); Pearson, Methods Mol. Bio., 132: 185 (2000); and Smith et al., J. Mol. Biol., 147: 195 (1981)). A program has also been developed for determining protein structural similarity using topological mapping based on Delaunary (Bostick et al., *Biochem. Biophys. Res. Commun.*, 304: 320 (2003)).

A "conservative substitution" is a substitution of one amino acid by a biologically, chemically or structurally similar residue. Biological similarity means that a biological activity such as IL-3Rα binding activity is not destroyed by the substitution. Structural similarity means that amino acids have side chain with similar length (e.g., alanine, glycine and serine) or have similar size. Chemical similarity means that the residues have the same charge or are hydrophilic or hydrophobic. Specific examples include substitution of one hydrophobic residue such as isoleucine, valine, leucine, and methionine with other residue, or the substitution of one polar residue with other residue such as the substitution of arginine with lysine, the substitution of glutamic acid with aspartic acid, or the substitution of glutamine with asparagine, and the substitution of serine with threonine.

In addition, examples of the modified antibody include peptide mimetics having one or more D-amino acids substituted with L-amino acids (and a mixture thereof), structural and functional analogs such as synthesized or non-natural amino acids or amino acid analogs, and derivatized form thereof. Examples of modification include a cyclic structure such as an end-to-end amide bond between the amino and carboxy-terminus of the molecule or intra- or inter-molecular disulfide bond or intramolecular or intermolecular disulfide bond.

Additional non-limiting specific examples of the amino acid modifications include partial sequence (subsequence) and fragment of IL-3Rα. Exemplary subsequence and fragment of IL-3Rα include a part of the IL-3Rα sequence to which the exemplary IL-3Rα antibody of the invention binds. Also, the exemplary subsequence and fragment of IL-3Rα include an immunogenicity region such as a part of the IL-3Rα to which the exemplary IL-3Rα antibody of the invention binds.

According to the invention, there is provided a nucleic acid encoding an IL-3Rα antibody subsequence of fragment which retains at least a part of the function or activity of the IL-3Rα antibody and an unmodified or reference IL-3Rα antibody. In this specification, the term "subsequence" or "fragment" means a portion of a full length molecule. The amino acid sequence encoding the subsequence of the IL-3Rα antibody has amino acids of smaller than those of the full length IL-3Rα antibody by at least one (e.g., deletion of one or more inner or terminal amino acids from the amino terminus or carboxy terminus). The subsequence of IL-3Rα antibody has amino acids of smaller than those of the full length IL-3Rα antibody by at least one. The nucleic acid subsequence has nucleotides of smaller than those of the full length comparative nucleic acid sequence by at least one. Accordingly, the subsequence can be an optional length within the full length of native IL-3Rα.

The IL-3Rα antibody subsequence and fragment can have a binding affinity as the full length antibody, a binding specificity as the full length antibody or one or more activities or functions as the full length antibody, such as the function or activity of an IL-3Rα antagonist or agonist antibody. The terms "functional subsequence" and "functional fragment" in the case of referring to the antibody mean an antibody portion which retains one or more functions or activities as the full length reference antibody, such as at least a part of the function or activity of IL-3Rα antibody. For example, an antibody subsequence which binds to IL-3Rα or a fragment of IL-3Rα is considered a functional subsequence.

The antibody subsequence and fragment can be combined. For example, a VL or VH subsequence can be connected by a linker sequence and thereby can form a VL-VH chimeric body. A combination of single chain Fv(scFv) subsequences can be connected by a linker sequence and thereby can form a scFv-scFv-chimeric body. The IL-3Rα antibody subsequence and fragment include a single chain antibody or variable region alone or in combination with all or a portion of other IL-3Rα antibody subsequence.

The antibody subsequence and fragment can be prepared by hydrolysis of the antibody by its proteolysis for example by a pepsin or papain digestion of the whole antibody. The antibody subsequence and fragment obtained by enzymatic cleavage with pepsin provide a 5S fragment represented by F(ab')$_2$. This fragment can be further cleaved using a thiol reducing agent to form a 3.5S Fab' monovalent fragment. Alternatively, an enzymatic cleavage using pepsin directly produces two monovalent Fab' fragments and Fc fragment (see e.g., U.S. Pat. Nos. 4,036,945 and 4,331,647; and Edelman et al., *Methods Enzymol.,* 1: 422 (1967)). Other methods of cleaving an antibody, such as separation of heavy chain for forming a monovalent light chain-heavy chain fragment, further cleavage of the fragment or other enzymatic or chemical method may be used.

A protein and an antibody, as well as subsequence thereof and fragment can be prepared using a genetic engineering. The technology includes the full or partial gene encoding a protein or an antibody is expressed in a host cell such as a COS cell and *E. Coli.* A recombinant host cell synthesizes the full or subsequence such as scFv (such as Whitlow et al, In: Methods: *A Companion to Methods in Enzymology* 2:97 (1991), Bird et al, *Science* 242:423 (1988); and U.S. Pat. No. 4,946,778). A single chain Fv and an antibody can be prepared in accordance with the procedure as described in U.S. Pat. Nos. 4,946,778 and 5,258,498; Huston et al, *Methods Enzymol* 203:46 (1991); Shu et al, *Proc. Natl. Acad. Sci. USA* 90:7995 (1993); and Skerra et al, *Science* 240:1038 (1988).

The modified form includes a derivatized sequence such as amino acids in which the free amino groups form amine hydrochloride, p-toluenesulfonyl group and carbobenzoquinone group; the free carboxy groups which form a salt or methyl and ethyl ester; and the free hydroxyl groups form an O-acyl or O-alkyl derivative, and naturally existing amino acid derivatives such as 4-hydroxyproline (derivative of proline), 5-hydroxylysine (derivative of lysine), homoserine (derivative of serine), ornithine (derivative of lysine) and the like. The modification can be carried out using a method conventionally known in the technical field (e.g., site-specific deletion or insertion mutagenesis based on PCR, chemical modification and mutagenesis, crosslinking and the like).

Addition products and insertion products are included in the modified forms of protein (e.g., antibody), nucleic acid and other compositions. For example, the addition can be a covalent or non-covalent bond with any type of molecules of protein (e.g., antibody), nucleic acid or other compositions. In general, addition and insertion confer different function or activity.

Fusion (chimeric) polypeptides or nucleic acid sequences are included in the addition product and insertion product, and these are sequences having one or more molecules which are generally not present in the reference native (wild type) sequence covalently attached to the aforementioned sequence. A specific example is an amino acid sequence of other protein (e.g., an antibody) for producing a multifunctional protein (e.g., a multispecific antibody).

Also, the antibody of the invention include a chimeric or fusion product in which one or more additional domains are covalently linked thereto in order to confer a different or complementary function or activity. Examples of the antibody include a chimeric or fusion product which does not naturally present in natural and in which two or more amino acid sequences are mutually bonded.

According to the invention, there are provided an IL-3Rα antibody which contains a heterologous domain and a nucleic acid that encodes the IL-3Rα antibody. The heterologous domain can be an amino acid addition product or insertion product, but does not limited to an amino acid residue. Accordingly, the heterologous domain can be composed of any one of various different types of small or large functional parts. Such a part includes a nucleic acid, a peptide, a carbohydrate, a lipid or small organic compound such as a drug, a metal (gold, silver) and the like.

Non-limiting specific examples of the heterologous domain include a tag, a detectable label and a cytotoxic agent. Specific examples of the tag and detectable label include T7-, His-, myc-, HA- and FLAG-tags; enzymes (horseradish peroxidase, urease, catalase, alkaline phosphatase, β-galactosidase, chloramphenicol transferase); enzyme substrates; ligands (e.g., biotin); receptors (avidin); radionuclide (e.g., C14, S35, P32, P33, H3, I125 and I131); electron density reagents; energy transfer molecules; paramagnetic labels; fluorophore (fluorescein, Rhodamine, Phycoerythrin); chromophore; chemiluminescence agents (imidazole, luciferase) and bioluminescence agents. Specific examples of the cytotoxic agent include diphtheria toxin (diphtheria, toxin), cholera toxin and lysine.

A linker sequence may be inserted between the protein (e.g., an antibody), nucleic acid or other composition and the addition product or insertion product (e.g., a heterologous domain) so that the two substances maintain at least a part of different function or activity. The linker sequence may have one or more properties which can accelerate either of the domains or can carry out mutual reaction with either of the domains, and such characteristics include impossibility to form a flexible structure and an ordered secondary structure or hydrophobic property or charging property. Examples of the amino acids which are generally found in the flexible protein regions include glycine, asparagine and serine. Other amino acids close to neutral such as threonine and alanine may also be used in the linker sequence. The length of the linker sequence can be varied (e.g., see U.S. Pat. No. 6,087, 329). The linker further include chemical crosslinking agents and binding agents (conjugating agents) such as a sulfosuccinimidyl derivative (sulfo-SMCC, sulfo-SMPB), disuccinimidyl suberate (DSS), disuccinimidyl glutarate (DSG) and disuccinimidyl tartarate (DST).

Further examples of the addition include any one of glycosylation, fatty acid, lipid, acetylation, phosphorylation, amidation, formylation, ubiquitination and derivatiation by a protecting or blocking group and a large number of chemical modifications. Other substitutions and possibilities can be easily understood by those skilled in the art and are considered to be within the scope of the invention.

Such a modified sequence can be prepared using recombinant DNA techniques which mediate cell expression or in vitro translation. Polypeptides and nucleic acid sequences can also be prepared by a conventionally known method in the technical field such as chemical synthesis using an automatic peptide synthesizer (see e.g., Applied Biosystems, Foster City Calif.).

Modified and variant antibodies such as substitution products, subsequences addition products and the like can maintain detectable activity of IL-3Rα antibody. In an embodiment, the modified antibody has the activity to bind to IL-3Rα molecule and induces reduction or elimination of IL-3Rα expression cells by an immune system mainly centering on an effector cell. The modified antibody relates to the functional control of IL-3Rα expression cells and induces survival, growth, resting, cell death and the like of the cells. The cell death includes apoptosis, necrosis, autophagy and the like.
(Screening Method of IL-3Rα)

According to the invention, there are further provided a cell-free method and a cell-based method (e.g., in vivo or in vitro) which screen, detect and identify IL-3Rα (e.g., in a solution or by a solid phase). These methods can be carried out in a solution in vitro using a biomaterial or sample, and in vivo for example using a sample of an animal-derived cell (e.g., lymphocyte). In an embodiment, the method comprises a step of contacting a biomaterial or sample with an antibody bound to IL-3Rα under a condition of allowing binding of the antibody with IL-3Rα and a step of assaying for the antibody bound to IL-3Rα. The presence of IL-3Rα is detected by binding of the antibody to bind to IL-3Rα. In an embodiment, IL-3Rα is present in a cell or tissue. In another embodiment, the aforementioned biomaterial or sample is obtained from a mammal analyte.

The term "contacting" when it is used in relation to the composition such a protein (e.g., IL-3Rα antibody), a material, a sample or treatment means a direct or indirect interaction between the composition (e.g., IL-3Rα antibody) and other referenced substance. Specific examples of the direct interaction include bonding. Specific examples of the indirect interaction include a case in which the composition acts upon an intermediate molecule and this intermediate molecule then acts upon the referenced substance. Accordingly, for example, contacting a cell (e.g., lymphocyte) to IL-3Rα antibody includes to allow the antibody to bind to the cell (e.g., through binding to IL-3Rα) or to allow the antibody to act on an intermediate substance, followed by the action of this intermediate substance upon the cell.

The terms "assaying" and "measuring" and grammatical variations thereof are synonymously used in the specification and mean either of qualitative measurement and quantitative measurement or both of qualitative measurement and quantitative measurement. When these terms are used in relation to binding, they include any means of evaluating relative amount, affinity or specificity of binding including various methods which are described in the specification and conventionally known in the technical field. For example, binding of the IL-3Rα antibody with IL-3Rα can be assayed or measured by a flow cytometry assay.

(Production of Antibody)

The invention also provides a method for producing a human IL-3Rα antibody having cytotoxicity for IL-3Rα positive cells. In an embodiment, the method comprises administering a human IL-3Rα extracellular region conjugated with a human IL-3Rα recombinant protein or an IL-3Rα gene introduced cell into animals capable of expressing human immunoglobulin (e.g., transgenic mice or transgenic cattle); screening the animal for expression of a human IL-3Rα antibody; selecting the animal producing the human IL-3Rα antibody; and isolating the antibody from the selected animal.

The IL-3Rα protein suitable for the antibody production can be produced by any one of various standard protein purification and recombinant expression techniques. For example, the IL-3Rα sequence can be prepared by standard peptide synthesis techniques such as a solid phase synthesis. In order to facilitate purification of the expressed or synthesized protein, a portion of the protein may contain an amino acid sequence such as a FLAG tag, a T7 tag, a polyhistidine sequence or the like. The protein is expressed inside the cells and can be purified. The protein can be expressed by a recombination method as a part of a further large protein (e.g., a fusion or chimeric product). The embodiment of the IL-3Rα suitable for generating immune response includes IL-3Rα subsequences such as an immunogenicity fragment. Further embodiment of IL-3Rα includes an IL-3Rα expressing cell, an IL-3Rα containing preparation or cell extract or fraction and a partially purified IL-3Rα.

The method for preparing polyclonal antibody and monoclonal antibody is conventionally known in the technical field. For example, IL-3Rα or its immunogenicity fragment used for immunizing an animal by optionally conjugating with a carrier such as keyhole limpet hemocyanin (KLH) or ovalbumin (e.g., BSA) or mixing with an adjuvant such as complete Freund's adjuvant or incomplete Freund's adjuvant. By isolating a spleen cell derived from an immunized animal which responds to IL-3Rα, it can be fused with myeloma cell using hybridoma techniques. The monoclonal antibodies produced by hybridomas can be screened for reactivity with IL-3Rα or immunogenicity fragment thereof.

The animal which can be immunized includes the primates, mouse, rat, rabbit, goat, sheep, cattle and guinea pig. The initial and any optionally subsequent immunization may be by intravenous route, intraperitoneal route, intramuscular route or subcutaneous route. Further, in order to increase immune response, the antigen can be conjugated with other protein such as keyhole limpet hemocyanin (KLH), thyroglobulin and tetanus toxoid, or can be mixed with an adjuvant such as complete Freund's adjuvant, incomplete Freund's adjuvant and the like. The initial and any optionally subsequence immunization may be through intraperitoneal route, intramuscular route, intraocular route or subcutaneous route. The immunization may be at the same concentration or different concentration of an IL-3Rα preparation or at regular or irregular intervals.

The animal includes those which are genetically modified to include human gene loci, and a human antibody can be prepared using the same. Examples of the transgenic animals with one or more human immunoglobulin genes, are described for example in U.S. Pat. No. 5,939,598, WO02/43478 and WO02/092812. Using conventional hybridoma technique, an spleen cells which are isolated from immunized mouse having high responders to the antigen and are fused with myeloma cell. A monoclonal antibody which binds to IL-3Rα can be obtained.

The method for producing a human polyclonal antibody and a human monoclonal antibody is further described (see, such as Kuroiwa et al, *Nat. Biotechnol.* 20:889 (2002); WO98/24893; WO92/01047; WO96/34096; WO96/33735; U.S. Pat. Nos. 5,413,923; 5,625,126; 5,633,425; 5,569,825; 5,661,016; 5,545,806; 5,814,318; 5,885,793; 5,916,771; and 5,939,598).

The term "human" when it is used in reference to an antibody means that amino acid sequence of the antibody is completely the human amino acid sequence, namely is human heavy chain and human light chain variable regions and human constant region. Accordingly, all of the amino acids are human amino acids or present in the human antibody. An antibody which is a non-human antibody can be made into a complete human antibody by substituting the non-human amino acid residues with the amino acid residues which are present in the human antibody. The amino acid residues which are present in the human antibody, CDR region map and human antibody consensus residues are well known in the technical field (see e.g., Kabat, *Sequences of Proteins of Immunological Interest*, 4$^{th}$ edition, US Department of Health and Human Services, Public Health Service (1987); Chothia and Lesk (1987)). A consensus sequence of human VH subgroup III based on the investigation carried out using 22 known human VH III sequences as the object and a consensus sequence of human VL κ chain subgroup I based on the investigation carried out using 30 known human κ chain I sequences as the object are described in Padlan, *Mol. Immunol.*, 31: 169 (1994) and Padlan, *Mol. Immunol.*, 28: 489 (1991). Accordingly, the human antibody includes an antibody in which one or more amino acid residues have been substituted with one or more amino acids existing in an optional other human antibody.

Examples of the anti-IL-3Rα antibody include antibodies prepared using a known method in the technical field, such as CDR-grafting (EP 239,400; WO91/09967; U.S. Pat. Nos.

5,225,539; 5,530,101; and 5,585,089), veneering, resurfacing (EP592,106; EP519,596; Padlan, *Molecular Immunol.* 28: 489 (1991); Studnicka et al., *Protein Engineering* 7: 805 (1994); Roguska et al., *Proc. Nat'l Acad. Sci. USA* 91: 969 (1994)) and chain shuffling (U.S. Pat. No. 5,565,332). In order to produce a humanized antibody, human consensus sequence (Padlan, *Mol. Immunol.* 31:169 (1994); and Padlan, *Mol. Immunol.* 28: 489 (1991)) has been used (Carter et al., *Proc. Natl. Acad. Sci. USA* 89: 4285 (1992); and Presta et al, *J. Immunol.* 151: 2623 (1993)).

The term "humanized" when it is used in relation to an antibody means that amino acid sequence of the antibody has one or more non-human amino acid residues (e.g., mouse, rat, goat, rabbit and the like) of complement determining region (CDR) which specifically binds to a desired antigen in an acceptor human immunoglobulin molecule and one or more human amino acid residues (amino acid residues which are flanked with CDR) in Fv framework region (FR). The antibody called "primatized" is within the scope of meaning of "humanized", except that amino acid residues of the acceptor human immunoglobulin molecule and framework region can be any primate amino acid residues (e.g., monkey, gibbon, gorilla, chimpanzee, orangutan, macaque monkey) in addition to any human residues. Human FR residues of immunoglobulin can be substituted with corresponding non-human residues. Accordingly, for example, in order to alter, generally to improve, antigen affinity or specificity, residues in the CDR or human framework region can be substituted with corresponding residues from the non-human CDR or framework region donor antibody. The humanized antibody can contain residues which cannot be found in the human antibody and donor CDR or framework sequence. For example, it can be predicted that FR substitution at a particular position which cannot be found in human antibody or donor non-human antibody can improve binding affinity or specific human antibody at this position. Antibody framework and CDR substitutions based on the molecular modeling are conventionally known in the technical field, for example by the modeling of interaction of CDR and framework residues to identify framework residues important for antigen binding and the sequence comparison for identifying unusual framework residues at the specific position (see e.g., U.S. Pat. No. 5,585,089; and Riechmann et al., Nature, 332:323 (1988)).

Chimeric antibodies are included in the IL-3Rα antibody. According to this specification, the term "chimeric" and the grammatical variations thereof when it is used in relation to antibodies mean that amino acid sequence of the antibody contains one or more portion which is derived from two or more different species, is obtained or isolated from two or more different species or is based on two or more different species. For example, a portion of the antibody can be human (e.g., constant region) and other portion of the antibody can be non-human (e.g., a mouse heavy chain or a mouse light variable region). Accordingly, an example of the chimeric antibody includes an antibody in which the different portion of the antibody is derived from a different species. Different from the humanized or primatized antibody, the chimeric antibody can have a sequence of different species in an arbitrary region of the antibody.

The method for producing a chimeric antibody is known in the technical field (such as Morrison, Science 229: 1202 (1985); Oi et al., *BioTechniques* 4: 214 (1986); Gillies et al., *J. Immunol. Methods* 125: 191 (1989); U.S. Pat. Nos. 5,807,715; 4,816,567; and 4,816,397). For example, in Munro, *Nature* 312: 597 (1984); Neuberger et al., *Nature* 312: 604 (1984); Sharon et al., *Nature* 309: 364 (1984); Morrison et al., *Proc. Nat'l. Acad. Sci. USA* 81: 6851 (1984); Boulianne et al., *Nature* 312: 643 (1984); Capon et al, Nature 337: 525 (1989); and Traunecker et al., *Nature* 339: 68 (1989), a chimeric antibody in which a variable region of antibody derived from one species is replaced by a variable region of antibody derived from another species.

In addition, the anti-IL-3Rα antibody can be prepared by hybridoma technique, recombinant technique, and phage display technique, and a combination thereof (see U.S. Pat. Nos. 4,902,614, 4,543,439, and 4,411,993; and also see *Monoclonal Antibodies. Hybridomas: A New Dimension in Biological Analyses*, Plenum Press, Kennett, McKean, and Bechtol et al, 1980, and Harlow et al., *Antibodies: A Laboratory Manual*, Cold Spring Harbor Laboratory Press, the second edition, 1988).

The human anti-human IL-3Rα antibody of the invention was produced using chromosome-transferred mice (KM mice (trademark)) immunized with various forms of soluble form of recombinant human IL-3Rα proteins or cell lines expressing IL-3Rα (WO02/43478, WO02/092812, and Ishida et al., *IBC's 11th Antibody Engineering Meeting*, Abstract (2000)). Since the human anti-human IL-3Rα antibody detectably stains not a non-transformed parent cell line but a human IL-3Rα stable transfectant cell line, such as Jurkat-IL-3Rα cell and L929-IL-3Rα cell, the antibody specifically is shown to bind to human IL-3Rα.

The antibody of the invention can have κ light chain sequence or λ light chain sequence, full length of either one of them as present in naturally existing antibody, a mixture thereof (namely a fusion product of κ chain sequence and λ chain sequence) and subsequences/fragments thereof. The naturally presenting antibody molecules contain two κ light chains or two λ light chains.

The invention provides a method for preparing an antibody which specifically binds to IL-3Rα. In a specific embodiment, the method for preparing IL-3Rα antibody comprises administering human IL-3Rα, a subsequence thereof or a fragment thereof (e.g., IL-3Rα extracellular region), conjugated with a human Fc recombinant protein if necessary, to animals which can express human immunoglobulin (e.g., transgenic mice or transgenic cattle), screening the animals for their expression of human IL-3Rα antibody, selecting an animal which produces human IL-3Rα antibody and isolating the antibody from the selected animal. In an embodiment, whether or not the human IL-3Rα antibody has an IL-3Rα antagonist or agonist activity is judged by this method.

The effector activity means an antibody-dependent activity induced via Fc region of antibody, and such as antibody-dependent cellular cytotoxicity (ADCC activity), complement-dependent cytotoxicity (CDC activity), antibody-dependent phagocytosis (ADP activity) by phagocytes such as macrophage and dendritic cell, and the like, are known.

As a method for controlling effector activity of the anti-IL-3Rα monoclonal antibody of the invention, examples include a method which controls the amount of the fucose (also called core fucose) which is bound to N-acetylglucosamine (GleNAc) through α-1,6 bond in a reducing end of a complex-type N-linked sugar chain which is bound to asparagine (Asn) at position 297 of an Fc region of an antibody (WO2005/035586, WO2002/31140, and WO00/61739), a method in which is controlled by modifying amino acid residues of Fc region of the antibody, and the like. The effector activity can be controlled by applying any one of these methods to the anti-IL-3Rα monoclonal antibody of the invention.

By controlling the content of the core fucose of complex-type N-linked sugar chain of Fc of the antibody, effector activity of the antibody can be increased or decreased. As a method for reducing the content of the fucose which binds to the complex-type N-linked sugar chain which is bound to Fc of the antibody, defucosylation (defucosylated or non-fucosylated) can be mentioned. The defucosylation is to express an antibody using CHO cell from which α1,6-fucosyltransferase gene is deleted, and an antibody to which fucose is not bound can be obtained. The antibody to which fucose is not bound has high ADCC activity. On the other hand, as a method for increasing the content of the fucose which binds to the complex-type N-linked sugar chain to which Fc of the antibody is bound, the antibody to which fucose is bound can be obtained by expressing the antibody using a host cell in which α1,6-fucosyltransferase gene is introduced. The antibody to which fucose is bound has the ADCC activity lower than that of the antibody to which fucose is not bound.

In addition, ADCC activity and CDC activity can be increased or decreased by modifying amino acid residues of the Fc region of the antibody. For example, CDC activity of the antibody can be increased by using the amino acid sequence of the Fc region described in US 2007/0148165. Also, ADCC activity or CDC activity can be increased or decreased by carrying out the amino acid modification described in U.S. Pat. Nos. 6,737,056, 7,297,775 and 7,317,091. Further, an antibody in which effector activity of the antibody is controlled can be obtained by using the above-mentioned methods in combination in one antibody.

According to the invention, the nucleotide sequence of the invention such as of a vector and the like is further provided. In an embodiment, the vector comprises a nucleic acid sequence encoding an IL-3Rα antibody or a subsequence or fragment thereof.

The nucleic acid can have various lengths. The length of the nucleic acid encoding the IL-3Rα antibody of the present invention or the subsequence thereof is generally about 100 to 600 nucleotides, or any numerical value or range within encompassing such lengths the above described range; 100 to 150, 150 to 200, 200 to 250, 250 to 300, 300 to 350, 350 to 400, 400 to 450, 450 to 500, 500 to 550 or 550 to 600 nucleotide length, or any numerical value or range or value within or encompassing such length the above described range. Examples of the length of nucleic acid encoding the IL-3Rα antibody of the present invention or the subsequence thereof include generally 10 to 20, 20 to 30, 30 to 50, 50 to 100, 100 to 150, 150 to 200, 200 to 250, 250 to 300, 300 to 400, 400 to 500, 500 to 600 nucleotides and any numerical value or range within or encompassing such length.

The terms "nucleic acid" and "polynucleotide" means at least two or more ribo- or deoxy-ribo nucleic acid base pairs (nucleotide) linked which are through a phosphoester bond or equivalent. The nucleic acid includes polynucleotide and polynucleoside. The nucleic acid includes a single molecule, a double molecule, a triple molecule, a circular molecule or a linear molecule. Examples of the nucleic acid include RNA, DNA, cDNA, a genomic nucleic acid, a naturally existing nucleic acid and a non-natural nucleic acid such as a synthetic nucleic acid, but are not limited. Short nucleic acids and polynucleotides (e.g., 10 to 20, 20 to 30, 30 to 50, 50 to 100 nucleotides) are commonly called "oligonucleotides" or "probes" of single-stranded or double-stranded DNA.

Nucleic acid can be prepared using various standard cloning techniques and chemical synthesis techniques. Examples of the techniques include but are not limited to, nucleic acid amplification such as polymerase chain reaction (PCR), with genomic DNA or cDNA targets using primers (e.g., a degenerate primer mixture) which can be annealed with an antibody encoding sequence. In addition, nucleic acid can also be prepared by chemical synthesis (e.g., solid phase phosphoamidite synthesis) or transcription from a gene. Thereafter, the prepared sequence can be expressed by a cell (e.g., a host cell such as yeast, bacteria or eukaryote (an animal or mammal cell or in a plant)) after the sequence cloned into a plasmid and then amplified, or the sequence is translated in vitro.

A vector is a vehicle which can be manipulated by insertion or incorporation of nucleic acid. Examples of the vector include a plasmid vector, a virus vector, a prokaryote (bacterium) vector and a eukaryote (plant, fungi, mammals) vector. The vector can be used for in vitro or in vivo expression of nucleic acid. Such a vector is called "expression vector" and is useful for the transfer of nucleic acid including a nucleic acid which encodes an IL-3Rα antibody or its subsequence or fragment and the expression of an encoded protein by in vitro (e.g., in a solution or on solid phase), by a cell or by in vivo in a subject.

In addition, the vector can also be used for manipulation of nucleic acids. For genetic manipulation, an inserted nucleic acid can be transcribed or translated using a "cloning vector" in vitro (e.g., in a solution or on solid phase), in a cell or in vivo in a subject.

In general, the vector contains an origin of replication for amplification in a cell in vitro or in vivo. Control elements such as an expression control element present in the vector can be included in order to facilitate transcription and translation, if necessary.

A vector can include a selection marker. The "selection marker" is a gene which allows for the selection of a cell containing the gene. "Positive selection" means a process for selecting a cell containing the selection marker due to a positive selection. Drug resistance is an example of the positive selection marker, and a cell containing the marker will survive in culture medium containing the drug and a cell which does not contain the marker will die. Examples of the selection marker include drug resistance genes such as neo which provides resistance to G418; hygr which provides resistance to hygromycin; puro which provides resistance to puromycin, and the like. Other positive selection maker includes genes which enable identification or screening of a cell containing the marker. Examples of these genes include a fluorescent protein (GFP and GFP-like chromophore, luciferase) gene, lacZ gene, alkaline phosphatase gene, and a surface marker such as CD8. "Negative selection" means a process for killing cells which contain negative selection markers by exposing to an appropriate negative selection agent. For example, a cell containing a herpes simplex virus thymidine kinase (HSV-tk) gene (Wigler et al., Cell, 11: 223 (1977)) is sensitive to a drug ganciclovir (GANC). Similarly, gpt gene makes a cell sensitive to 6-thioxantine.

The virus vector includes those which are based on retroviral (a lentivirus for infecting not only dividing cells but also non-dividing cells), foamy virus (U.S. Pat. Nos. 5,624,820, 5,693,508, 5,665,577, 6,013,516 and 5,674,703; WO 92/05266 and WO 92/14829), adenovirus (U.S. Pat. Nos. 5,700,470, 5,731,172 and 5,928,944), adeno-associated virus (AAV) (U.S. Pat. No. 5,604,090), a herpes simplex virus vector (U.S. Pat. No. 5,501,979), a cytomegalovirus (CMV) system vector (U.S. Pat. No. 5,561,063), reovirus, rotavirus genome, simian virus 40 (SV40) or papilloma virus (Cone et al., *Proc. Natl. Acad. Sci. USA,* 81:6349 (1984); *Eukaryotic Viral Vectors*, Cold Spring Harbor Laboratory, edited by Gluzman, 1982; Sarver et al., *Mol. Cell. Biol.,* 1: 486 (1981); U.S. Pat. No. 5,719,054). Adenovirus efficiently infects a slowly replicating and/or terminally differentiated cell, and can be used to target the slowly replicating cell and/or terminally differentiated cell. Additional examples of virus vectors useful for expression include parbovirus, Norwalk virus, corona virus, paramyxo virus and rhabdo virus, toga virus (e.g., Sindobis virus and Semliki forest virus) and vesicular stomatitis virus (VSV).

A vector comprising a nucleotide acid can be expressed when the nucleic acid is connected to expression elements so as to function. The term "connected so as to function" (operably linked) means that a physical or functional relation between the elements referred to that permit them to operate in their intended fashion. Accordingly, the nucleic acid "operably linked" to an expression control element means that the control element modulates nucleic acid transcription and, as appropriate, translation of the transcription product.

The "expression control element" or "expression control sequence" is a polynucleotide which influences upon expression of an operably linked nucleic acid. Promoters and enhancers are non-limiting specific examples of expression controlling elements and sequences. The "promoter" is a cis-acting DNA regulatory region which can initiate transcription of downstream (3' direction) nucleic acid sequence. A nucleotide which accelerates transcription initiation is included in the promoter sequence. The enhancer also regulates nucleic acid expression but acts at a distance from the transcription initiation site of the nucleic acid to which it is operably linked. When the enhancer is present in either the 5' or 3' end of the nucleic acid as well as within the nucleic acid (e.g., intron or coding sequence), the enhancer further functions. Additional examples of the expression control element include a leader sequence and a fusion partner sequence, an internal ribosome entry site (IBES) element for preparing multigene, or polycistronic message, splicing signal of intron, maintenance of correct reading frame of gene to enable inframe translation of mRNA, polyadenylation signal which produces proper polyadenylation of the transcription product of interest, and stop codons.

Examples the expression control element include a "constitutional" element in which transcription of an operably linked nucleic acid occurs without the presence of signals or stimulus. The expression control element which confers expression in response to the signal or stimulus and increase or decrease expression of the operably linked nucleic acid is "adjustable". The adjustable element which increases expression of the operably linked nucleic acid in response to a signal or stimulus is called "inducible element". The adjustable element which decreases expression of the operably linked nucleic acid in response to a signal or stimulus is called "repressor element" (namely, the signal decreases the expression; and the expression increases when the signal is removed or not present).

Examples of the constitutional promoter for bacterial expression include an inducing promoter, such as T7 and pL, plac, ptrp and ptac (ptrp-lac hybrid promoter) of bacteriophage λ and the like. For insect cell system, a constitutional or an inducible promoter (e.g., ecdysone) can be used. The constitutional promoter for yeast include an inducing promoter such as ADH, LEU2, GAL and the like (e.g., see Ausubel et al., In: *Current Protocols in Molecular Biology*, Vol. 2, Chapter 13, Greene Publish. Assoc. & Wiley Interscience edition, 1988; Grant et al., In: *Methods in Enzymology,* 153: 516-544 (1987) Wu & Grossman, 1987, Acad. Press, N.Y.; Glover, *DNA Cloning*, Vol. 11, Chapter 3, IRL Press, Wash., D.C., 1986; Bitter, In: *Methods in Enzymology,* 152: 673-684 (1987), edited by Berger & Kimmel, Acad. Press, N.Y.; and Strathern et al., *The Molecular Biology of the Yeast Saccharomyces*, edited by Cold Spring Harbor Press, Vol. 1 and Vol. 11 (1982)).

For the expression in mammals, a constitutional promoter derived from a virus or other origin can be used. For example, inducible promoters derived from CMV, SV40, or a viral long terminal repeated sequence (LTR), or mammal cell genome (e.g., metallothionein IIA promoter; heat shock promoter, steroid/thyroid hormone/retinoic acid responding element) or mammal virus (e.g., adenovirus late promoter; mouse breast cancer virus LTR) can be used.

Examples of the expression control element include an element which is active in a specific tissue or cell types, and such an element is called "tissue specific expression control element". In general, the tissue specific expression control element is more active in specific cells or tissue types, and this is because this tissue specific expression control element is recognized by a transcription activating protein which is active in the specific cell or tissue types or by other transcription factor, as compared to other cells or tissue types. Non-limiting specific examples of such an expression control element are hexokinase II, COX-2, α-fetoprotein, carcinoembryonic antigen, DE3/MUC1, prostate specific antigen, C-erB2/neu, glucose-dependent insulin secretion stimulatory polypeptide (GIP), telomerase reverse transcriptase and a promoter such as hypoxia-responsive promoter.

According to the invention, a host cell transformed or transfected with IL-3Rα nucleic acid or vector of the invention is provided. Examples of the host cells, but are not limited to, include prokaryotic cell and eukaryotic cell, such as, bacteria, fungi (yeast), and cells of plants, insects and animals (e.g., mammals such as primates, human and the like). Non-limiting examples of transformed cell include a bacteria transformed with a recombinant bacteriophage nucleic acid, a plasmid nucleic acid or cosmid nucleic acid expression vector; a yeast transformed with a recombinant yeast expression vector; a plant cell infected with a recombinant virus expression vector (e.g., cauliflower mosaic virus, CaMV; tobacco mosaic virus, TMV) or transformed with a recombinant plasmid expression vector (e.g., Ti plasmid); an incest cell infected with a recombinant virus expression vector (e.g., baculovirus); and an animal cell infected with a recombinant virus expression vector (e.g., retrovirus, adenovirus, vaccinia virus) or a transformed animal cell manipulated for stable expression. CHO cell is a non-limiting example of a mammal host cell which expresses an IL-3Rα antibody and its subsequence thereof and fragment. The host cell may be a plurality or population of cells from a primary cell-separated line, an isolated secondary cell or subcultured cell, or an established cell line or immortalized cell culture.

The term "be transformed" or be transfected" when it is used in reference to a cell (e.g., host cell) or an organism means a change of gene in a cell after incorporation of an exogenous molecule, such as a protein or a nucleic acid (e.g., transgene), into the cell. Accordingly, the "transfected" or "transformed" cell is a cell into which the exogenous molecule is introduced by the hand of man by, for example, by recombinant DNA techniques or a progeny thereof.

The nucleic acid or protein can be transfected or transformed (expressed) in the cell or a progeny thereof stably or temporarily. The introduced protein can be expressed by growing the cell, or transcribing the nucleic acid. Since there is a possibility that a mutation occurs during replication, there is a case that a progeny of the transfected or transformed cell is not identical to the parent cell.

In general, a vector is used in the cell transfection or transformation. The vector can be included in a viral particle or vesicle and can be optionally directed demands to a specific cell types by including a protein on the particle or vesicle surface which binds to a target cell ligand or receptor. Accordingly, a cell can be used as a target by preparing the viral particle or vesicle itself or the viral surface protein, for the purpose of an in vitro, ex vivo or in vivo transfection or transformation. Accordingly, the vector includes in vitro, in vivo and ex vivo delivering techniques of viral and non-viral vectors into a cell, tissue or organ.

In addition, introduction of a nucleic acid into a target cell (e.g., a host cell) can also be carried out by a method conventionally known in the technical field, such as osmotic shock (e.g., calcium phosphate), electroporation, microinjection, cell fusion and the like. The introduction of nucleic acid and polypeptide in vitro, ex vivo and in vivo can also be carried out using other techniques. For example, a polymer substance such as polyester, poyamic acid, hydrogel, polyvinyl pyrrolidone, ethylene-vinyl acetate, methyl cellulose, carboxymethylcellulose, protamine sulfate, or lactide/glycolide copolymer, polylactide/glycolide copolymer, or ethylene vinyl acetate copolymer and the like. The nucleic acid can be enclosed in a hydroxymethyl cellulose or gelatin-microcapsule, or a microcapsule prepared using poly(methyl methacrylate microcapsule, or in a colloid system, respectively, by a coacervation technique or by interfacial polymerization. The colloid dispersion system includes a system based on a polymer complex, nanocapsule, microsphere, beads and lipid (oil-in-water type emulsion, micelle, mixed micelle, liposome and the like).

The liposome for introducing various compositions into cells is conventionally known in the technical field, and for example, phosphatidylcholine, phosphatidylserine, lipofectin and DOTAP are included therein (e.g., U.S. Pat. Nos. 4,844,904, 5,000,959, 4,863,740 and 4,975,282; and GIBCO-BRL, Gaithersburg, Md.). piperazine based amphilic cationic lipids which is useful in gene therapy (see e.g., U.S. Pat. No. 5,861,397) are also known. A cationic lipid system is also known (see e.g., U.S. Pat. No. 5,459,127). In this specification, the polymer substance, microcapsule and colloid dispersion system (loposome and the like) are collectively called as "vesicle".

In addition, examples of the suitable techniques which can be used in the method for producing an antibody are affinity purification, non-modified gel purification, HPLC or RP-HPLC, size exclusion, purification by protein A column and an optional combination of these techniques. An IL-3Rα antibody isotype can be determined using ELISA assay, and for example, human Ig can be identified using mouse Ig absorbed anti-human Ig.

Binding affinity can be determined by association (Ka) and dissociation (Kd) rates. The equilibrium affinity constant KD is the ratio of Ka/Kd. The association (Ka) and dissociation (Kd) rates can be measured using surface plasmon resonance (SPR) (Rich and Myszka, *Curr. Opin. Biotechnol.*, 11: 54 (2000): *Englebienne, Analyst.*, 123: 1599 (1998)). Instrumentation and methods for real time detection and monitoring of association rate are conventionally known and commercially available (BiaCore 2000, Biacore AB, Upsala, Sweden; and Malmqvist, *Biochem. Soc. Trans.*, 27:335 (1999)). The KD value can be defined as the IL-3Rα antibody concentration required to saturate one half of the binding site (50%) on IL-3Rα.

(Crossing Property in Primates)

Currently, although as many as 500 therapeutic antibodies are being developed in the world, it is said that human antibodies have a high possibility to be able to avoid problems of immunogenicity. However, on the other hand, there are many cases in which drug efficacy of human antibodies are not exhibited at all in rodents. In that case, there are many cases in that primates have to be used in toxicity tests, and furthermore the reactivity is found only in chimpanzee is not rare in many cases. When the pharmacological reaction can be found only in chimpanzee, the toxicity test is further significantly constrained. In the first place, facilities where chimpanzee experiments can be carried out are considerably limited, individuals are infected with HIV in many cases and there are also problems of labor hygiene of workers involved in the experiments. In addition, regarding chimpanzee, there are large limitations that anatomy test after final drug administration cannot be carried out and of reproductive toxicity test is also impossible to carry out and the like. Accordingly, the ability to verify drug efficacy in monkey (*Macaca fascicularis* and/or *Macaca mulatta*) is useful from the viewpoint of advancing toxicity tests which are essential for developing pharmaceuticals.

Regarding the method for confirming monkey crossreactivity with monkey, it can be confirmed by a conventionally known method such as immunochemical tissue staining method, solid phase enzyme immunoassay (hereinafter, "ELISA"), flow cytometry (FCM) and the like.

(Pharmaceutical Composition)

Antibodies can be included in a pharmaceutical composition. In an embodiment, an antibody comprises a pharmaceutically acceptable carrier, a stabilizer or a filler and is prepared in the form of aqueous solution or as a freeze-dried preparation. Typically, an appropriate amount of a pharmaceutically acceptable salt is used for isotonicity of the pharmaceutical preparation. Examples of the acceptable carrier, stabilizer or filler include a buffer solution such as phosphate, citrate and other organic acid and the like; a low molecular weight (less than 10 in the number of residues) polypeptide; a protein such as serum albumin, gelatin, immunoglobulin and the like; a hydrophilic polymer such as polyvinyl pyrrolidone; an amino acid such as glycine, glutamine, asparagine, histidine, arginine, lysine and the like; a monosaccharide, disaccharides and other carbohydrates such as glucose, mannose, dextrin and the like; a chelating agent such as EDTA and the like; saccharides such as sucrose, mannitol, trehalose, sorbitol and the like; a salt forming counter ion such as sodium and the like; a metal complex (e.g., Zn-protein compflex); an antiseptic (octadecyl dimethylbenzylammonium chloride; hexamethonium chloride; banzalconium chloride; benzethonium chloride; phenol, butyl or benzyl alcohol; alkyl parabens such as methyl or propyl paraben; catechol; resorcinol; cyclohexanol; 3-pentanol; and m-cresol); and/or a nonionic surfactant such as TWEEN™, PLURONICS™, polyethylene glycol (PEG) and the like.

(Therapeutic Use of Antitumor Substance which Targets IL-3Rα Expression Cells)

Examples of the diseases for which the therapeutic use is examined, but are not limited thereto, include the diseases which can be considered to treat by binding or targeting IL-3Rα-expressing blood tumor cells (AML cell, CML cell, MDS cell, ALL cell, CLL cell, multiple myeloma cell and the like), mastocyte, basophile, helper T cell (e.g., Th1 cell, Th17 cell), regulatory T cell (e.g., CD4 positive CD25 positive cell), antigen presenting cell (e.g., dendritic cell, monocyte•macrophage and related cells (hepatic stellate cell, osteoclast, microglia, intraepidermal macrophage, dust cell (alveolar phagocyte) and the like)).

Examples of the disease for which therapeutic use is examined include a blood disease in which expression of IL-3Rα is found in bone marrow or peripheral blood. Specific example may include acute myeloid leukemia (AML). Based on the FAB classification (French-American-British criteria) which can determine which stage of the cell among the cells in the course of differentiating into various blood cells from the hematopoietic stem cell caused tumorigenic transformation, the acute myeloid leukemia is classified into disease types of M0 (micro-differentiation type myeloblastic leukemia), M1 (undifferentiated myeloblastic leukemia), M2 (differentiated myeloblastic leukemia), M3 (acute promyelocytic leukemia), M4 (myelomonocytic leukemia), M5 (monocytic leukemia), M6 (erythroleukemia), M7 (megakaryocytic leukemia) and subtypes thereof. In addition, further examples of diseases include acute lymphocytic leukemia, atypical leukemia, chronic lymphocytic leukemia, adult T cell leukemia, NK/T cell lymphoma, granular lymphocytosis (LGL leukemia), polycythemia vera, essential thrombocythemia, hypereosinophilic syndrome, Hodgkin lymphoma, non-Hodgkin lymphoma, follicular lymphoma, MALT lymphoma, mantle cell lymphoma, diffuse large B-cell lymphoma, Burkitt lymphoma, lymphoblastic lymphoma and Catsleman disease.

The method of the invention which comprises administration or delivery of an IL-3Rα antibody and an anti-tumor substance which targets an IL-3Rα expression cell can be carried out by any acceptable method. In a specified embodiment, these are administered to a subject, locally, regionally or systemically.

In addition, regarding the IL-3Rα antibody, the antitumor substance which targets IL-3Rα expression cell for treating the above-mentioned diseases can also be considered to combine with other therapeutic agent suitable for the same disease (typically a chemotherapeutic agent) or be administered in combination with radiotherapy. Examples of the suitable other therapeutic agent include a chemotherapeutic agent such as cytarabine (Ara-C), an anthracycline system antitumor agent (typically, daunorubicin (DNR), idarubicin (IDA)) and the like, a differentiation induction therapeutic agent such as all-trans retinoic acid (ATRA), arsenious acid, Am80 (tamibarotene), gemtuzumab-ozogamicin (ozogamicin conjugate anti-CD33 antibody), topotecan, fludarabine, cyclosporine, mitoxantrone (MIT), interferon and imatinib, but are not limited thereto, and also include a combination with a therapeutic method considered to be clinically effective.

Mammals (e.g., human) are included in the subject which can be treated by the invention. In a specified embodiment, it is a subject who is a candidate of blood tumor or a subject who received treatment of the blood tumor, a subject having a possibility causing IL-3Rα-mediated cellular response or a subject who received treatment of the IL-3Rα-mediated cellular response, a subject who is a candidate of a myelocytic malignant tumor or a subject who received treatment of the myelocytic malignant tumor or a subject who is a candidate of acute myeloid leukemia or a subject who received treatment of the acute myeloid leukemia.

According to this specification, the terms "treat", "treating", "treatment" and the grammatical variations thereof mean a protocol, a planning, a process or an improving method which is carried out on each subject who is desirable to obtain physiological effect or good outcome on the patient. Accordingly, the method of the invention includes a treatment and a treating method which produce measurable improvement or beneficial effect, particularly on a disorder, a disease, pathology, a condition of a disease or a symptom of a given subject. The measurable improvement or profitable effect is objective or subjective, immoderate, transient or long-term improvement of any one of disorders, diseases, pathology, conditions of a disease or symptoms, or a reduction in onset, severity, duration or frequency of adverse symptom related to or caused by disorders, diseases, physiological conditions, pathology or state. According to the method of the invention, there is a possibility that its effect is not always exhibited immediately, but eventual improvement or beneficial effect is found a little later with the lapse of time, so that stabilization or amelioration in a give subject will occur.

Unless otherwise noted, all of the technical terms and scientific terms used in this specification have the same meanings of those which are generally evident for persons in the technical field to which the invention is related. Methods and materials similar or equivalent to those described in this specification can be used in the operations or examinations of the invention, but those which are described in this specification are suitable methods and materials.

EXAMPLES

Example 1

Preparation of Human, *Macaca fascicularis* or *Macaca mulatta* IL-3Rα Expression Cell (Molecular Cloning of IL-3Rα cDNA and Preparation of Expression Vector)

Human IL-3Rα cDNA was amplified from a blood cell-derived DNA (CLONTECH Human MTC Panel) by PCR using ExTaq (TAKARA BIO INC.). As a PCR device, GeneAmp PCR System 9700 (Applied Biosystems, hereinafter, the PCR device is the same in this specification) was used. Regarding the PCR, after a denaturation step at 94° C. for 5 minutes, a three step reaction at 94° C. 30 seconds-55° C. 30 seconds-72° C. 2 minutes was carried out 40 cycles and then a reaction at 99° C. for 30 seconds was carried out. The PCR primers used are as follows.

```
IL-3Rα_Fw:
                                         (SEQ ID NO: 3)
5'-CGGCAATTGCCACCATGGTCCTCCTTTGGCTCAC-3'

IL-3Rα_Re:
                                         (SEQ ID NO: 4)
5'-ATTGCGGCCGCTCAAGTTTTCTGCACGACCT-3'
```

The thus obtained PCR products were subjected to 0.8% agarose gel electrophoresis (135 V, 15 minutes, TAE buffer). DNA was visualized by ethidium bromide staining. A band at around 1.2 kb was cut out and extracted using JetSob (Genomed). The extracted DNA was digested with MfeI and NotI, mixed with pEGFP-N1 vector (Clontech) or pEF6/Myc-His vector which had been digested with EcoRI and Nod and ligated using TaKaRa Ligation Kit. Regarding the transformation, the ligation sample and a DH10B competent cell were mixed and spread on LB plate (containing kanamycin). Insert check of the pEGFP-N1 vector was carried out by colony direct PCR using LA Taq (Takara Shuzo Co., Ltd.). Regarding the PCR, after a denaturation step at 94° C. for 5 minutes, a three step reaction at 94° C. 30 seconds-55° C. 30 seconds-72° C. 2 minutes was carried out 40 cycles and then a reaction at 99° C. for 30 seconds was carried out. Regarding the primers used, IL-3Rα-Fw and IL-3Rα-Re were used.

The thus obtained PCR products were subjected to 0.8% agarose gel electrophoresis (135 V, 15 minutes, TAE buffer). DNA was visualized by ethidium bromide staining. Using a colony from which amplification at around 1.2 kb was obtained, nucleotide sequence was determined by a direct sequencing method. In the reaction of sequence samples, BigDye(R) Terminator v3.1 Cycle Sequencing Kit (Applied Biosystems) and GeneAmp PCR System 9700 (Applied Biosystems) were used (these were used in the all DNA sequence analyses in this specification). Regarding the primers, IL-3Rα-Fw, IL-3Rα-Re and the following primer were used.
IL-3Rα_seqF1: 5'-GTCTTCACTACAAAACGGAT-3' (SEQ ID NO:5)

ABI 3700XL DNA analyzer (Applied Biosystems) was used as the sequence analyzing device. A clone having the same sequence of the coding region of GenBank association number NP-002174.1 was selected and a plasmid DNA was extracted by a Miniprep method. The vector names were pEGFR-N1/hCD123 and pEF6/Myc-His/hCD123, respectively.

The sequence of the insert (MfeI to NotI) was as follows.

(SEQ ID NO: 6)
CAATTGCCACCATGGTCCTCCTTTGGCTCACGCTGCTCCTGATCGCCC

TGCCCTGTCTCCTGCAAACGAAGGAAGATCCAAACCCACCAATCACGA

ACCTAAGGATGAAAGCAAAGGCTCAGCAGTTGACCTGGGACCTTAACA

GAAATGTGACCGATATCGAGTGTGTTAAAGACGCCGACTATTCTATGC

CGGCAGTGAACAATAGCTATTGCCAGTTTGGAGCAATTTCCTTATGTG

AAGTGACCAACTACACCGTCCGAGTGGCCAACCCACCATTCTCCACGT

GGATCCTCTTCCCTGAGAACAGTGGGAAGCCTTGGGCAGGTGCGGAGA

ATCTGACCTGCTGGATTCATGACGTGGATTTCTTGAGCTGCAGCTGGG

CGGTAGGCCCGGGGGCCCCCGCGGACGTCCAGTACGACCTGTACTTGA

ACGTTGCCAACAGGCGTCAACAGTACGAGTGTCTTCACTACAAAACGG

ATGCTCAGGGAACACGTATCGGGTGTCGTTTCGATGACATCTCTCGAC

TCTCCAGCGGTTCTCAAAGTTCCCACATCCTGGTGCGGGCAGGAGCG

CAGCCTTCGGTATCCCCTGCACAGATAAGTTTGTCGTCTTTTCACAGA

TTGAGATATTAACTCCACCCAACATGACTGCAAAGTGTAATAAGACAC

ATTCCTTTATGCACTGGAAAATGAGAAGTCATTTCAATCGCAAATTTC

GCTATGAGCTTCAGATACAAAAGAATGCAGCCTGTAATCACAGAAC

AGGTCAGAGACAGAACCTCCTTCCAGCTACTCAATCCTGGAACGTACA

CAGTACAAATAAGAGCCCGGGAAAGAGTGTATGAATTCTTGAGCGCCT

GGAGCACCCCCCAGCGCTTCGAGTGCGACCAGGAGGAGGGCGCAAACA

CACGTGCCTGGCGGACGTCGCTGCTGATCGCGCTGGGGACGCTGCTGG

CCCTGGTCTGTGTCTTCGTGATCTGCAGAAGGTATCTGGTGATGCAGA

GACTCTTTCCCCGCATCCCTCACATGAAAGACCCCATCGGTGACAGCT

TCCAAAACGACAAGCTGGTGGTCTGGGAGGCGGGCAAAGCCGGCCTGG

AGGAGTGTCTGGTGACTGAAGTACAGGTCGTGCAGAAAACTTGAGCGG

CCGC

The *Macaca fascicularis* and *Macaca mulatta* cDNA samples were amplified from a *Macaca fascicularis* bone marrow-derived cDNA or Macaca mulatta bone marrow-derived cDNA by a PCR method using LA Taq (TAKARA BIO INC). GeneAmp PCR System 9700 (Applied Biosystems) was used as the PCR device. Regarding the PCR, after a denaturation step at 95° C. for 1 minute, a three step reaction at 95° C. 15 seconds-56° C. 15 seconds-72° C. 70 seconds was carried out 40 cycles and then a reaction at 72° C. for 2 minutes was carried out. Subsequences were obtained through BLAST retrieval for the public data base of *Macaca mulatta* genome (http://www.hgsc.bnm.tmc.edu/blast.hgsc), based on the hIL-3Rα cDNA sequence to design primers. The used primer sequences were as follows.

Rhe123Fw1:
(SEQ ID NO: 7)
CGGCAATTGCCACCATGACCCTCCTTTGGCTGACGCTG

Rhe123Rv1:
(SEQ ID NO: 8)
TATATTGCGGCCGCTCAAGTTTTCTCCACCACCTGCAC

The thus obtained PCR products were subjected to 0.8% agarose gel electrophoresis (135 V, 15 minutes, TAE buffer). DNA was visualized by ethidium bromide staining. A band at around 1.2 kb was cut out and the DNA was extracted using Gel Extraction Kit (QIAGEN). The thus extracted DNA was mixed with pGEM-T Easy vector (Promega) and ligated using TaKaRa Ligation Kit. Regarding the transformation, the ligation sample and a DH10B competent cell were mixed and spread on LB plate (containing ampicillin). Insert check of the pGEM-T Easy vector was carried out by colony direct PCR using LA Taq (Takara Shuzo Co., Ltd.). Regarding the PCR, after a denaturation step at 95° C. for 1 minute, a three step reaction at 95° C. 15 seconds-56° C. 15 seconds-72° C. 1 minute was carried out 35 cycles and then a reaction at 72° C. for 2 minutes was carried out. The following were used as the primers.

(SEQ ID NO: 9)
T7: TAATACGACTCACTATAGGG (SEQ ID NO: 10)
SP6: GATTTAGGTGACACTATAG

The thus obtained PCR products were subjected to 0.8% agarose gel electrophoresis (135 V, 15 minutes, TAE buffer). DNA was visualized by ethidium bromide staining. Using a colony from which amplification at around 1.2 kb was obtained, nucleotide sequence was determined by a direct sequencing method. As the PCR primers, T7 and SP6 were used. A clone showing no mutation by PCR was selected and its plasmid DNA was extracted by the Miniprep method. The thus obtained DNA was digested with MfeI and NotI, mixed with pEGFP-N1 vector (Clontech) which had been cleaved with EcoRI and NotI and ligated using TaKaRa Ligation Kit. Regarding the transformation, the ligation sample and a DH10B competent cell were mixed and spread on LB plate (containing kanamycin).

Insert check of the pEGFP-N1 vector was carried out by a colony direct PCR using La Taq (Takara Shuzo Co., Ltd.). Regarding the PCR, after a denaturation step at 94° C. for 5 minutes, a three step reaction at 94° C. 30 seconds-55° C. 30 seconds-72° C. 2 minutes was carried out 40 cycles and then a reaction at 99° C. for 30 seconds was carried out. Regarding the used PCR primers, Rhe123Fw1 and Rhe123Rv1 were used.

The thus obtained PCR products were subjected to 0.8% agarose gel electrophoresis (135 V, 15 minutes, TAE buffer). DNA was visualized by ethidium bromide staining. Using a colony from which amplification at around 1.2 kb was obtained, nucleotide sequence was determined by a direct sequencing method. BigDye(R) Terminator v3.1 Cycle Sequencing Kit (Applied Biosystems) and GeneAmp PCR System 9700 (Applied Biosystems) were used in the reaction of sequence sample (these were used in all of the DNA sequence analyses in this specification). As the primers, Rhe123Fw1 and Rhe123Rv1 were used. The vectors were named pEGFR-N1/cyCD123 and pEGFR-N1/rhCD123, respectively.

The sequence of the insert (MefI to NotI) of *Macaca fascicularis* IL-3Rα was as follows.

(SEQ ID NO: 11)
CAATTGCCACCATGACCCTCCTTTGGCTGACGCTGCTCCTGGTCGCCA

CGCCCTGTCTCCTGCAAACGAAGGAGGATCCAAATGCACCAATCAGGA

ATCTAAGGATGAAAGAAAAGGCTCAGCAGTTGATGTGGGACCTGAACA

GAAACGTGACCGACGTGGAGTGTATCAAAGGCACCGACTATTCTATGC

CGGCAATGAACAACAGCTATTGCCAGTTCGGAGCCATTTCCTTATGTG

AAGTGACCAACTACACCGTCCGAGTGGCCAGTCCCCGTTCTCCACGT

GGATCCTCTTCCCTGAGAACAGTGGGACGCCTCAGGCAGGCGCGGAGA

ATCTGACCTGCTGGGTTCATGACGTGGATTTCTTGAGCTGCAGCTGGG

TGGCAGGCCCGGCGGCCCCCGCTGACGTCCAGTACGACCTGTACTTGA

ACAATCCCAACAGCCACGAACAGTACAGGTGCCTTCACTACAAAACGG

ATGCTCGGGGAACACAGATCGGGTGTCGGTTCGATGACATCGCTCGAC

TCTCCCGCGGTTCTCAAAGTTCCCACATCCTGGTGAGGGGCAGGAGCG

CAGCCGTCAGTATCCCCTGCACAGATAAGTTTGTCTTCTTTTCACAGA

TTGAGAGATTAACTCCACCCAACATGACTGGAGAGTGTAATGAGACAC

ATTCCTTCATGCACTGGAAAATGAAAAGTCATTTCAATCGCAAATTCC

GCTATGAGCTTCGGATCCAAAAGAGAATGCAGCCTGTAAGGACAGAAC

AGGTCAGAGACACAACCTCCTTCCAGCTACCCAATCCTGGAACGTACA

CAGTGCAAATAAGAGCCCGGGAAACAGTGTATGAATTCTTGAGTGCCT

GGAGCACCCCCCAGCGCTTCGAGTGCGACCAGGAGGAGGGCGCGAGCT

CGCGTGCCTGGCGGACGTCGCTGCTGATCGCGCTGGGGACGCTGCTGG

CCTTGCTCTGTGTGTTCCTCATCTGCAGAAGGTATCTGGTGATGCAGA

GGCTGTTTCCCCGCATCCCACACATGAAAGACCCCATCGGTGACACCT

TCCAACAGGACAAGCTGGTGGTCTGGGAGGCGGGCAAAGCCGGCCTGG

AGGAGTGTCTGGTGTCTGAAGTGCAGGTGGTGGAGAAAACTTGAGCGG

CCGC

The sequence of the insert (MefI to NotI) of *Macaca mulatta* IL-3Rα was as follows.

(SEQ ID NO: 12)
CAATTGCCACCATGACCCTCCTTTGGCTGACGCTGCTCCTGGTCGCCA

CGCCCTGTCTCCTGCAAACCAAGGAGGATCCAAATGCACCAATCAGGA

ATCTAAGGATGAAAGAAAAGGCTCAGCAGTTGATGTGGGACCTGAACA

GAAACGTGACCGACGTGGAGTGTATCAAAGGCACCGACTATTCTATGC

CGGCAATGAACGACAGCTATTGCCAGTTCGGAGCCATTTCCTTATGTG

AAGTGACCAACTACACCGTCCGAGTGGCCAGTCCTCCGTTCTCCACGT

GGATCCTCTTCCCTGAGAACAGTGGGACGCCTCGGGCAGGCGCGGAGA

ATTTGACCTGCTGGGTTCATGACGTGGATTTCTTGAGCTGCAGCTGGG

TGGTAGGCCCGGCGGCCCCCGCTGACGTCCAGTACGACCTGTACTTGA

ACAATCCCAACAGCCACGAACAGTACAGGTGCCTTCGCTACAAAACGG

ATGCTCGGGGAACACAGATCGGGTGTCGGTTCGATGACATCGCTCGAC

TCTCCCGCGGTTCTCAAAGTTCCCACATCCTGGTGAGGGGCAGGAGCG

CAGCCGTCAGTATCCCCTGCACAGATAAGTTTGTCTTCTTTTCACAGA

TTGAGAGATTAACTCCACCCAACATGACTGGAGAGTGTAATGAGACAC

ATTCCTTCATGCACTGGAAAATGAAAAGTCATTTCAATCGCAAATTCC

ACTATGAGCTTCGGATCCAAAAGAGAATGCAGCCTGTAAGGACAGAAC

AGGTCAGAGACACAACCTCCTTCCAGCTACCCAATCCTGGAACGTACA

CAGTGCAAATAAGAGCCCGGGAAACAGTGTATGAATTCTTGAGTGCCT

GGAGCACCCCCCAGCGCTTCGAGTGCGACCAGGAGGAGGGCGCGAGCT

CGCGTGCCTGGCGGACGTCGCTGCTGATCGCGCTGGGGACGCTGCTGG

CCTTGCTCTGTGTGTTCCTCATCTGCAGAAGGTATCTGGTGATGCAGA

GGCTGTTTCCCCGCATCCCACACATGAAAGACCCCATCGGTGACACCT

TCCAACAGGACAAGCTGGTGGTCTGGGAGGCGGGCAAAGCCGGCCTGG

AGGAGTGTCTGGTGTCTGAAGTGCAGGTGGTGGAGAAAACTTGAGCGG

CCGC (Preparation of IL-3Rα Forced Expression Cell Line)

L929 cell (manufactured by ATCC) and Colon-26 cell (manufactured by ATCC) were infected with pEGFP-N1 vector/hCD123 or pEF6/Myc-His vector/hCD123 using electroporation (BTX). Specifically, 10 to 20 µg of DNA was mixed with one hundred thousand cells and allowed to react at 300 V and 950 µF. Regarding the cells, drug resistant cells were selected using neomycin (Calbiochem) for pEGFP-N1/hCD123 or blasticidin (Invitrogen) for pEF6/Myc-His/hCD123. Regarding the thus selected cells, a GFP-positive cell or a cell highly expressing IL-3Rα (CD123) was further selected by sorting using flow cytometry (FAC SVantage, FACSAria and the like, BD Biosciences) and named as L929/hCD123 and Colon-26/hCD123, respectively.

Regarding the preparation of *Macaca fascicularis* IL-3Rα and *Macaca mulatta* IL-3Rα forced expression cells, these were also prepared using L929 and Colon-26 in the same manner as the case of human IL-3Rα forced expression cell and named L929/cyCD123, Colon-26/cyCD123, L929/rhCD123 and Colon-26/rhCD123.

Example 2

Preparation of Soluble Form of IL-3Rα Extracellular Region (Preparation of Soluble Form of Human IL-3Rα Extracellular Region Expression Vector)

A cDNA encoding the extracellular region of human IL-3Rα was amplified by a PCR method, and FLAG tag was connected to its downstream. Specifically, the cDNA encoding the extracellular region of human IL-3Rα was amplified by PCR using pEF6/Myc-His/hCD123 plasmid DNA as the template and using Platinum Pfu polymerase (Invitrogen). Regarding the PCR, after a denaturation step at 96° C. for 2 minutes, a three step reaction at 96° C. 20 seconds-55° C. 30 seconds-68° C. 65 seconds was carried out 30 cycles. The primers used were IL-3Rα-Fw and the following primer.

hIL-3Rαsol-FLAG-NotI:
(SEQ ID NO: 13)
5'-ATTGCGGCCGCTCACTTATCGTCGTCATCCTTGTAGTCCCGCCAG

GCACGTGTGTTTG-3'

The thus obtained PCR products were subjected to 0.8% agarose gel electrophoresis (135 V, 15 minutes, TAE buffer). DNA was visualized by ethidium bromide staining. The DNA was extracted using JetSorb (Genomed). Thus purified DNA was digested with MfeI and NotI and again subjected to 0.8% agarose gel electrophoresis (135 V, 15 minutes, TAE buffer). A band of around 1.0 kb was cut out and the DNA was extracted using JetS orb (Genomed). The obtained DNA was mixed with a pTracer-CMV/Bsd vector, which had been cleaved using the same enzymes of the purified DNA, and ligated using TaKaRa Ligation Kit. Regarding the transformation, the ligation sample and a DH10B competent cell were mixed and spread on LB plate (containing ampicillin). Insert check was carried out by colony direct PCR using LA Taq (Takara Shuzo Co., Ltd.). Regarding the PCR, after a denaturation step at 95° C. for 1 minute, a three step reaction at 95° C. 15 seconds-56° C. 15 seconds-72° C. 40 seconds was carried out 35 cycles and then an elongation reaction at 72° C. for 2 minutes was carried out. The PCR primers used were IL-3Rα-Fw and IL-3Rαsol-FLAG-NotI.

The thus obtained PCR products were subjected to 0.8% agarose gel electrophoresis (135 V, 15 minutes, TAE buffer). DNA was visualized by ethidium bromide staining. A plasmid DNA was extracted by the Miniprep method from a colony in which amplification of around 1.0 kb was obtained. It was found by a DNA sequence analysis that the purified plasmid DNA has the sequence identical to the corresponding region of GenBank accession number NP-002174.1.

The sequence of the insert (MfeI to NotI) was as follows.

(SEQ ID NO: 14)
CAATTGCCACCATGGTCCTCCTTTGGCTCACGCTGCTCCTGATCGCCC

TGCCCTGTCTCCTGCAAACGAAGGAAGATCCAAACCCACCAATCACGA

ACCTAAGGATGAAAGCAAAGGCTCAGCAGTTGACCTGGGACCTTAACA

GAAATGTGACCGATATCGAGTGTGTTAAAGACGCCGACTATTCTATGC

CGGCAGTGAACAATAGCTATTGCCAGTTTGGAGCAATTTCCTTATGTG

AAGTGACCAACTACACCGTCCGAGTGGCCAACCCACCATTCTCCACGT

GGATCCTCTTCCCTGAGAACAGTGGGAAGCCTTGGGCAGGTGCGGAGA

ATCTGACCTGCTGGATTCATGACGTGGATTCTTGAGCTGCAGCTGGG

CGGTAGGCCCGGGGGCCCCGCGGACGTCCAGTACGACCTGTACTTGA

ACGTTGCCAACAGGCGTCAACAGTACGAGTGTCTTCACTACAAAACGG

ATGCTCAGGGAACACGTATCGGGTGTCGTTTCGATGACATCTCTCGAC

TCTCCAGCGGTTCTCAAAGTTCCCACATCCTGGTGCGGGCAGGAGCG

CAGCCTTCGGTATCCCCTGCACAGATAAGTTTGTCGTCTTTTCACAGA

TTGAGATATTAACTCCACCCAACATGACTGCAAAGTGTAATAAGACAC

ATTCCTTTATGCACTGGAAAATGAGAAGTCATTTCAATCGCAAATTTC

GCTATGAGCTTCAGATACAAAAGAATGCAGCCTGTAATCACAGAAC

AGGTCAGAGACAGAACCTCCTTCCAGCTACTCAATCCTGGAACGTACA

CAGTACAAATAAGAGCCGGGAAAGAGTGTATGAATTCTTGAGCGCCT

GGAGCACCCCCAGCGCTTCGAGTGCGACCAGGAGGAGGGCGCAAACA

CACGTGCCTGGCGGGACTACAAGGATGACGACGATAAGTGAGCGGCCG

C (Preparation of Soluble Form of Human IL-3Rα Protein)

Plasmid DNA of pTracer CMV expression vector containing soluble form of IL-3Rα sequence was purified using QIAGEN Plasmid Maxi Kit. A CHOras1 cell was used as a host cell for expression. The CHOras1 cell was cultured with shaking using SFM II medium (Invitrogen) (37° C., 5% $CO_2$).

A PEI method was used in the gene introduction. Polyethylenimine, Linear, MW 25,000 (Polysciences) was weighed and dissolved in PBS while adjusting to around pH 7.0 with HCl (1 g/l). The obtained solution was stirred for 1 hour and then sterilized by filtering through a membrane filter having a pore size of 0.22 μm, MILLEX-GV (Millipore). Then, 1 mg of the purified plasmid DNA was mixed with 20 ml of Opti-Pro SFM (Invitrogen) to obtain Solution A. Solution B was prepared by mixing 2.5 ml of PEI solution (1 g/l) with 20 ml of Opti-Pro SFM (Invitrogen). After solution A and Solution B were mixed, and then allowed to stand still for 10 minutes, the obtained solution was added to CHOras1 cells (1,000,000 cells per 1 ml). After six days, the cell supernatant was recovered and used for the protein purification.

Purification of the soluble form of human IL-3Rα protein was carried out by the following method. A culture supernatant containing soluble form of IL-3Rα protein was recovered by centrifugation 6 days after the gene introduction and passed through a filter. The obtained solution was diluted 5 times with Tris buffered saline (TBS), an Anti-FLAG column was prepared using anti-FLAG M2 Agarose Affinity Gel (Sigma) and the solution was applied thereto using HiLoad Pump P-50 (Pharmacia Biotech). Elution was carried out using FLAG peptide (Sigma) and in accordance with the manual. The eluate was fractioned into several fractions, each fraction was subjected to SDS-PAGE (MultiGel II Mini 10/20% gradient gel; Cosmo Bio Co., Ltd.) under a reducing condition, and then silver staining and Western blotting were carried out. A silver staining reagent "Daiichi" (Daiichi Pure Chemicals Co., Ltd.) was used for the silver staining. Anti-FLAG M2 antibody (Sigma) and an alkaline phosphatase-labeled rabbit anti-mouse immunoglobulin antibody were used for the Western blotting. A fraction in which the protein of interest was found was concentrated using Amicon Ultra-4 10K (Millipore), and gel filtration chromatography was carried out using Superdex 200 gp (GE Healthcare). After fractionation, each fraction was subjected to SDS-PAGE (Multi-Gel II Mini 10/20% gradient gel; Cosmo Bio Co., Ltd.) under a reducing condition, and then silver staining and Western blotting were carried out. A silver staining reagent "Daiichi" (Daiichi Pure Chemicals Co., Ltd.) was used in the silver staining. Anti-FLAG M2 antibody (Sigma) and an alkaline phosphatase-labeled rabbit anti-mouse immunoglobulin antibody were used in the Western blotting. A fraction in which the protein of interest was found was concentrated using Amicon Ultra-4 10K (Millipore) and washed with PBS. By carrying out sterilization by filtration using a membrane filter MILLEX-GV (Millipore) having a pore size of 0.22 μm, a soluble form of human IL-3Rα protein was obtained. As a result of Limulus test using Limulus ES-II Kit Wako (Wako Pure Chemical Industries, Ltd.), endotoxin was not detected. Regarding concentration of the soluble form of human IL-3Rα protein, absorbance at 280 nm was measured and 1 mg/ml was calculated as 1.4 OD.

Example 3

Preparation of Anti-Human IL-3Rα Human Antibody Using Human Antibody Producing Mouse (Human Antibody Producing Mouse)

The mouse used in the immunization has a genetic background of homozygote on both of endogenous Ig heavy chain and κ light chain disruptions and also simultaneously keeps the 14$^{th}$ chromosomal fragment containing human Ig heavy chain locus (SC20) and human Ig κ chain transgene (KCo5). This mouse was prepared by the crossing of a line A mouse having the human Ig heavy chain locus onto a line B mouse having the human Ig κ chain transgene. The line A is a homozygote on both of endogenous Ig heavy chain and κ light chain disruptions, is a mouse line which maintain the 14$^{th}$ chromosomal fragment (SC20) which can be transmitted to progeny and is described for example in a report by Tomizuka et al. [Tomizuka et al., *Proc. Natl. Acad. Sci. USA*, 2000, Vol. 97: 722]. Also, the line B is a homozygote on both of endogenous Ig heavy chain and κ light chain disruptions, is a mouse line (transgenic mouse) which maintains a human Ig κ chain transgene (KCo5) and is described in a report by such as Fishwild et al. [*Nat. Biotechnol* (1996), 114: 845].

An individual in which human Ig heavy chain and κ light chain were simultaneously detected in serum, obtained by the crossing of a line A male mouse onto a line B female mouse or the crossing of a line A female mouse onto a line B male mouse, [Ishida & Lonberg, *IBC's* 11$^{th}$ *Antibody Engineering*, Abstract 2000] was used in the following immune test. In this connection, the aforementioned human antibody producing mouse (referred to as KM mouse) can be obtained from Kyowa Hakko Kirin Co., Ltd. by establishing a contract.

(Preparation of Human Monoclonal Antibody to Human IL-3Rα)

Regarding the preparation of monoclonal antibody in this Example, it was prepared in accordance with a general method described in *A Guide to Monoclonal Antibody Experimental Operations* (written in Japanese) (edited by Tamie Ando et al. published by Kodansha, 1991) and the like. For the IL-3Rα as an immunogen, an IL-3Rα expressing L929 cell (CCL-1, ATCC), an IL-3Rα expressing Colon-26 cell (Cell Resource Center for Biomedical Research Institute of Development, Aging and Cancer Tohoku University) or a soluble form of human IL-3Rα Fc fusion protein was used. As an animal to be immunized, the above-mentioned KM mouse was used.

For the purpose of preparing human monoclonal antibody to human IL-3Rα, the KM mouse was immunized with the IL-3Rα expression L929 cell or IL-3Rα expression Colon-26 cell prepared in Example 1, intraperitoneally at a dose of 1×10$^7$ cells/animal every 1 week to 2 weeks in a total of 4 times. Three days before the extraction of spleen which is described below, 20 μg/mouse individual of the soluble form of human IL-3Rα protein was administered through the caudal vein.

After the spleen was surgically obtained from the immunized mouse, the spleen was put into PBS and minced on a mesh (cell strainer, FALCON) using a syringe piston. After the cell suspension was passed through the mesh and was centrifuged, the obtained precipitated cells were re-suspended in Red Blood Cell Lysing Buffer (Sigma). After 5 minutes of incubation at room temperature, serum-free DMEM medium (Invitrogen) containing 350 mg/ml sodium bicarbonate, 50 units/ml penicillin and 50 μg/ml streptomycin (hereinafter referred to as "serum-free DMEM medium") was added thereto to precipitate the cells. By suspending again in the serum-free DMEM medium, the number of cells was measured.

On the other hand, a myeloma cell SP2/0 (ATCC No. CRL-1581) was cultured at 37° C. in the presence of 5% carbon dioxide using DMEM medium (Invitrogen) containing 10% FCS (Invitrogen), 50 units/ml penicillin and 50 μg/ml streptomycin (hereinafter referred to as "serum-containing DMEM medium"). The SP2/0 cells were washed with serum-free DMEM medium. In the same manner, the cells were suspended in serum-free DMEM medium to measure the number of cells. After the suspension of the recovered spleen-derived cells and a suspension of the mouse myeloma were mixed at a cell number ratio of 5:1, the mixed suspension was centrifuged, and then the supernatant was completely removed. As a fusion agent, 50% (w/v) polyethylene glycol 1500 (Boehringer-Mannheim) was slowly added to the obtained pellet while stirring the pellet with the tip of a pipette, and then serum-free DMEM medium heated to 37° C. in advance was slowly added thereto. Furthermore, an appropriate amount of serum-free DMEM medium was slowly added thereto. Thereafter, the obtained solution was allowed to stand still at 37° C. for 5 minutes in the presence of 5% carbon dioxide. After centrifugation, the supernatant was removed and thus obtained fused cells were suspended in DMEM medium (Invitrogen) containing 10% FCS (Invitrogen), penicillin-streptomycin-glutamine (Sigma), IL-6 (5 ng/ml) and 2-mercaptoethanol (Invitrogen) (hereinafter, referred to as "IL-6-containing DMEM medium") and cultured at 37° C. in the presence of 5% carbon dioxide. On the next day, the cells were recovered by pipetting, and precipitated by centrifugation. The obtained cell pellet was re-suspended in the IL-6-containing DMEM medium. The suspended cells were subjected to limiting dilution on a 96-well plate and cultured for about 7 days to 14 days. The culture supernatant was used in the hybridoma screening described in the following example.

(Screening of Hybridoma Producing a Human Monoclonal Antibody which Binds to Human IL-3Rα)

Screening of hybridoma was carried out using the cell supernatant prepared in the above example. The method was, in short, carried out by a flow cytometry in which a human IL-3Rα stable expression cell line was used.

Specifically, a combination of human IL-3Rα expression L929 cell and parent cell line L929 cell or a combination of human IL-3Rα expression Colon-26 cell and parent cell line Colon-26 cell, was mixed with the supernatant of hybridoma and allowed to stand still at 4° C. for 30 minutes. After washing the obtained cells twice with a staining medium (Dulbecco's PBS containing 2% fetal calf serum, 2 mM EDTA, 0.05% NaN$_3$), Goat F(ab')$_2$ Anti-Human IgG-PE (Southern Biotech) as a secondary antibody was added thereto and allowed to stand still at 4° C. for 30 minutes. After washing twice with the staining medium, the obtained cells were analyzed by FACSCalibur (BD Biosciences). A hybridoma which reacted with only human IL-3Rα expression L929 cell was collected.

The selected hybridoma was subjected to limiting dilution, and screening was carried out using its culture supernatant. Specifically, each of human IL-3Rα expression L929 cell and parent cell line L929 cell was mixed with the supernatant of hybridoma and allowed to stand still at 4° C. for 30 minutes. After washing twice with the staining medium, Goat F(ab')$_2$ Anti-Human kappa-PE (Dako) as a secondary antibody was added thereto and allowed to stand still at 4° C. for 30 minutes. After washing twice with the staining medium, the cells were analyzed by FACSCalibur (BD Biosciences). A hybridoma which reacted with only human IL-3Rα expression L929 cell was collected.

Example 4

Preparation of Recombinant Anti-Human IL-3Rα Human Antibody (Obtaining of Anti-Human IL-3Rα Human Antibody Gene from Hybridoma and Preparation of Expression Vector)

From the hybridoma obtained in Example 3, clone names Old 4, Old5, Old17, Old19, New102 and Old6 were cultured using eRDF medium (Kyokuto Pharmaceutical Industrial Co., Ltd.) containing 10 ng/ml IL-6 (R & D Systems) and 10% Fetal Bovine Serum (SIGMA) and then cells were collected by centrifugation. To the obtained cells, and then TRIZOL (GIBCO) was added and total RNA was extracted in accordance with the instructions. Cloning of variable region of the antibody cDNA was carried out using SMART RACE cDNA Amplification Kit (Clontech) in accordance with the instructions attached thereto.

In addition, variable region was cloned from a hybridoma ATCC, HB12009, which produces an anti-human IL-3Rα mouse antibody 7G3 and was used as a control. By connecting the thus obtained cDNA with a DNA encoding human IgG1 constant region, a chimeric antibody expression vector was prepared. Specifically, the cells were collected by centrifugation from the cryopreserved hybridoma, and then TRIZOL (GIBCO) was added thereto to extract total RNA in accordance with the instructions. Cloning of variable region of the antibody cDNA was carried out using mouse IgG antibody-specific primes in addition to the SMART RACE cDNA Amplification Kit (Clontech), in accordance with the instructions attached thereto.

Using 5 μg of the total RNA as a template, the 1st strand cDNA was prepared.
1) Synthesis of the 1st strand cDNA
  Total RNA 5 μgm/34
  5'CDS 1 μL
  SMART oligo 1 μL
After the reaction mixture comprising the above compositions was incubated at 72° C. for 2 minutes,
  5× Buffer 2 μL
  DTT 1 μL
  DNTP mix 14, and
  SuperscriptII 1 μL
were added to the reaction mixture and incubated at 42° C. for 1.5 hours.

To the obtained mixture, 100 μl of Tricine Buffer was further added and incubated at 72° C. for 7 minutes.
2) Amplification of heavy chain gene and light chain gene by PCR and construction of expression vector of recombinant antibody
For amplification of cDNA, Z-Taq manufactured by Takara was used.
  cDNA 2 μL
  10×Z-Taq Buffer 5 μL
  dNTPmix 44
  Z-Taq1 μL
  Primer 1
  Primer 2
A reaction solution comprising the above-mentioned composition was adjusted to a final volume of 50 μl with re-distilled water to be subjected to PCR.

For amplification of the heavy chain, UPM (SMART RACE cDNA Amplification Kit; manufactured by Clontech) and hh-6 primer (5'-GGTCCGGGAGATCATGAGGGTGTCCTT-3') (SEQ ID NO:15) were used and a cycle of reactions at 98° C. 1 second and 68° C. 30 seconds was repeated 30 times. Further, using 1 μl of the obtained reaction solution as a template and using NUP (SMART RACE cDNA Amplification Kit; manufactured by Clontech) and hh-3 primer (5'-GTGCACGCCGCT GGT CAGGGCGCCTG-3') (SEQ ID NO:16) as primers, a cycle of reactions at 98° C. 1 second and 68° C. 30 seconds was repeated 20 times. Thereafter, the amplified PCR products were purified using PCR purification kit (QIAGEN), and nucleotide sequences was determined using hh-4 (5'-GGT GCC AGG GGG AAG ACC GAT GG-3') (SEQ ID NO:17) as a primer. The following specific primers were synthesized based on sequence information, and the sequences were also determined from the opposite direction using the following primers.

```
Old4 heavy chain specific primer Fw
                                       (SEQ ID NO: 18)
(5'-AGAGAGAGAGGTCGACCACCATGGACTGGACCTGGAGGTTCCTCT

TTG T-3')

Old4 heavy chain specific primer Rv
                                       (SEQ ID NO: 19)
(5'-AGAGAGAGAGGCTAGCTGAAGAGACGGTGACCATTGTCCC-3')

Old5 heavy chain specific primer Fw
                                       (SEQ ID NO: 20)
(5'-AGAGAGAGAGGTCGACCACCATGGACTGGACCTGGAGGTTCCTCT

TTG T-3')

Old5 heavy chain specific primer Rv
                                       (SEQ ID NO: 21)
(5'-AGAGAGAGAGGCTAGCTGAAGAGACGGTGACCATTGTCCC-3')

Old17 heavy chain specific primer Fw
                                       (SEQ ID NO: 22)
(5'-AGAGAGAGAGGTCGACCACCATGGACTGGACCTGGAGGTTCCTCT

TTG T-3')

Old17 heavy chain specific primer Rv
                                       (SEQ ID NO: 23)
(5'-AGAGAGAGAGGCTAGCTGAGGAGACGGTGACAAGGGTTCCC-3')

Old19 heavy chain specific primer Fw
                                       (SEQ ID NO: 24)
(5'-AGAGAGAGAGGTCGACCACCATGGACTGGACCTGGAGGTTCCTCT

TTG T-3')

Old19 heavy chain specific primer Rv
                                       (SEQ ID NO: 25)
(5'-AGAGAGAGAGGCTAGCTGAGGAGACGGTGACCAGGGTTC-3')

New102 heavy chain specific primer Fw
                                       (SEQ ID NO: 26)
(5'-AGAGAGAGAGGTCGACCACCATGGACTGGACCTGGAGGTTCCTC

TTTG T-3')

New102 heavy chain specific primer Rv
                                       (SEQ ID NO: 27)
(5'-AGAGAGAGAGGCTAGCTGAGGAGACGGTGACCAGGGTT-3')

Old6 heavy chain specific primer Fw
                                       (SEQ ID NO: 28)
(5'-AGAGAGAGAGGTCGACCCACCATGGAACTGGGGCTCCGCTG-3')

Old6 heavy chain specific primer Rv
                                       (SEQ ID NO: 29)
(5'-AGAGAGAGAGGCTAGCTGAGGAGACGGTGACCAGGGTTC-3')
```

For the amplification of the heavy chain of mouse antibody 7G3, UPM (SMART RACE cDNA amplification Kit; manufactured by Clontech) and mH-Rv1 primer (5'-ATTTTG TCG ACC KYG GTS YTG CTG GCY GGGTG-3') (SEQ ID NO:30) were used and a cycle of reactions at 98° C. 1 second and 68° C. 30 seconds was repeated 30 times. Further, using 1 µl of this reaction solution as a template and using NUP (SMART RACE cDNA Amplification Kit; manufactured by Clontech) and mH-Rv2 primer (5'-GCACACYRCTGGA-CAGGGATCCAGAGTTCC-3') (SEQ ID NO:31), a cycle of reactions at 98° C. 1 second and 68° C. 30 seconds was repeated 20 times. Thereafter, the amplified PCR products were purified using PCR purification kit (QIAGEN), and the nucleotide sequence of heavy chain variable region was determined by using mH-Rv2 primer (SEQ ID NO:31) as a primer. The following specific primers were synthesized based on sequence information, and the sequences were also determined from the opposite direction using the following primers.

```
7G3 heavy chain specific primer Fw
                                  (SEQ ID NO: 32)
(5'-AGAGAGAGAGGTCGACCACCATGGGATGGAGCTGGATCTTTCT

C-3')

7G3 heavy chain specific primer Rv
                                  (SEQ ID NO: 33)
(5'-AGAGAGAGAGGCTAGCTGCAGAGACAGTGACCAGAGTCCC-3')
```

PCR was carried out using the above-mentioned specific primers (98° C. 1 second, 60° C. 30 seconds, 72° C. 30 seconds), and heavy chain amplification cDNA fragment was digested with SalI and NheI and inserted into a N5KG1-Val Lark vector [a modified vector of N5KG1 (U.S. Pat. No. 6,001,358, Idec Pharmaceuticals)] which had been cleaved with the same enzymes. By determining the sequence using the vector as a template, it was found that the inserted sequence is identical to the one determined by direct sequence.

The light chain was amplified using UPM (SMART RACE cDNA Amplification Kit; manufactured by Clontech) and hk-2 primer (5'-GTT GAAGCT CTT TGT GAC GGG CGA GC-3') (SEQ ID NO:34) and repeating a cycle of reactions at 98° C. 1 second and 68° C. 30 seconds 30 times. Further, using 1 µl of this reaction solution as a template and using NUP (SMART RACE cDNA Amplification Kit; manufactured by Clontech) and hk-6 (5'-TGGCGGGAAGATG AAG ACA GAT GGT G-3') (SEQ ID NO:35), a cycle of reactions at 98° C. 1 second and 68° C. 30 seconds was repeated 20 times. Thereafter, the amplified PCR products were purified using PCR purification kit (QIAGEN), and the nucleotide sequence was determined using hk-6 primer. The following specific primers were synthesized based on sequence information, and the sequences were determined also from the opposite direction.

```
Old4 light chain specific primer Fw
                                  (SEQ ID NO: 36)
(5'-AGAGAGAGAGATCTCTCACCATGGACATGAGGGTCC CCG CTC

AGC-3')

Old4 light chain specific primer Rv
                                  (SEQ ID NO: 37)
(5'-AGAGAGAGAGCGTACGTTTGATCTCCAGCTTGGTCC CCT

G-3')

Old5 light chain specific primer Fw
                                  (SEQ ID NO: 38)
(5'-AGA GAGAGAGATCTCTCACCATGGACATGAGGGTCCCCG CTC

AGC-3')

Old5 light chain specific primer Rv
                                  (SEQ ID NO: 39)
(5'-AGAGAGAGAGCGTACGTTTGATCTCCAGCTTGGTCC CCT

G-3')

Old17 light chain specific primer Fw
                                  (SEQ ID NO: 40)
(5'-AGAGAGAGAGATCTCTCACCATGGACATGAGGGTCC TCG CTC

AG-3')

Old17 light chain specific primer Rv
                                  (SEQ ID NO: 41)
(5'-AGAGAGAGAGCGTACGTTTGATCTCCAGCTTGGTCC CCT

G-3')

Old19 light chain specific primer Fw
                                  (SEQ ID NO: 42)
(5'-AGAGAGAGAGATCTCTCACCATGGACATGAGGGTCC TCG CTC

AG-3')

Old19 light chain specific primer Rv
                                  (SEQ ID NO: 43)
(5'-AGAGAGAGAGCGTACGTTTGATTTCCACCTTGGTCC CTT

GGC-3')

New102 light chain specific primer Fw
                                  (SEQ ID NO: 44)
(5'-AGAGAGAGAGATCTCTCACCATGGACATGAGGGTCC TCG CTC

AG-3')

New102 light chain specific primer Rv
                                  (SEQ ID NO: 45)
(5'-AGAGAGAGAGCGTACGTTTGATCTCCAGCTTGG TCC CCT

G-3')

Old6 light chain specific primer Fw
                                  (SEQ ID NO: 46)
(5'-AGAGAGAGAGATCTCTCACCATGGACATGAGGGTCCCC

GCTCAGC-3')

Old6 light chain specific primer Rv
                                  (SEQ ID NO: 47)
(5'-AGAGAGAGAGCGTACGTTTGATATCCACTTTGGTCCCAGGGC-3')
```

Light chain of the mouse antibody 7G3 was amplified using UPM (SMART RACE cDNA amplification Kit; manufactured by Clontech) and mK-Rv1 primer mK_Rv1 (5'-TT GAA GCT CTT GAC AAT GGG TGA AGT TGAT-3') (SEQ ID NO:48) and repeating a cycle of reactions at 98° C. 1 second and 68° C. 30 seconds 30 times. Further, using 1 µl of this reaction solution as a template and using NUP (SMART RACE cDNA Amplification Kit; manufactured by Clontech) and mK-Rv2 (5'-GTAGGTGCTGTCTTTGCTGTCCTGAT-CAGT-3') (SEQ ID NO:49), a cycle of reactions at 98° C. 1 second and 68° C. 30 seconds was repeated 20 times. Thereafter, the amplified PCR products were purified using PCR purification kit (QIAGEN), and the nucleotide sequence was determined using mK-Rv2 primer. The following specific primers were synthesized based on sequence information, and the sequences were also determined from the opposite direction.

7G3 light chain specific primer Fw
(SEQ ID NO: 50)
(5'-AGAGAGAGAGAGATCTCACCATGGAATCACAGACTCAGGTCCT
C-3')

7G3 light chain specific primer Rv
(SEQ ID NO: 51)
(5'-AGAGAGAGAGCGTACGTTTTATTTCCAGCTTGGTCCCCC-3')

PCR was carried out using the above-mentioned specific primers (98° C. 1 second, 60° C. 30 seconds, 72° C. 30 seconds), and s light chain amplification cDNA fragment was digested with BglII and BsiWI and inserted into a N5KG1-Val Lark vector which had been cleaved with the same enzymes. By determining the sequence using the vector as a template, it was found that the inserted sequence is identical to the one determined by direct sequence.

Each of DNA molecules encoding the heavy chain variable region and light chain variable region of Old4 and amino acid sequences of the heavy chain variable region and light chain variable region are shown in the following.

<Old4 heavy chain variable region>
(SEQ ID NO: 52)
GACCCGTCGACCACC<u>ATG</u>GACTGGACCTGGAGGTTCCTCTTTGTGGTGGC

AGCAGCTACAGGTGTCCAGTCCCAGGTCCAGCTGCTACAGTCTGGGGCTG

AGGTGAAGAAGCCTGGGTCCTCGGTGAAGGTCTCATGCAAGGCTTCTGGA

GGCACCTTCAGCACCTATGCTATCAGCTGGGTGCGACAGGCCCCTGGACA

AGGGCTTGAGTGGATGGGAGGGATCATCCCTATCTTTGGTATAGTAAACT

ACGCACAGAAGTTCCAGGGCAGAGTCACGATTACCGCGGACGAATCCACG

AGTACAGCCTACATGGAACTGAGCAGCCTGAGATCTGAGGACACGGCCGT

GTATTATTGTGCGAGAGGGGGGGGCTCGGGCCCAGATGTTCTTGATATCT

GGGGCCAAGGGACAATGGTCACCGTCTCTTC<u>A</u>GCTAGCACCAA

<Old4 heavy chain variable region>
(SEQ ID NO: 53)
MDWTWRFLFVVAAATGVQSQVQLLQSGAEVKKPGSSVKVSCKASGGTFST

YAISWVRQAPGQGLEWMGGIIPIFGIVNYAQKFQGRVTITADESTSTAYM

ELSSLRSEDTAVYYCARGGGSGPDVLDIWGQGTMVTVSSASTX

The translation initiation site of the heavy chain DNA is an ATG codon which starts from adenine (A) at position 16 from the 5'-terminal of SEQ ID NO:52, and a boundary between the antibody variable region and the constant region is located between adenine (A) at position 432 and guanine (G) at position 433 from the 5'-terminal. In the heavy chain amino acid sequence, the heavy chain variable region is up to serine (S) residue at position 139 from the N-terminal of SEQ ID NO:53, and the constant region is on and after alanine (A) at position 140. By a gene sequence estimation software (Signal P ver. 2), the signal sequence of heavy chain was estimated to be up to serine (S) at position 19 from the N-terminal of SEQ ID NO:53. The N-terminal of the mature form was considered to be glutamine (Q) at position 20 of SEQ ID NO:53.

<Old4 light chain variable region>
(SEQ ID NO: 54)
CACAGATCTCTCACC<u>ATG</u>GACATGAGGGTCCCCGCTCAGCTCCTGGGGCT

CCTGCTGCTCTGGCTCCCAGGTGCCAGATGTGTCATCTGGATGACCCAGT

CTCCATCCTTACTCTCTGCATCTACAGGAGACAGAGTCACCATCAGTTGT

CGGATGAGTCAGGGCATTAGGAGTTATTTAGCCTGGTATCAGCAAAAACC

AGGGAAAGCCCCTGAGCTCCTGATCTATGCTGCATCCACTTTGCAAAGTG

GGGTCCCATCAAGGTTCAGTGGCAGTGGATCTGGGACAGATTTCACTCTC

ACCATCAGCAGCCTGCAGTCTGAAGATTTTGCAACTTATTACTGTCAACA

GTATTATAGTTTCCCGTACACTTTTGGCCAGGGGACCAAGCTGGAGATCA

A<u>A</u>CGTACGGTGG

<Old4 light chain variable region>
(SEQ ID NO: 55)
MDMRVPAQLLGLLLLWLPGARCVIWMTQSPSLLSASTGDRVTISCRMSQG

IRSYLAWYQQKPGKAPELLIYAASTLQSGVPSRFSGSGSGTDFTLTISSL

QSEDFATYYCQQYYSFPYTFGQGTKLEIKRTVX

The translation initiation site of the light chain DNA is an ATG codon which starts from adenine (A) at position 16 from the 5'-terminal of SEQ ID NO:54, and a boundary between the variable region and the constant region of the antibody is located between adenine (A) at position 402 and cytosine (C) at position 403 from the 5'-terminal. In the light chain amino acid sequence, the light chain variable region is up to lysine (K) residue at position 129 from the N-terminal of SEQ ID NO:55, and the constant region is on and after arginine (R) at position 130. By a gene sequence estimation software (Signal P ver. 2), the signal sequence of light chain was estimated to be up to cysteine (C) at position 22 from the N-terminal of SEQ ID NO:55. The N-terminal of the mature form was considered to be valine (V) at position 23 of SEQ ID NO:55.

Each of DNA molecules encoding the heavy chain variable region and the light chain variable region of Old5 and amino acid sequences of the heavy chain variable region and light chain variable region was shown in the following.

<Old5 heavy chain variable region>
(SEQ ID NO: 56)
GTCGACCACC<u>ATG</u>GACTGGACCTGGAGGTTCCTCTTTGTGGTGGCAGCAG

CTACAGGTGTCCAGTCCCAGGTCCAGCTGGTGCAGTCTGGGGCTGAGGTG

AAGAAGCCTGGGTCCTCGGTGAAGGTCTCATGCAAGGCTTCTGGAGGCAC

CTTCAGCACCTATGCTATCAGCTGGGTGCGACAGGCCCCTGGACAAGGGC

TTGAGTGGATGGGAGGGCTCATCCCTATCTTTGATATAGAAAACTACGCA

CAGAAGTTCCAGGGCAGAGTCACGATTACCGCGGACGAATCCACGAGCAC

AGTCTATATGGAACTGAGCAGCTGAGATCTGAGGACACGGCCATGTATCT

ACTGTGCGAGAGGGGGGGGTTCGGGCCCTGATGTTCTTGATATCTGGGGC

CAAGGGACAATGGTCACCGTCTCTTC<u>A</u>GCTAGC

<Old5 heavy chain variable region>
(SEQ ID NO: 57)
MDWTWRFLFVVAAATGVQSQVQLVQSGAEVKKPGSSVKVSCKASGGTFST

YAISWVRQAPGQGLEWMGGLIPIFDIENYAQKFQGRVTITADESTSTVYM

ELSSLRSEDTAMYYCARGGGSGPDVLDIWGQGTMVTVSSAS

The translation initiation site of the heavy chain DNA is an ATG codon which starts from adenine (A) at position 16 from the 5'-terminal of SEQ ID NO:56, and a boundary between the variable region and the constant region of the antibody is located between adenine (A) at position 427 and guanine (G) at position 428 from the 5'-terminal. In the heavy chain amino acid sequence, the heavy chain variable region is up to serine (S) residue at position 139 from the N-terminal of SEQ ID NO:57, and the constant region is on and after alanine (A) at position 140. By a gene sequence estimation software (Signal P ver. 2), the signal sequence of heavy chain was estimated to be up to serine (S) at position 19 from the N-terminal of SEQ ID NO:57. The N-terminal of the mature form was considered to be glutamine (Q) at position 20 of SEQ ID NO:57.

<Old5 light chain variable region>
(SEQ ID NO: 58)
CACAGATCTCTCACC<u>ATG</u>GACATGAGGGTCCCCGCTCAGCTCCTGGGGCT

CCTGCTGCTCTGGCTCCCAGGTGCCAGATGTGTCATCTGGATGACCCAGT

CTCCATCCTTACTCTCTGCATCTACAGGAGACAGAGTCACCATCAGTTGT

CGGATGAGTCAGGGCATTAGGAGTTATTTAGCCTGGTATCAGCAAAAACC

AGGGAAAGCCCCTGAGCTCCTGATCTATGCTGCATCCACTTTGCAAAGTG

GGGTCCCATCAAGGTTCAGTGGCAGTGGATCTGGGACAGATTTCACTCTC

ACCATCAGCAGCCTGCAGTCTGAAGATTTTGCAACTTATTACTGTCAACA

GTATTATAGTTTCCCGTACACTTTTGGCCAGGGGACCAAGCTGGAGATCA

A<u>A</u>CGTACGGTGG

<Old5 light chain variable region>
(SEQ ID NO: 59)
MDMRVPAQLLGLLLLWLPGARCVIWMTQSPSLLSASTGDRVTISCRMSQG

IRSYLAWYQQKPGKAPELLIYAASTLQSGVPSRFSGSGSGTDFTLTISSL

QSEDFATYYCQQYYSFPYTFGQGTKLEIKRTVX

The translation initiation site of the light chain DNA is an ATG codon which starts from adenine (A) at position 16 from the 5'-terminal of SEQ ID NO:58, and a boundary between the variable region and the constant region of the antibody is located between adenine (A) at position 402 and cytosine (C) at position 403 from the 5'-terminal. In the light chain amino acid sequence, the light chain variable region is up to lysine (K) residue at position 129 from the N-terminal of SEQ ID NO:59, and the constant region is on and after arginine (R) at position 130. By a gene sequence estimation software (Signal P ver. 2), the signal sequence of light chain was estimated to be up to cysteine (C) at position 22 from the N-terminal of SEQ ID NO:59. The N-terminal of the mature form was considered to be valine (V) at position 23 of SEQ ID NO:59.

Each of DNA molecules encoding the heavy chain variable region and the light chain variable region of Old17 and the amino acid sequences of the heavy chain variable region and the light chain variable region are shown in the following.

<Old17 heavy chain variable region>
(SEQ ID NO: 60)
GACCCGTCGACCACC<u>ATG</u>GACTGGACCTGGAGGTTCCTCTTTGTGGTGGC

AGCAGCTACAGGTGTCCAGTCCCAGGTCCAGCTGGTGCAGTCTGGGGCTG

AGGTGAAGAAGCCTGGGTCCTCGGTGAAGGTCTCCTGCAAGACTTCTGGA

GGCACCTTCAGCAACTTTGCTATCAGCTGGGTGCGACAGGCCCCTGGACA

AGGGCTTGAGTGGATGGGAGGGATCATCCCTATCTTTGGTTCAACAAACT

ACGCACAGAAGTTCCAGGGCAGAGTCACGATTAACGCGGACGAATCCACG

AGCACAGCCTACATGGAGCTGAGCAGTCTGAGATCTGAGGACACGGCCGT

GTATTACTGTGCGGGTGGAGACAAATATGGTCCTTACTACTTTCACTACT

GGGGCCAGGGAACCCTTGTCACCGTCTCCTC<u>A</u>GCTAGC

<Old17 heavy chain variable region>
(SEQ ID NO: 61)
MDWTWRFLFVVAAATGVQSQVQLVQSGAEVKKPGSSVKVSCKTSGGTFSN

FAISWVRQAPGQGLEWMGGIIPIFGSTNYAQKFQGRVTINADESTSTAYM

ELSSLRSEDTAVYYCAGGDKYGPYYFHYWGQGTLVTVSSAS

The translation initiation site of the heavy chain DNA is an ATG codon which starts from adenine (A) at position 16 from the 5'-terminal of SEQ ID NO:60, and a boundary between the variable region and the constant region of the antibody is located between adenine (A) at position 432 and guanine (G) at position 433 from the 5'-terminal. In the heavy chain amino acid sequence, the heavy chain variable region is up to serine (S) residue at position 139 from the N-terminal of SEQ ID NO:61, and the constant region is on and after alanine (A) at position 140. By a gene sequence estimation software (Signal P ver. 2), the signal sequence of heavy chain was estimated to be up to serine (S) at position 19 from the N-terminal of SEQ ID NO:61. The N-terminal of the mature form was considered to be glutamine (Q) at position 20 of SEQ ID NO:61.

<Old17 light chain variable region>
(SEQ ID NO: 62)
AGATCTCTCACCATGGAC<u>ATG</u>AGGGTCCTCGCTCAGCTCCTGGGGCTCCT

GCTGCTCTGTTTCCCAGGTGCCAGATGTGACATCCAGATGACCCAGTCTC

CATCCTCACTGTCTGCATCTGTAGGAGACAGAGTCACCATCACTTGTCGG

GCGAGTCAGGGTATTAGCAGCTGGTTAGCCTGGTATCAGCAGAAACCAGA

GAAAGCCCCTAAGTCCCTGATCTATGCTGCATCCAGTTTGCAAAGTGGGG

TCCCATCAAGGTTCAGCGGCAGTGGATCTGGGACAGATTTCACTCTCACC

ATCAGCAGCCTGCAGCCTGAAGATTTTGCAACTTATTACTGCCAACAGTA

TAATAGTTACCCGTACACTTTTGGCCAGGGGACCAAGCTGGAGATCAA<u>A</u>C

GTACGGT

<Old17 light chain variable region>
(SEQ ID NO: 63)
MDMRVLAQLLGLLLLCFPGARCDIQMTQSPSSLSASVGDRVTITCRASQG

ISSWLAWYQQKPEKAPKSLIYAASSLQSGVPSRFSGSGSGTDFTLTISSL

QPEDFATYYCQQYNSYPYTFGQGTKLEIKRTX

The translation initiation site of the light chain DNA is an ATG codon which starts from adenine (A) at position 19 from the 5'-terminal of SEQ ID NO:62, and a boundary between the variable region and the constant region of the antibody is located between adenine (A) at position 399 and cytosine (C) at position 400 from the 5'-terminal. In the light chain amino acid sequence, the light chain variable region is up to lysine (K) residue at position 129 from the N-terminal of SEQ ID NO:63, and the constant region is on and after arginine (R) at position 130. By a gene sequence estimation software (Signal P ver. 2), it was estimated that the signal sequence of light chain is up to cysteine (C) at position 22 from the N-terminal of SEQ ID NO:63. It is considered that the N-terminal of the mature form is aspartic acid (D) at position 23 of SEQ ID NO:63.

Each of DNA molecules encoding the heavy chain variable region and the light chain variable region of Old19 and the amino acid sequences of the heavy chain variable region and light chain variable region was shown in the following.

<Old19 heavy chain variable region>
(SEQ ID NO: 64)
TCGACCCC<u>ATG</u>GACTGGACCTGGAGGTTCCTCTTTGTGGTGGCAGCAGCT

ACAGGTGTCCAGTCCCAGGTCCAGCTGGTGCAGTCTGGGGCTGAGGTGAA

GAAGCCTGGGTCCTCGGTGAAGGTCTCCTGCAAGGCTTCTGGAGGCACCT

TCAGCAGCTATGCTATCAGCTGGGTGCGACAGGCCCCTGGACAAGGGCTT

GAGTGGGTGGGAGGGATCATCCCTATCTTTGGTACAGCAAACTACGCACA

GAAGTTCCAGGGCAGAGTCACGATTACCGCGGACGAATCCACGAGCACAG

CCTACATGGAGCTGAGCAGCCTGAGATCTGAGGACACGGCCGTGTATTAC

TGTGCGAGAGGACACAAATATGGCCCCTACTACTTTGACTACTGGGGCCA

GGGAACCCTGGTCACCGTCTCCTC<u>A</u>GCTAGCACCAAG

<Old19 heavy chain variable region>
(SEQ ID NO: 65)
MDWTWRFLFVVAAATGVQSQVQLVQSGAEVKKPGSSVKVSCKASGGTFSS

YAISWVRQAPGQGLEWVGGIIPIFGTANYAQKFQGRVTITADESTSTAYM

ELSSLRSEDTAVYYCARGHKYGPYYFDYWGQGTLVTVSSASTK

The translation initiation site of the heavy chain DNA is an ATG codon which starts from adenine (A) at position 9 from the 5'-terminal of SEQ ID NO:64, and a boundary between the variable region and the constant region of the antibody is located between adenine (A) at position 425 and guanine (G) at position 426 from the 5'-terminal. In the heavy chain amino acid sequence, the heavy chain variable region is up to serine (S) residue at position 139 from the N-terminal of SEQ ID NO:65, and the constant region is on and after alanine (A) at position 140. By a gene sequence estimation software (Signal P ver. 2), it was estimated that the signal sequence of heavy chain is up to serine (S) at position 19 from the N-terminal of SEQ ID NO:65. It is considered that the N-terminal of the mature form is the glutamine (Q) at position 20 of SEQ ID NO:65.

<Old19 light chain variable region>
(SEQ ID NO: 66)
AGATCTCTCACC<u>ATG</u>GACATGAGGGTCCTCGCTCAGCTCCTGGGGCTCCT

GCTGCTCTGTTTCCCAGGTGCCAGATGTGACATCCAGATGACCCAGTCTC

CATCCTCACTGTCTGCATCTGTAGGAGACAGAGTCACCATCACTTGTCGG

GCGAGTCAGGGTATTAGCAGCTGGTTAGCCTGGTATCAGCAGAAACCAGA

GAAAGCCCCTAAGTCCCTGATCTATGCTGCATCCAGTTTGCAAAGTGGGG

TCCCATCAAGGTTCAGCGGCAGTGGATCTGGGACAGATTTCACTCTCACC

ATCAGCAGCCTGCAGCCTGAAGATTTTGCAACTTATTACTGCCAACAGTA

TAATAGTTACCCTCGGACGTTCGGCCAAGGGACCAAGGTGGAAATCAAA<u>C</u>

GTACGGTGGCT

<Old19 light chain variable region>
(SEQ ID NO: 67)
MDMRVLAQLLGLLLLCFPGARCDIQMTQSPSSLSASVGDRVTITCRASQG

ISSWLAWYQQKPEKAPKSLIYAASSLQSGVPSRFSGSGSGTDFTLTISSL

QPEDFATYYCQQYNSYPRTFGQGTKVEIKRTVA

The translation initiation site of the light chain DNA is an ATG codon which starts from adenine (A) at position 13 from the 5'-terminal of SEQ ID NO:66, and a boundary between the variable region and the constant region of the antibody is located between adenine (A) at position 399 and cytosine (C) at position 400 from the 5'-terminal. In the light chain amino acid sequence, the light chain variable region is up to lysine (K) residue at position 129 from the N-terminal of SEQ ID NO:67, and the constant region is on and after arginine (R) at position 130. By a gene sequence estimation software (Signal P ver. 2), it was estimated that the signal sequence of light chain is up to cysteine (C) at position 22 from the N-terminal of SEQ ID NO:67. It is considered that the N-terminal of the mature form is aspartic acid (D) at position 23 of SEQ ID NO:67.

Each of DNA molecules encoding the heavy chain variable region and the light chain variable region of New102 and the amino acid sequences of the heavy chain variable region and light chain variable region was shown in the following.

<New102 heavy chain variable region>
(SEQ ID NO: 68)
TCGACCACC<u>ATG</u>GACTGGACCTGGAGGTTCCTCTTTGTGGTGGCAGCAGC

TACAGGTGTCCAGTCCCAGGTCCAGCTGGTGCAGTCTGGGGCTGAGGTGA

AGAAGCCTGGATCCTCGGTGAAGGTCTCCTGCATGGCTTCAGGAGGCACC

GTCAGCAGCTACGCTATCAGCTGGGTGCGACAGGCCCCTGGACAAGGGCT

TGAGTGGATGGGAGAGATCATCCCTATCTTTGGTATAGTAAACTACGCAC

AGAAGTTCCAGGGCAGAGTCACGATTACCGCGGACGAATCCACGAACACA

GCCTACATGGAGCTGAGCAGCCTGAGATCTGAGGACACGGCCATATATTA

CTGTGCGAGAGAGACAGCAGTGGCTGGTATTCTTGGTTACTGGGGCCAGG

GAACCCTGGTCACCGTCTCCTC<u>A</u>GCTAGCACCAAG

<New102 heavy chain variable region>
(SEQ ID NO: 69)
MDWTWRFLFVVAAATGVQSQVQLVQSGAEVKKPGSSVKVSCMASGGTVSS

YAISWVRQAPGQGLEWMGEIIPIFGIVNYAQKFQGRVTITADESINTAYM

ELSSLRSEDTAIYYCARETAVAGILGYWGQGTLVTVSSASTK

The translation initiation site of the heavy chain DNA is an ATG codon which starts from adenine (A) at position 9 from the 5'-terminal of SEQ ID NO:68, and a boundary between the variable region and the constant region of the antibody is located between adenine (A) at position 423 and guanine (G) at position 424 from the 5'-terminal. In the heavy chain amino acid sequence, the heavy chain variable region is up to serine (S) residue at position 138 from the N-terminal of SEQ ID NO:69, and the constant region is on and after alanine (A) at position 139. By a gene sequence estimation software (Signal P ver. 2), it was estimated that the signal sequence of heavy chain is up to serine (S) at position 19 from the N-terminal of SEQ ID NO:69. It is considered that the N-terminal of the mature form is glutamine (Q) at position 20 of SEQ ID NO:69.

<New102 light chain variable region>
(SEQ ID NO: 70)
AGATCTCTCACC<u>ATG</u>GACATGAGGGTCCTCGCTCAGCTCCTGGGGCTCCT

GCTGCTCTGTTTCCCAGGTGCCAGATGTGACATCCAGATGACCCAGTCTC

CATCCTCACTGTCTGCATCTGTAGGAGACAGAGTCACCATCACTTGTCGG

GCGAGTCAGGGTATTAGCAGCTGGTTAGCCTGGTATCAGCAGAAACCAGA

GAAAGCCCCTAAGTCCCTGATCTATGCTGCATCCAGTTTGCAAAGTGGGG

-continued
TCCCATCAAGGTTCAGCGGCAGTGGATCTGGGACAGATTTCACTCTCACC

ATCAGCAGCCTGCAGCCTGAAGATTTTGCAACTTATTACTGCCAACAGTA

TAATAGTTACCCGTACACTTTTGGCCAGGGGACCAAGCTGGAGATCAAAC

GTACGGTGGCTGCA

<New102 light chain variable region>
(SEQ ID NO: 71)
MDMRVLAQLLGLLLLCFPGARCDIQMTQSPSSLSASVGDRVTITCRASQG

ISSWLAWYQQKPEKAPKSLIYAASSLQSGVPSRFSGSGSGTDFTLTISSL

QPEDFATYYCQQYNSYPYTFGQGTKLEIKRTVAA

The translation initiation site of the light chain DNA is an ATG codon which starts from adenine (A) at position 13 from the 5'-terminal of SEQ ID NO:70, and a boundary between the variable region and the constant region of the antibody is located between adenine (A) at position 399 and cytosine (C) at position 400 from the 5'-terminal. In the light chain amino acid sequence, the light chain variable region is up to lysine (K) residue at position 129 from the N-terminal of SEQ ID NO:71, and the constant region is on and after arginine (R) at position 130. By a gene sequence estimation software (Signal P ver. 2), the signal sequence of light chain was estimated to be up to cysteine (C) at position 22 from the N-terminal of SEQ ID NO:71. The N-terminal of the mature form was considered to be aspartic acid (D) at position 23 of SEQ ID NO:71.

Each of DNA molecules encoding the heavy chain variable region and the light chain variable region of Old6 and amino acid sequences of the heavy chain variable region and the light chain variable region was shown in the following.

<Old6 heavy chain variable region>
(SEQ ID NO: 72)
CGACCCACCATGGAACTGGGGCTCCGCTGGGTTTTCCTTGTTGCTATTTT

AGAAGGTGTCCAGTGTGAGGTGCAGTTGGTGGAGTCTGGGGGAGGCCTGG

TCAAGCCTGGGGGGTCCCTGAGACTCTCCTGTGCAGCCTCTGGATTCACC

TTCAGTAGCCATAACATGAACTGGGTCCGCCAGGCTCCAGGGAAGGGGCT

GGAGTGGGTCTCATCCATTAGTAGTAGTAGTAGTTACATATATTATGCAG

ACTCAGTGAAGGGCCGATTCACCATCTCCAGAGACAACGCCAAGAACTCA

CTGTATCTGCAAATGAACAGCCTGAGAGCCGAGGACACGGCTGTGTATTA

CTGTGCGAGAGAGGACTGGGGCTACTTTGACTACTGGGGCCAGGGAACCC

TGGTCACCGTCTCCTCAGCTAGC

<Old6 heavy chain variable region>
(SEQ ID NO: 73)
MELGLRWVFLVAILEGVQCEVQLVESGGGLVKPGGSLRLSCAASGFTFSS

HNMNWVRQAPGKGLEWVSSISSSSSYIYYADSVKGRFTISRDNAKNSLYL

QMNSLRAEDTAVYYCAREDWGYFDYWGQGTLVTVSSASTK

The translation initiation site of the heavy chain DNA is an ATG codon which starts from adenine (A) at position 10 from the 5'-terminal of SEQ ID NO:72, and a boundary between the variable region and the constant region of the antibody is located between adenine (A) at position 417 and guanine (G) at position 418 from the 5'-terminal. In the heavy chain amino acid sequence, the heavy chain variable region is up to serine (S) residue at position 136 from the N-terminal of SEQ ID NO:73, and the constant region is on and after alanine (A) at position 137. By a gene sequence estimation software (Signal P ver. 2), the signal sequence of heavy chain was estimated to be up to cysteine (C) at position 19 from the N-terminal of SEQ ID NO:73. The N-terminal of the mature form was considered to be glutamic acid (E) at position 20 of SEQ ID NO:73.

<Old6 light chain variable region>
(SEQ ID NO: 74)
AGATCTCTCACCATGGACATGAGGGTCCCCGCTCAGCTCCTGGGGCTTCT

GCTGCTCTGGCTCCCAGGTGCCAGATGTGCCATCCAGTTGACCCAGTCTC

CATCCTCCCTGTCTGCATCTGTAGGAGACAGAGTCACCATCACTTGCCGG

GCAAGTCAGGGCATTAGCAGTGATTTAGCCTGGTATCAGCAGAAACCAGG

GAAAGCTCCTAAGCTCCTGATCTATGATGCCTCCAGTTTGGAAAGTGGGG

TCCCATCAAGGTTCAGCGGCAGTGGATCTGGGACAGATTTCACTCTCACC

ATCAGCAGCCTGCAGCCTGAAGATTTTGCAACTTATTACTGTCAACAGTT

TAATAGTTACCCATTCACTTTCGGCCCTGGGACCAAAGTGGATATCAAAC

GTACGGT

<Old6 light chain variable region>
(SEQ ID NO: 75)
MDMRVPAQLLGLLLLWLPGARCAIQLTQSPSSLSASVGDRVTITCRASQG

ISSDLAWYQQKPGKAPKLLIYDASSLESGVPSRFSGSGSGTDFTLTISSL

QPEDFATYYCQQFNSYPFTFGPGTKVDIKRTVAA

The translation initiation site of the light chain DNA is an ATG codon which starts from adenine (A) at position 13 from the 5'-terminal of SEQ ID NO:74, and a boundary between the variable region and the constant region of the antibody is located between adenine (A) at position 399 and cytosine (C) at position 400 from the 5'-terminal. In the light chain amino acid sequence, the light chain variable region is up to lysine (K) residue at position 129 from the N-terminal of SEQ ID NO:75, and the constant region is on and after arginine (R) at position 130. By a gene sequence estimation software (Signal P ver. 2), the signal sequence of light chain was estimated to be up to cysteine (C) at position 23 from the N-terminal of SEQ ID NO:75. The N-terminal of the mature form was considered to be alanine (A) at position 24 of SEQ ID NO:75.

Each of DNA molecules encoding the heavy chain variable region and the light chain variable region of 7G3 and the amino acid sequences of the heavy chain variable region and light chain variable region was shown in the following.

<7G3 heavy chain variable region>
(SEQ ID NO: 76)
GTCGACCACCATGGGATGGAGCTGGATCTTTCTCTTTCTCGTGTCAGGAA

CTGGAGGTGTCCTCTCTGAGGTCCAGCTGCAACAGTCTGGACCTGAGCTG

GTGAAGCCTGGGGCTTCAGTAAAGATGTCCTGCAAGGCTTCTGGATACAC

CTTCACTGACTACTACATGAAGTGGGTGAAACAGAGCCATGGAAAGAGCC

TTGAGTGGATTGGAGATATTATTCCTAGCAATGGTGCCACTTTCTACAAC

CAGAAGTTCAAGGGCAAGGCCACTTTGACTGTGGACAGATCCTCCAGCAC

AGCCTACATGCACCTCAACAGCCTGACATCTGAGGACTCTGCAGTCTATT

ACTGTACAAGATCGCATTTACTGCGGGCCTCCTGGTTTGCTTACTGGGGC

CAAGGGACTCTGGTCACTGTCTCTGCAGCTAGC

-continued
<7G3 heavy chain variable region>
(SEQ ID NO: 77)
MGWSWIFLFLVSGTGGVLS<u>E</u>VQLQQSGPELVKPGASVKMSCKASGYTFTD

YYMKWVKQSHGKSLEWIGDIIPSNGATFYNQKFKGKATLTVDRSSSTAYM

HLNSLTSEDSAVYYCTRSHLLRASWFAYWGQGTLVTVS<u>A</u>AS

The translation initiation site of the heavy chain DNA is an ATG codon which starts from adenine (A) at position 16 from the 5'-terminal of SEQ ID NO:76, and a boundary between the variable region and the constant region of the antibody is located between adenine (A) at position 427 and guanine (G) at position 428 from the 5'-terminal. In the heavy chain amino acid sequence, the heavy chain variable region is up to alanine (A) residue at position 139 from the N-terminal of SEQ ID NO:77, and the constant region is on and after alanine (A) at position 140. By a gene sequence estimation software (Signal P ver. 2), the signal sequence of heavy chain was estimated to be up to serine (S) at position 19 from the N-terminal of SEQ ID NO:77. The N-terminal of the mature form was considered to be glutamic acid (E) at position 20 of SEQ ID NO:77.

<7G3 light chain variable region>
(SEQ ID NO: 78)
AGATCTCACC<u>ATG</u>GAATCACAGACTCAGGTCCTCATGTCCCTGCTGTTCT

GGGTATCTGGTACCTGTGGGGACTTTGTGATGACACAGTCTCCATCCTCC

CTGACTGTGACAGCAGGAGAGAAGGTCACTATGAGCTGCAAGTCTAGTCA

GAGTCTGTTAAACAGTGGAAATCAAAAGAACTACTTGACCTGGTATCTGC

AGAAACCAGGGCAGCCTCCTAAATTGTTGATCTATTGGGCATCCACTAGG

GAATCTGGGGTCCCTGATCGCTTCACAGGCAGTGGATCTGGAACAGATTT

CACTCTCACCATCAGCAGTGTGCAGGCTGAAGACCTGGCAGTTTATTACT

GTCAGAATGATTATAGTTATCCGTACACGTTCGGAGGGGGGACCAAGCTG

GAAATAAA<u>A</u>CGT

<7G3 light chain variable region>
(SEQ ID NO: 79)
MESQTQVLMSLLFWVSGTCG<u>D</u>FVMTQSPSSLTVTAGEKVTMSCKSSQSLL

NSGNQKNYLTWYLQKPGQPPKLLIYWASTRESGVPDRFTGSGSGTDFTLT

ISSVQAEDLAVYYCQNDYSYPYTFGGGTKLEI<u>K</u>R

The translation initiation site of the light chain DNA is an ATG codon which starts from adenine (A) at position 11 from the 5'-terminal of SEQ ID NO:78, and a boundary between the variable region and the constant region of the antibody is located between adenine (A) at position 409 and cytosine (C) at position 410 from the 5'-terminal. In the light chain amino acid sequence, the light chain variable region is up to lysine (K) residue at position 133 from the N-terminal of SEQ ID NO:79, and the constant region is on and after arginine (R) at position 134. By a gene sequence estimation software (Signal P ver. 2), the signal sequence of light chain was estimated to be up to the glycine (G) at position 22 from the N-terminal of SEQ ID NO:79. The N-terminal of the mature form was considered to be aspartic acid (D) at position 22 of SEQ ID NO:79.

(Preparation of Recombinant Type Antibodies)

Cells expressing a recombinant antibody were prepared by introducing each of the constructed six recombinant antibody expression vectors into a host cell. HEK293F (Invitrogen) was used as a host cell for expression.

Each expression vector was introduced into HEK293F using 293Fectin (Invitrogen). The HEK293F was cultured under conditions of 5% $CO_2$ and 37° C. using a shaker, and the culture supernatant was recovered about 5 days after culturing. The recovered culture supernatant was subjected to affinity purification using rmp Protein A (Amersham-Pharmacia Biotech). PBS as an adsorption buffer and 0.02 M of glycine buffer (pH 3) as an elution buffer, using 0.8x40 cm column (Bio-Rad Laboratories) and the like depending on the amount for the purification. The elution fraction was adjusted to about pH 7.2 by adding 1 M of Tris (pH 9.0). The thus prepared antibody solution was substituted to PBS using a dialysis membrane (10,000 cut, Spectrum Laboratories) and subjected to sterilization by filtration using a membrane filter MILLEX-GV having a pore size of 0.22 μm (Millipore), thereby obtaining a purified human anti-IL-3Rα monoclonal antibody. The concentration of the purified antibody was calculated by measuring absorbance at 280 nm and regarding 1 mg/ml as 1.4 OD.

A summary of amino acid sequences and SEQ ID NOs of each human antibody CDR (complementarity-determining region) was shown in Table 1.

TABLE 1

| | SEQ ID NO CDR 1 CDR 2 CDR 3 | CDR 1 | CDR 2 | CDR 3 |
|---|---|---|---|---|
| Heavy chain variable region | | | | |
| Old4 | 113 114 115 | TYAIS | GIIPIFGIVNYAQKFQG | GGGSGPDVLDI |
| Old5 | 116 117 118 | TYAIS | GLIPIFDIENYAQKFQG | GGGSGPDVLDI |
| Old17 | 119 120 121 | NFAIS | GIIPIFGSTNYAQKFQG | GDKYGPYYFHY |

TABLE 1-continued

| | SEQ ID NO CDR 1 CDR 2 CDR 3 | CDR 1 | CDR 2 | CDR 3 |
|---|---|---|---|---|
| Old19 | 122<br>123<br>124 | SYAIS | GIIPIFGTANYAQKFQG | GHKYGPYYFDY |
| New102 | 125<br>126<br>127 | SYAIS | EIIPIFGIVNYAQKFQG | ETAVAGILGY |
| Old6 | 128<br>129<br>130 | SHNMN | SISSSSSYIYYADSVKG | EDWGYFD |
| Light chain variable region | | | | |
| Old4 | 131, 132, 133 | RMSQGIRSYLA | AASTLQS | QQYYSFPYT |
| Old5 | 134, 135, 136 | RMSQGIRSYLA | AASTLQS | QQYYSFPYT |
| Old17 | 137, 138, 139 | RASQGISSWLA | AASSLQS | QQYNSYPYT |
| Old19 | 140, 141, 142 | RASQGISSWLA | AASSLQS | QQYNSYPRT |
| New102 | 143, 144, 145 | RASQGISSWLA | AASSLQS | QQYNSYPYT |
| Old6 | 146, 147, 148 | RASQGISSDLA | DASSLES | QQFNSYPFT |

Example 5

Purification of Anti-IL-3Rα Human Antibody from Hybridoma Culture Supernatant

A hybridoma was cultured after adapting from the IL-6-containing DMEM medium used in Example 3 to E-RDF medium (Kyokuto Pharmaceutical Industrial Co., Ltd.). An antibody was purified from the culture supernatant. The purification of the antibody was carried out in accordance with Example 4.

Firstly, a hybridoma producing a human anti-IL-3Rα monoclonal antibody was adapted to eRDF medium (Kyokuto Pharmaceutical Industrial Co., Ltd.) containing 10 ng/ml IL-6 and 10% fetal calf serum (FCS: SIGMA). Next, the obtained hybridoma was adapted to eRDF medium (Kyokuto Pharmaceutical Industrial Co., Ltd.) containing bovine insulin (5 µg/ml, GIBCO BRL), human transferrin (5 µg/ml, GIBCO BRL), ethanolamine (0.01 mM, SIGMA), sodium selenite ($2.5 \times 10^{-5}$ mM, SIGMA) and 1% low IgG FCS (Hy-Clone). This adapted hybridoma was cultured in a flask, and the culture supernatant was recovered. The recovered supernatant was subjected to 10 µm and 0.2 µm filters (Gelman Sciences Inc.) to remove useless articles such as a hybridoma and the like. The antibody was purified from the thus recovered supernatant by the same method as Example 4.

Example 6

Calculation of Association and Dissociation Constants Using the Purified Anti-IL-3Rα Human Antibody The association and dissociation constants of the purified anti-IL-3Rα antibody were analyzed using an analyzer which is based on a surface plasmon resonance principal (Biacore, GE Healthcare, hereinafter GE). Briefly, an anti-human antibody or anti-mouse antibody was immobilized on a CM5 sensor tip, then an anti-IL-3Rα human or mouse antibody was applied thereto to allow to bind, then the soluble form of IL-3Rα protein prepared in Example 2 was applied thereto, and the association and dissociation were observed using Biacore 2000. Through the whole test steps, the test method of GE Healthcare for the calculation of association and dissociation constants was basically employed.

Specifically, CM5 (research grade) was used for a sensor tip (each GE). Firstly, the CM5 tip was activated by applying an equivalent mixture of 400 mM EDC (N-ethyl-N'-(3-dimethylaminopropyl)carbodiimidehydrochloride) and 100 mM NHS (N-hydroxysuccinimide) to the CM5 tip. Next, an antibody to the human antibody attached to the Human Antibody Capture Kit (GE) (hereinafter, referred to as anti-human antibody) was diluted with the solution attached to the kit and applied thereto, thereby immobilizing the required amount of the anti-human antibody to the CM5 tip. Regarding the mouse antibody to be used as a control, an antibody to the mouse antibody attached to the Mouse Antibody Capture Kit (GE) (hereinafter, referred to as anti-mouse antibody) was diluted with the solution attached to the kit and applied thereto, thereby immobilizing a necessary amount thereof to the CM5 tip. Next, the surface of the activated tip was blocked and inactivated by applying 1 M of ethanolamine dihydrochloride thereto. By the above steps until this, preparation of a CM5 sensor tip which can measure the dissociation constant $K_D$ was completed.

Next, each of anti-IL-3Rα antibodies, was diluted to give a concentration of 5 µg/ml with HBS-FP buffer (GE) one kind per one flow cell and applied, thereby allowing it to bind to the immobilized anti-human antibody or anti-mouse antibody. Next, the soluble form of IL-3Rα protein was applied thereto.

In order to dissociate the bound anti-IL-3Rα antibody and soluble form of IL-3Rα protein, 3 M $MgCl_2$ attached to Human Antibody Capture Kit or pH 1.7 of Glycine-HCl attached to Mouse Antibody Capture Kit was applied in the amount attached to the kit. The steps until this were regarded as one step. By repeating the same steps using two or more concentrations of the soluble form of IL-3Rα protein, data for calculating association and dissociation constants (sensorgram) were obtained.

The concentration of the soluble form of human IL-3Rα protein applied to a subject was calculated as described in Example 2 by measuring the absorbance at 280 nm and regarding 1 mg/ml as 1.4 OD. The molecular weight of the soluble form of human IL-3Rα protein was calculated as follows. Regarding molecular weight of human IL-3Rα protein, it has been reported that it comprises 360 amino acid residues, has six N-type sugar chain binding sites and the molecular weight is 70 kDa (The Cytokine Facts Book second edition, Academic Press). Accordingly, the molecular weight of the soluble form of human IL-3Rα protein was calculated as about 63 kDa by subtracting molecular weights of the amino acids of the transmembrane region and the intracellular region from 70 kDa known as a reference information and adding, to the resulting value, the molecular weight of the amino acids of the Flag sequence.

In the analysis, Biaevaluation software (GE) was used and Biaevaluation Software Handbook was referred. Specifically, by carrying out simultaneous analysis of kinetics analysis, employing basically the 1:1 Langmuir binding reaction model and fitting, association rate constant (Ka) and dissociation rate constant (Kd) were calculated, and the value of dissociation constant $K_D$ was calculated by the calculation of Kd/Ka.

The results are shown in the following table 2.

TABLE 2

| Antibody name | Ka | Kd | $K_D$ |
|---|---|---|---|
| Human antibodies | | | |
| Old4 | $3.88 \times 10^5$ | $5.15 \times 10^{-4}$ | $1.33 \times 10^{-9}$ |
| Old5 | $7.17 \times 10^5$ | $4.72 \times 10^{-4}$ | $6.58 \times 10^{-10}$ |
| Old17 | $2.08 \times 10^5$ | $2.98 \times 10^{-4}$ | $1.43 \times 10^{-9}$ |
| Old19 | $1.54 \times 10^5$ | $4.99 \times 10^{-4}$ | $3.24 \times 10^{-9}$ |
| New102 | $6.02 \times 10^5$ | $4.80 \times 10^{-4}$ | $7.98 \times 10^{-10}$ |
| Old6 | $1.71 \times 10^6$ | $2.15 \times 10^{-5}$ | $1.26 \times 10^{-9}$ |
| Chimeric antibody | | | |
| 7G3 | $2.48 \times 10^5$ | $4.66 \times 10^{-4}$ | $1.88 \times 10^{-9}$ |
| Mouse antibodies | | | |
| 7G3 | $1.68 \times 10^5$ | $9.52 \times 10^{-5}$ | $5.66 \times 10^{-10}$ |
| 9F5 | $7.13 \times 10^4$ | $6.5 \times 10^{-5}$ | $9.11 \times 10^{-10}$ |
| 107D2.08 | $4.16 \times 10^5$ | $2.03 \times 10^{-5}$ | $4.88 \times 10^{-8}$ |
| AC145 | $7.66 \times 10^4$ | $4.26 \times 10^{-5}$ | $5.57 \times 10^{-8}$ |
| L-16 | $8.13 \times 10^5$ | $4.16 \times 10^{-5}$ | $5.12 \times 10^{-9}$ |

Example 7

Epitope Analysis of Anti-Human IL-3Rα Human Antibody (Preparation of IL-3Rα/GM-CSFRα Chimeric Protein Expression Cell)

In order to carry out epitope analysis of IL-3Rα antibody, a chimeric protein in which a portion of the extra-membrane region of IL-3Rα was replaced by GM-CSFRα was expressed in a cell, and binding activity of each anti-IL-3Rα antibody to the cell was analyzed. In brief, firstly, the IL-3Rα molecule and GM-CSFRα molecule were divided into three regions (A, B and C domains from the above-mentioned N-terminal), secondly vectors which express molecules in which each of the A, B and C domains of the IL-3Rα molecule was replaced by the corresponding domain of GM-CSFRα molecule were respectively constructed, thirdly, these were forcedly expressed in HEK293F cell, and fourthly, whether or not each anti-IL-3Rα antibody labeled with a fluorescence dye binds thereto was observed by flow cytometry.

(Preparation of GM-CSFR/pEF6/Myc-HisC Plasmid DNA)

A cDNA of human GM-CSFR receptor a chain (GM-CSFRα, CD116) was amplified from a spleen-derived cDNA (CLONTECH Human MTC Panel) by a PCR method using KOD-Plus-Ver. 2 (Toyobo Co., Ltd.). As a PCR device, Gene-Amp PCR System 9700 (Applied Biosystems) was used. Regarding the PCR, after a denaturation step at 94° C. for 2 minutes, a three step reaction at 98° C. 10 seconds-55° C. 30 seconds-68° C. 75 seconds was carried out 35 cycles. The PCR primers used are as follows.

```
hCD116Fw-MfeI:
                                  (SEQ ID NO: 80)
5'-CGGCAATTGCCACCATGCTTCTCCTGGTGACAAGCCT-3' hCD116Rv-NotI:
                                  (SEQ ID NO: 81)
5'-ATTGCGGCCGCTCAGGTAATTTCCTTCACGG-3'
```

The thus obtained PCR products were subjected to 0.8% agarose gel electrophoresis (TAE buffer). DNA was visualized by ethidium bromide staining. A band of at around 1.2 kb was cut out, and the DNA was extracted using JETsorb Kit (Genomed, Bad Oeynhausen, Germany) and then digested with NotI and MfeI. A pEF6/Myc-HisC plasmid DNA (Invitrogen) was digested with EcoRI and NotI. Each DNA was subjected to 0.8% agarose gel electrophoresis and bands of at around 1.2 kb and around 6 kb were cut out, and the DNA molecules were extracted using JETsorb Kit (Genomed, Bad Oeynhausen, Germany). Then, 0.5 µl of a pEF6/Myc-HisC plasmid DNA-derived DNA solution and 4 µl of a PCR product-derived DNA solution were mixed and subjected to ligation using TaKaRa Ligation Kit (TAKARA BIO INC.). Regarding the transformation, a ligation sample and DH5 alpha competent cells were mixed and spread on an LB plate. Insertion check was carried out by colony direct PCR using LA Taq (TAKARA BIO INC.). Regarding the PCR, after a denaturation step at 94° C. for 5 minutes, a three step reaction at 94° C. 30 seconds-55° C. 30 seconds-72° C. 2 minutes was carried out 40 cycles and then a treatment at 99° C. for 30 minutes was carried out.

The PCR primers used were as follows.

```
hCD116Fw-MfeI:
                                  (SEQ ID NO: 82)
5'-CGGCAATTGCCACCATGCTTCTCCTGGTGACAAGCCT-3' hCD116Rv-NotI:
                                  (SEQ ID NO: 83)
5'-ATTGCGGCCGCTCAGGTAATTTCCTTCACGG-3'
```

The thus obtained PCR products were subjected to 0.8% agarose gel electrophoresis (135 V, 15 minutes, TAE buffer). DNA was visualized by ethidium bromide staining. Using a colony from which amplification of around 1.2 kb was obtained, nucleotide sequence was determined by a direct sequencing method. In the reaction of sequence samples, BigDye(R) Terminator v3.1 Cycle Sequencing Kit (Applied Biosystems) and GeneAmp PCR System 9700 (Applied Biosystems) were used (these were used in the all DNA sequence analyses in this specification). The PCR primers used are as follows.

```
hCD116Rv-NotI:
                                      (SEQ ID NO: 85)
5'-ATTGCGGCCGCTCAGGTAATTTCCTTCACGG-3' hCD116SeqFw1:
                                      (SEQ ID NO: 86)
5'-TGAACTGTACCTGGGCGAGG-3' hCD116SeqFw2:
                                      (SEQ ID NO: 87)
5'-CTGGCACGGAAAACCTACTG-3' hCD116SeqRv1:
                                      (SEQ ID NO: 88)
5'-CCTGAATTTGGATAAAGCAG-3'
```

ABI 3700XL DNA analyzer (Applied Biosystems) was used as a sequence analyzing device (this was used in the all DNA sequence analyses in this specification). By selecting a clone in which mutation in the amino acid sequence by PCR was not found, plasmid DNA was extracted by Largeprep method (QIAGEN).

(Preparation of IL-3RA-FLAG/pEGFP-N1)

The full length cDNA of human IL-3Rα (CD123) was amplified by PCR and FLAG tag was linked to its downstream (IL-3RA-FLAG/pEGFP-N1).

Human IL-3RA cDNA was amplified by a PCR method using hCD123/pEGFP-N1 plasmid DNA as a template and LA Taq (TAKARA BIO INC.). Regarding the PCR, after a denaturation step at 95° C. for 30 seconds, a three step reaction at 95° C. 15 seconds-56° C. 15 seconds-72° C. 60 seconds was carried out 10 cycles and then 2 minutes of an elongation reaction was carried out. The PCR primers used are as follows.

```
T7:
                                      (SEQ ID NO: 89)
5'-TAATACGACTCACTATAGGG-3' hCD123-C-FLAG-R1:
                                      (SEQ ID NO: 90)
5'-TCGTCATCGTCCTTGTAGTCAGTTTTCTGCACGACCTGTA-3'
```

Using 2 μl of the PCR product as a template, amplification was carried out by a PCR method using LA Taq (TAKARA BIO INC.). Regarding the PCR, after a denaturation step at 95° C. for 1 minute, a three step reaction at 95° C. 15 seconds-56° C. 15 seconds-72° C. 60 seconds was carried out 15 cycles and then an elongation reaction at 72° C. for 2 minutes was carried out. The PCR primers used are as follows.

```
IL-3Rα_Fw:
                                      (SEQ ID NO: 91)
5'-CGGCAATTGCCACCATGGTCCTCCTTTGGCTCAC-3'

C-FLAG-NotR2:
                                      (SEQ ID NO: 92)
5'-AAAAGCGGCCGCTCACTTGTCGTCATCGTCCTTGTAGTC-3'
```

The thus obtained PCR products were subjected to 0.8% agarose gel electrophoresis (135 V, 15 minutes, TAE buffer). DNA was visualized by ethidium bromide staining. A band of at around 1 kb was cut out, and the DNA was extracted using Wizard SV Gel and PCR Clean-Up System. The whole amount of the extracted DNA was digested with MfeI and NotI and subjected to 0.8% agarose gel electrophoresis (135 V, 15 minutes, TAE buffer). DNA was visualized by ethidium bromide staining. A band of at around 1 kb was cut out, and the DNA was extracted using Wizard SV Gel and PCR Clean-Up System. Then, 5 μl of the thus extracted IL-3RA-FLAG cDNA and 1 μl of the pEGFP-N1 plasmid DNA which had been cleaved with EcoRI and NotI were mixed and ligated using TaKaRa Ligation Kit (TAKARA BIO INC.). Regarding the transformation, a ligation sample and DH10B competent cells were mixed and spread on an LB plate (containing kanamycin). Insertion check was carried out by colony direct PCR using LA Taq (TAKARA BIO INC.). Regarding the PCR, after a denaturation step at 95° C. for 1 minute, a three step reaction at 95° C. 15 seconds-56° C. 15 seconds-72° C. 60 seconds was carried out 35 cycles and then an elongation reaction at 72° C. for 2 minutes was carried out. The PCR primers used are as follows.

```
                                      (SEQ ID NO: 93)
pEGFP-N1-Fw:   5'-CGTGTACGGTGGGAGGTCTA-3'

(SEQ ID NO: 94)
pEGFP-N1-Re:   5'-TTTATGTTTCAGGTTCAGG-3'
```

A plasmid DNA was extracted by a Miniprep method from a colony in which amplification of around 0.8 kb was obtained.

It was found by a DNA sequence analysis that the purified IL-3RA-FLAG/pEGFP-N1 plasmid DNA does not have a mutation caused by the PCR and that the FLAG tag is present therein. The primers used in the DNA sequence analysis are as follows.

```
                                      (SEQ ID NO: 95)
pEGFP-N1-Fw:   5'-CGTGTACGGTGGGAGGTCTA-3'

(SEQ ID NO: 96)
pEGFP-N1-Re:   5'-TTTATGTTTCAGGTTCAGG-3'
```

(Domain Mapping of IL-3Rα)

As a result of BLASTP search (database: Protein Data Bank proteins (pdb)), IL-13 receptor alpha chain (IL-13Rα) was hit with the highest score (PDB: 3BPNC; Chain C, Crystal Structure of the I14-I14r-I113ra Ternary Complex). Using the PDB file down-loaded from Protein Data Bank and a graphic software RasMol, three-dimensional structure of the IL-13Rα protein was visualized and three domains constituting the extracellular region (the above-mentioned A, B and C domains) were divided. Using a Multiple Alignment software MUSCLE, IL-3Rα amino acid sequence and IL-13Rα amino acid sequence were compared and IL-3Rα extracellular region was also divided into three domains. Further, GM-CSFRα and IL-3Rα were compared in the same manner and GM-CSFRα extracellular region was also divided into three domains.

In order to assign epitopes of anti-human IL-3Rα human antibodies, proteins in which each of the three domains of IL-3Rα was replaced one by one by said domains of GM-CSFRα were prepared and expressed on the cell membrane and the presence or absence of antibody binding was confirmed.

Using the IL-3RA-FLAG/pEGFP-N1 plasmid DNA as a template, amplification was carried out by a PCR method which uses PrimeSTAR(R)HS DNA Polymerase (TAKARA BIO INC.). Regarding the PCR, a two step reaction at 98° C. 10 seconds-68° C. 6 minutes was carried out 25 cycles. The PCR primers used are as follows.

A domain deficiency;

```
                                    (SEQ ID NO: 97)
CD123R11pEGFPN1:   AAAGGTACCGAATTCGAAGCTTGAGCTC (SEQ ID NO: 98)
CD123F11:          AAAGGTACCGGGAAGCCTTGGGCAGGT
```

B domain deficiency;

```
                                    (SEQ ID NO: 99)
CD123R12-2:        AAAGGTACCACTGTTCTCAGGGAAGAGGAT (SEQ ID NO: 100)
CD123F12-2:        AAAGGTACCCAGATTGAGATATTAACTCC
```

C domain deficiency;

```
                                    (SEQ ID NO: 101)
CD123R13:          AAAGGTACCTGAAAAGACGACAAACTT (SEQ ID NO: 102)
CD123F13:          AAAGGTACCTCGCTGCTGATCGCGCTG
```

The thus obtained PCR product was subjected to 0.8% agarose gel electrophoresis (135 V, 15 minutes, TAE buffer). DNA was visualized by ethidium bromide staining. After confirming the amplification, this was purified using Wizard SV Gel and PCR Clean-Up System. The thus obtained DNA was digested with KpnI and DpnI, purified using Wizard SV Gel and PCR Clean-Up System and ligated using TaKaRa Ligation Kit. Regarding the transformation, a ligation sample and DH10B competent cells were mixed and spread on an LB plate (containing kanamycin). Insert check was carried out by colony direct PCR using LA Taq (TAKARA BIO INC.). Regarding the PCR, after a denaturation step at 95° C. for 1 minute, a three step reaction at 95° C. 15 seconds-56° C. 15 seconds-72° C. 40 seconds was carried out 38 cycles and then an elongation reaction at 72° C. for 2 minutes was carried out. The PCR primers used are as follows.

```
                                    (SEQ ID NO: 103)
pEGFP-N1-Fw:       5'-CGTGTACGGTGGGAGGTCTA-3'

(SEQ ID NO: 104)
pEGFP-N1-Re:       5'-TTTATGTTTCAGGTTCAGG-3'
```

The thus obtained PCR product was subjected to 0.8% agarose gel electrophoresis (135 V, 15 minutes, TAE buffer). DNA was visualized by ethidium bromide staining. A plasmid DNA was extracted by the Miniprep method from a colony in which amplification at around 1 kb was obtained.

Using the GM-CSFR/pEF6/Myc-His C plasmid DNA as a template, amplification was carried out by a PCR method which uses PrimeSTAR(R)HS DNA Polymerase (TAKARA BIO INC.). Regarding the PCR, a two step reaction at 98° C. 10 seconds-68° C. 30 seconds was carried out 25 cycles. The PCR primers used are as follows.

A domain insertion;

```
                                    (SEQ ID NO: 105)
GM-CSFRF11:        AAAGGTACCGCCACCATGCTTCTCCTGGTGACA (SEQ ID NO: 106)
GM-CSFRR11:        AAAGGTACCTGAATTTGGATAAAGCAG
```

B domain insertion;

```
                                    (SEQ ID NO: 107)
GM-CSFRF12:        AAAGGTACCGGAAGGGAGGGTACCGCT (SEQ ID NO: 108)
GM-CSFRR12:        AAAGGTACCCTTTGTGTCCAAAAGTGA
```

C domain insertion;

```
                                    (SEQ ID NO: 109)
GM-CSFRF13:        AAAGGTACCAAAATAGAACGATTCAAC (SEQ ID NO: 110)
GM-CSFRR13:        AAAGGTACCAATGTACACAGAGCCGAG
```

The thus obtained PCR product was subjected to 0.8% agarose gel electrophoresis (135 V, 15 minutes, TAE buffer). DNA was visualized by ethidium bromide staining. After confirming the amplification, this was purified using Wizard SV Gel and PCR Clean-Up System.

The thus obtained DNA was digested with KpnI and then purified using QIAquick Gel Extraction Kit (QIAGEN), mixed with IL-3RA-FLAG/pEGFP-N1 plasmid DNA in which the corresponding domain was deleted (already cleaved with KpnI and purified) and ligated using TaKaRa Ligation Kit. Regarding the transformation, a ligation sample and DH10B competent cells were mixed and spread on an LB plate (containing kanamycin). Insert check was carried out by colony direct PCR using LA Taq (TAKARA BIO INC.). Regarding the PCR, after a denaturation step at 95° C. for 1 minute, a three step reaction at 95° C. 15 seconds-56° C. 15 seconds-72° C. 40 seconds was carried out 38 cycles and then an elongation reaction at 72° C. for 2 minutes was carried out. The PCR primers used are as follows.

```
                                    (SEQ ID NO: 111)
pEGFP-N1-Fw:       5'-CGTGTACGGTGGGAGGTCTA-3'

(SEQ ID NO: 112)
pEGFP-N1-Re:       5'-TTTATGTTTCAGGTTCAGG-3'
```

The thus obtained PCR product was subjected to 0.8% agarose gel electrophoresis (135 V, 15 minutes, TAE buffer). DNA was visualized by ethidium bromide staining. A plasmid DNA was extracted by the Miniprep method from a colony in which amplification at around 1 kb was obtained.

(Labeling of Anti-IL-3Rα Human Antibody with Fluorescence Dye)

In order to determine binding activity of anti-human IL-3Rα human antibodies, each human antibody was labeled with a fluorescence dye AlexaFlour488 (Molecular Probe, Invitrogen). Regarding the labeling method, it was carried out in accordance with the manual provided by Invitrogen, and regarding the detection, fluorescence was detected by FL1 of a flow cytometry (FACS Calibur, BD Biosciences).

Specifically, 1/10 volume of 1 M $Na_2CO_3$ was added to an antibody solution dissolved in PBS. Next, a predetermined amount of the antibody solution described in the manual was added to a container containing powder of AlexaFlour488 to which tetrafluorophenyl (TFP) had been added, and allowed to undergo the reaction in the dark at room temperature for 1 hour while stirring. Next, after a gel filtration column (NAP-10 and the like, GE Healthcare) was sufficiently substituted with PBS, the solution of antibody reacted with AlexaFlour488 was added thereto while the buffer of the antibody solution was substituted with PBS. An antibody fraction which showed yellow green was obtained. Regarding the AlexaFlour488-labeled anti-human IL-3Ra antibody obtained in the above manner, the absorbances at wavelengths of 280 nm and 494 nm (A280 and A494, respectively) were measured using a spectrometer, and the antibody concentration was calculated by the following calculation formula.

Antibody concentration (mg/ml)=(A280−A494×0.11)/1.4

(Flow Cytometry Analysis of IL-3Rα/GM-CSFRα Chimeric Protein Expression Cell Using Labeled Anti-IL-3Rα Antibody)

HEK293T cell (ATCC CRL 1268) was used for the preparation of the IL-3Rα/GM-CSFRα chimeric protein expression cell. Using 293Fectin (Invitrogen), the plasmid DNA obtained in the above was introduced as an expression vector into the HEK293T. The HEK293T to which the expression vector was introduced was cultured using a shaker under conditions of 5% $CO_2$ and 37° C. after 2 days of the introduction, the obtained protein was used for in the flow cytometry analysis.

From 100,000 to 1,000,000 cells of the chimeric protein expression cell were allowed to react for 30 minutes on ice with at a concentration of 1 μg/ml with an AlexaFlour488-labeled human antibody or a commercially available FITC-labeled anti-IL-3Rα mouse antibody (7G3 or 9F5: both from BD Biosciences, 6H6: Acris Antibodies, AC145: Milteny Biotech, 107D2.08: Dendritics). A staining medium (Dulbecco's PBS supplemented with 2% fetal bovine serum, 2 mM EDTA and 0.05% $NaN_3$) was used for the dilution of antibodies and cells. Next, the cells reacted with antibodies were washed three times with the staining medium and whether the labeled antibody bound to the cell was confirmed by flow cytometry.

Figure 2:
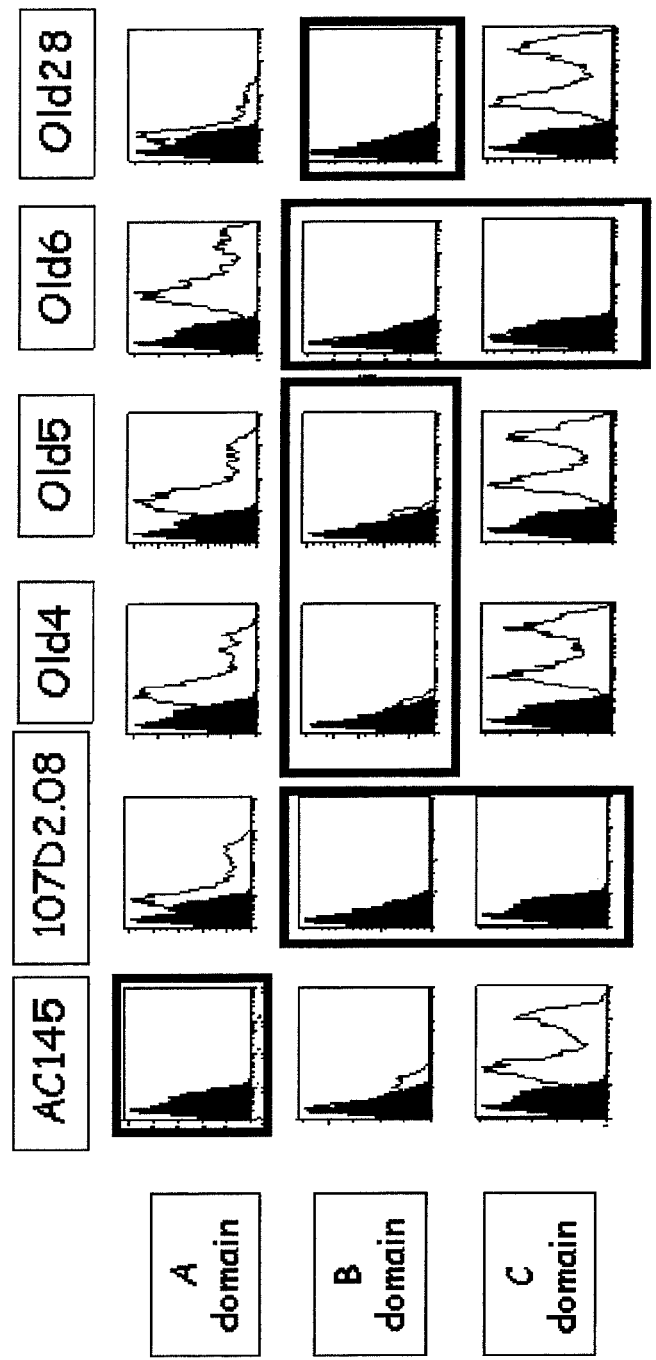

The results are shown in FIGS. 1 and 2. Reactions of 7G3, 9F5, 6H6 and AC145 antibodies disappeared only in the cells expressing a protein in which A domain was replaced by GM-CSFRα. On the other hand, reactions of Old4, Old5, Old19 and New102 antibodies disappeared in the cells expressing a protein in which B domain was replaced by GM-CSFRα. Regarding Old19, its reaction with the cells expressing a protein in which A domain was replaced by GM-CSFRα also disappeared. Regarding the Old6 and 107D2.08, their reaction to B domain- and C domain-substituted protein expression cells disappeared.

Based on the above, it was shown a possibility that 7G3, 9F5, 6H6 and AC145 recognized A domain, and Old4, Old5 and New102 recognized B domain, Old19 recognized A domain and B domain, and Old6 and 107D2.08 recognized B domain and C domain. Accordingly, the reactivity of various anti-IL-3Rα antibodies to A to C domains of IL-3Rα was as the following Table 3.

various IL-3Rα antibodies and a human serum-derived IgG as a negative control antibody were diluted with the TF-1 medium, transferred to the 96-well plate and added in such a manner that final concentration of each antibody gave a final concentration of 10 or 100 μg/ml. As a control, a well of cell-free medium alone and a well to which the TF-1 cell was added were prepared. After 3 days of culturing under an environment of 37° C. and 5% $CO_2$, CelltiterGlo (Promega) was added thereto in an amount equivalent to the medium. After 30 minutes of still standing, the emission was determined using a plate reader (ARBO, Perkin Elmer).

For the growth inhibition ratio, the following calculation was carried out.

(emission of sample−well with no cells)/(well to which TF-1 cell alone was added−well with no cells)×100(%)

Regarding the commercially available antibodies 9F5, 6H6 and 107D2.08, an NAP-5 column was used for the purpose of substituting the buffer with PBS. Specifically, 0.5 ml of an antibody solution was added to the NAP-5 column sufficiently substituted with PBS. Next, by adding 1.0 ml of PBS, the solution discharged from the column was recovered. By carrying out sterilization by filtration using a membrane filter MILLEX-GV (Millipore) having a pore size of 0.22 μm, an antibody dissolved in PBS as a solvent was obtained.

Figure 5:
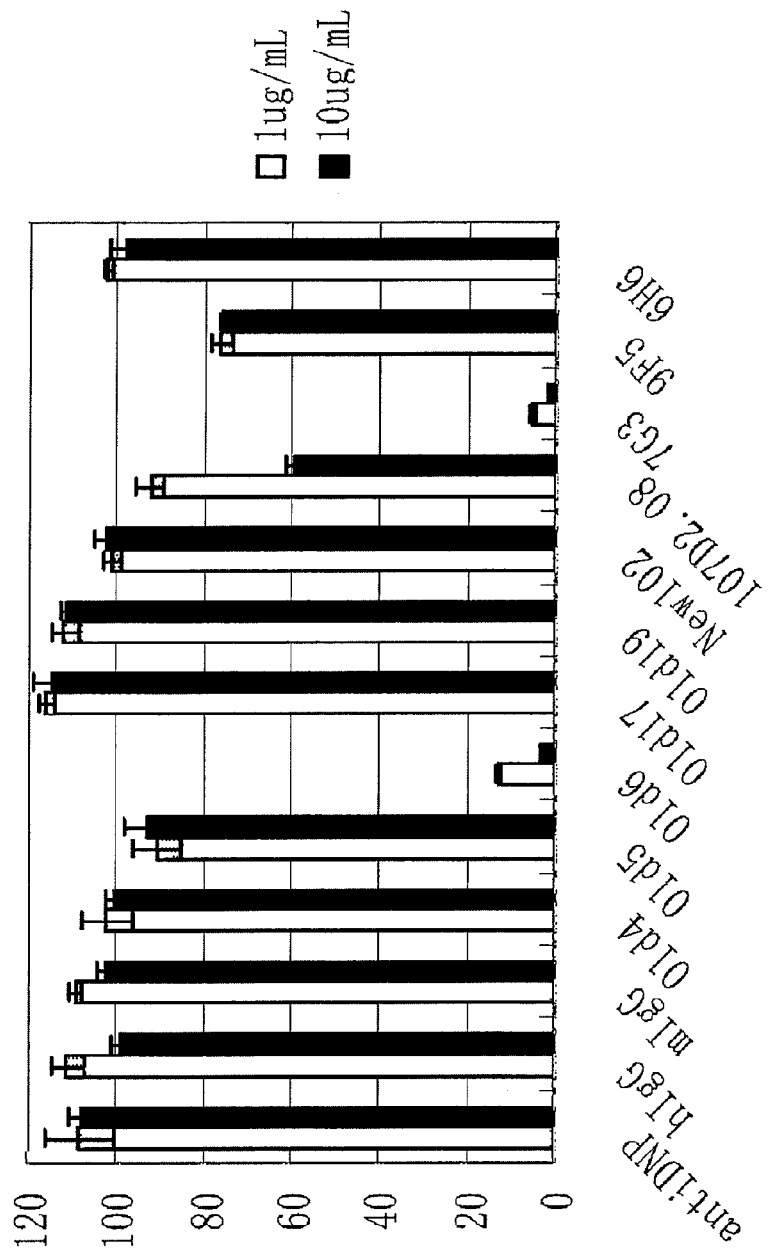
FIG. 5 is a result of a cell growth test for examining blocking activity of IL-3 signaling. The ordinate represents the cell growth inhibition ratio (%) and the abscissa represents various IL-3Rα antibody names.

The results are shown in FIG. 5. It was found that the antibody Old4, antibody Old5, antibody Old17, antibody Old19, antibody New102, antibody 9F5 and antibody 6H6 did not inhibit the IL-3 signaling, and on the other hand, it was found that the antibody 7G3, antibody Old6 and antibody 107D2.08 inhibited IL-3 signaling.

Example 9

Examination of Influence Upon Colony Forming Ability Using Anti-IL-3Rα Human Antibody A colony assay was carried out to find whether various IL-3Rα antibodies have effects upon the colony forming ability by hematopoietic precursor cells.

In brief, 400 cells/ml of cord blood-derived CD34 positive cell (AllCells) was added to a Methocult medium (Stem Cell

TABLE 3

| | 7G3 | 9F5 | 6H6 | AC145 | 107D2.08 | Old19 | New102 | Old4 | Old5 | Old6 | Old28 |
|---|---|---|---|---|---|---|---|---|---|---|---|
| No substitution | ++ | ++ | ++ | ++ | ++ | ++ | ++ | ++ | ++ | ++ | ++ |
| A domain substitution | − | − | − | − | ++ | − | ++ | ++ | ++ | ++ | + |
| B domain substitution | ++ | ++ | ++ | + | − | − | − | − | − | − | − |
| C domain substitution | ++ | ++ | ++ | ++ | − | ++ | ++ | ++ | ++ | − | ++ |

Example 8

Analysis of IL-3 Signaling Blocking Activity of Anti-IL-3Rα Antibodies

In order to examine whether the thus obtained IL-3Rα antibodies inhibit IL-3 signaling, a cell line TF-1 (DMSZ no. ACC344) which grows IL-3- or GM-CSF-dependently was used. Specifically, the TF-1 cell was diluted with RPMI 1640 medium containing 1 ng/ml of IL-3 and 10% fetal calf serum (TF-1 medium) and dispensed on a 96-well plate. Further, Technologie) supplemented with erythropoietin, IL-3, G-CSF and Stem Cell Factor, and the number of colonies was measured 14 days to 16 days thereafter. The colonies were counted by dividing them into a granulocyte/macrophage system colony (CFU-GM), an erythroid system colony (BFU-E) and mixed colonies (CFU-Mix or CFU-GEMM). Regarding the classification method of colony types, a manual provided by Stem Cell Technologie or various textbooks on hematology was used as references.

As the antibodies, each of the chimeric 7G3 antibody as an antibody in which IL-3 signaling blocking activity was found in Example 8 and the New102 antibody as an antibody in which the blocking activity was not found was used.

Figure 6:
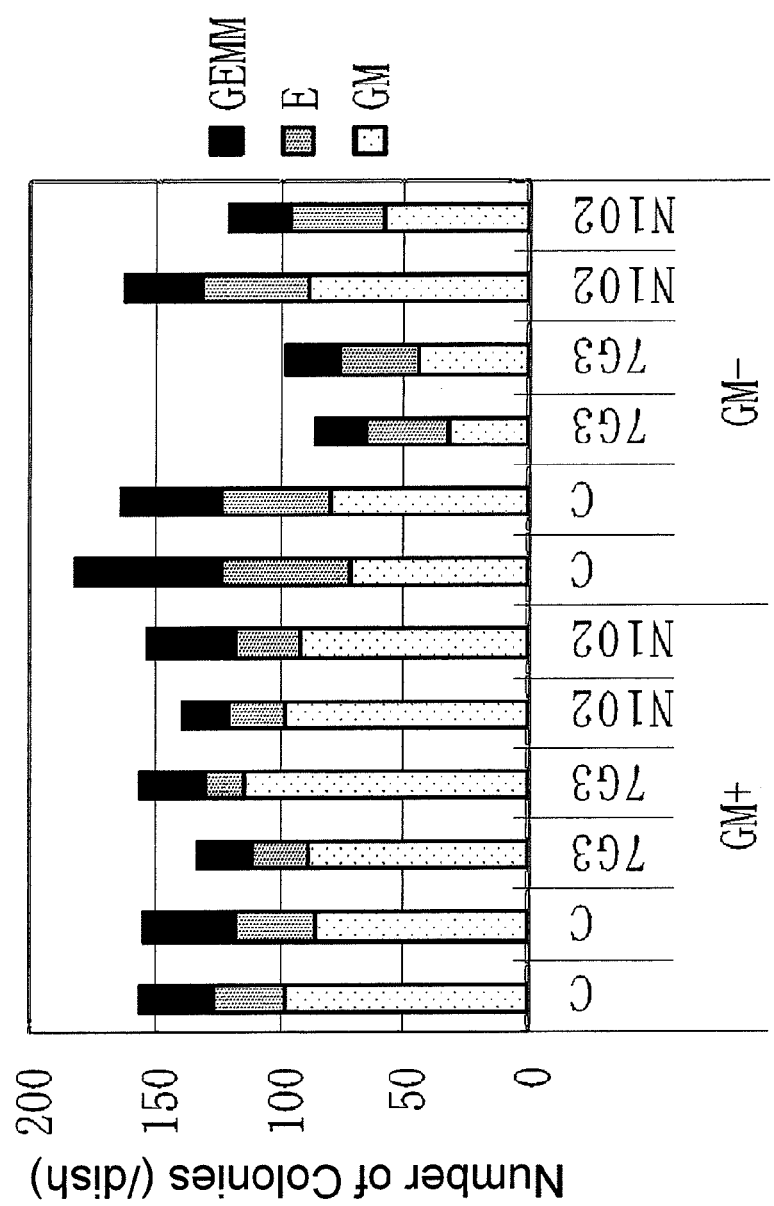
FIG. 6 is a result of a colony assay test for examining blocking activity of IL-3 signaling. GM, E, and GEMM show results using Granulocyte/Macrophage system, Erythroid system colony and mixed colonies, respectively.

The results are shown in FIG. 6. In the colony assay in which erythropoietin, IL-3, G-CSF and Stem Cell Factor were added, decrease in the number of colonies and decrease in the colony size were found by the addition of the 7G3 antibody which had the blocking activity of IL-3 signaling. On the other hand, change in the number of colonies by the addition of the New102 antibody was not found. Based on this result, it is considered that the influence upon the normal hematopoietic function is small and side effects are few when the IL-3 signaling is not inhibited or blocked.

Example 10

Antitumor Effect in a Mouse Tumor Bearing Model Using Anti-IL-3Rα Human Antibody The thus obtained anti-IL-3Rα antibody was administered to mouse tumor bearing model and its antitumor effect was examined. In brief, a leukemia cell was transferred into a mouse through its caudal vein, the antibody was administered thereto on the next day, and about 3 weeks thereafter, the number of leukemia cells in bone marrow cells collected from a bone of the mouse was counted.

Specifically, 0.01 ml equivalent of anti-asialoGM1 antiserum (Wako Pure Chemical Industries, Ltd.) was diluted with physiological saline and administered to SCID mouse (CLEA Japan Inc.) (Day −1). On the next day, 500,000 cells of a cell line of acute myeloid leukemia, MOLM13 (ATCC), were transplanted through caudal vein (Day 0). Further on the next day (Day 1), 10 μg of the anti-IL-3Rα antibody was intraperitoneally administered. The mouse was sacrificed on Day 21, bone marrow was collected from thighbones and shinbones and the bone marrow cells were stained with FITC-labeled human CD45 antibody and PE-labeled anti-IL-3Rα (both from BD Biosciences). Specifically, the antibody was added to about 1,000,000 cells of the bone marrow cell, to give a final concentration of 1 μg/ml for each and allowed to stand still on ice for 30 minutes under shade. Thereafter, the cells stained with the antibody was washed 3 times using a staining medium (a solution prepared by adding 2% fetal bovine serum, 0.05% sodium azide and 2 mM EDTA to PBS (GIBCO)), and a human CD45 positive and human IL-3Rα positive cell was detected by a flow cytometry (FACSCalibur, BD Biosciences). Also, at the time of collecting mouse bone marrow, the number of bone marrow cells was counted using TURK solution. Further, the absolute number of the MOLM13 cells contained in one thighbone was counted by simultaneously adding quantified fluorescent beads (Flow-Count, Beckman Coulter) at the time of the above-mentioned antibody staining.

Figure 7:
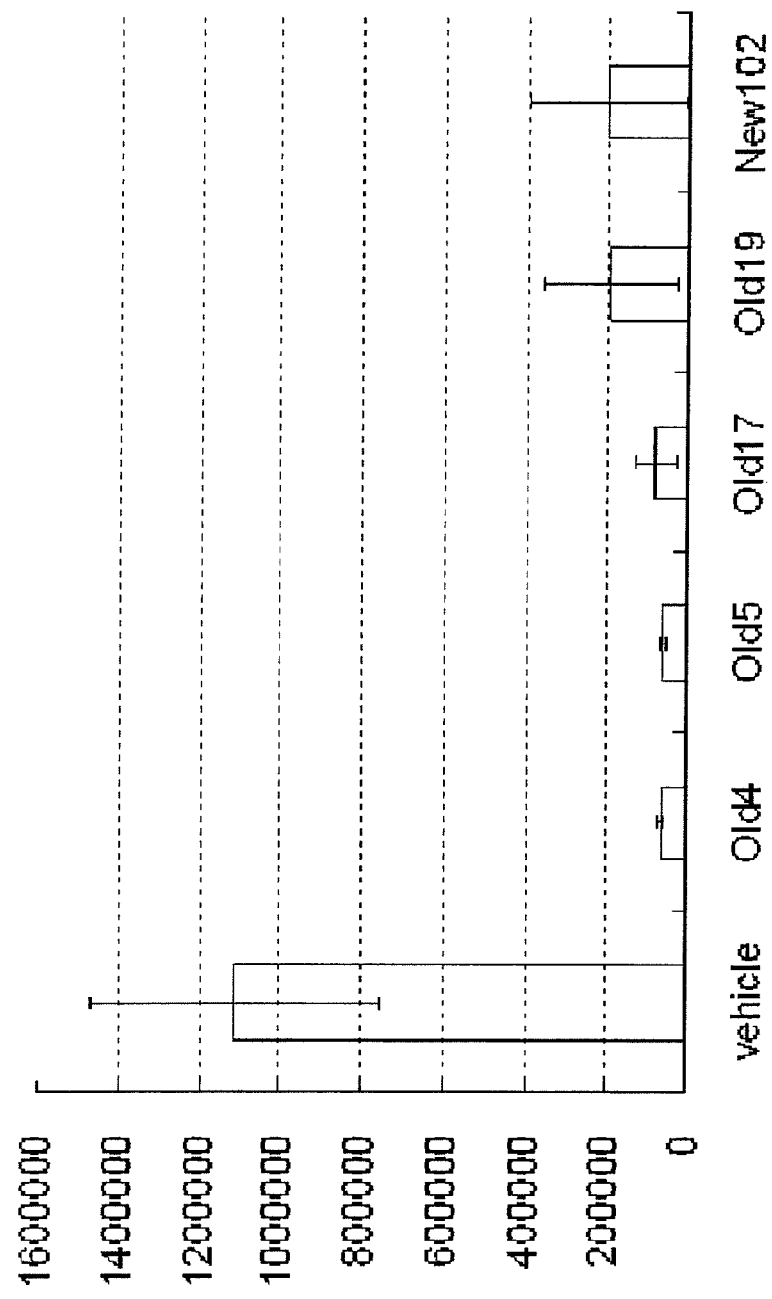
FIG. 7 is a result of examining anti-tumor effects of various human antibodies in a tumor bearing model. The ordinate represents the number of MOLM13 cells, and the abscissa represents the various IL-3Rα antibody names.

The results are shown in FIG. 7. It was found that the number of MOLM13 cells in the thighbone bone marrow in each antibody administered group is markedly reduced in comparison with the Vehicle group to which the antibody was not administered. This result shows that the anti-IL-3Rα antibody has a possibility as a therapeutic agent for leukemia.

Example 11

Toxicity Test of IL-3Rα Expression Cell by Anti-IL-3Rα Antibody

In order to measure antibody-mediated cytotoxicity (antibody-dependent cellular cytotoxicity, hereinafter referred to as ADCC), this was carried out in the presence of antibody using a human peripheral blood mononuclear cells (peripheral blood mononuclear cells, hereinafter PBMC) as an effector.

Peripheral blood was collected from a healthy volunteer and an anticoagulant was added thereto. The blood was put statically on Ficoll-Plaque Plus (GE Healthcare) such that the interface was not disturbed and centrifuged at 2,000 rpm for 20 minutes using a large centrifuge (CF9RX, Hitachi, Ltd.) The intermediate layer containing the cells was collected and washed with PBS, platelets were removed by centrifugation at 900 rpm for 20 minutes, and the peripheral blood-derived mononuclear cells (PBMC) were used as an effector.

Further, PBMC cultured overnight under conditions of 37° C. and 5% $CO_2$ using RPMI 1640 medium containing 10% fetal bovine serum to which human IL-2 (Peprotech) was added to a final concentration of 4 ng/ml (40 IU/ml or more) was also used as an effector of ADCC assay.

In the method, in simple, a target cell is cultured in the presence of an antibody and PBMC and the lysis rate of specific target cell by the antibody is measured.

The following "Colon-26/hCD123 ADCC assay method" was used for the measurement of the lysis rate. Specifically, a target cell was labeled with $^{51}Cr$ by culturing the IL-3Rα forced expression Colon-26 cell as a target cell at 37° C. for 1 hour in the presence of 5% $CO_2$, together with sodium chromate labeled with a radioisotope $^{51}Cr$ ($Na_2{}^{51}CrO_4$, Perkin Elmer, NEZ030S). The labeled target cell was washed 3 times to remove excess $^{51}Cr$ and then suspended in the medium and transferred to a 96-well plate to which antibodies had been added in advance at various concentrations. PBMC was suspended in the medium and transferred to the plate to which the target cell and antibodies had been added (effector/target ratio=100). As the antibodies, the anti-IL-3Rα antibody purified in Example 4 was used, and human serum-derived IgG (SIGMA) as a negative control. As various controls, a well of the medium and target cell alone, a well of PBMC and target alone and a well supplemented with Triton-X were prepared. The 96-well plate filled with mixed solutions was cultured at 37° C. for 4 hours in the presence of 5% $CO_2$.

After centrifugation of the plate, 50 μl of each supernatant was transferred to a scintillator-containing 96-well plate (Lumaplate-TM, Perkin Elmer) and dried at 56° C. for 2 hours. The plate was sealed (TopSeal-A, Packard) and measured using a microplate reader (TopCount, Perkin Elmer).

Regarding the lysis rate of the target cell, amount of $^{51}Cr$ in the sodium chromate released into the medium due to the lysis of cells was measured. That is, the "specific lysis rate" was calculated by dividing a value obtained by subtracting the value of a well to which the antibody was not added from the value of each well, by a value obtained by subtracting the value of a well to which the antibody was not added from the value of a well to which Triton-X was added (specific lysis rate is set to 100%).

Figure 8:
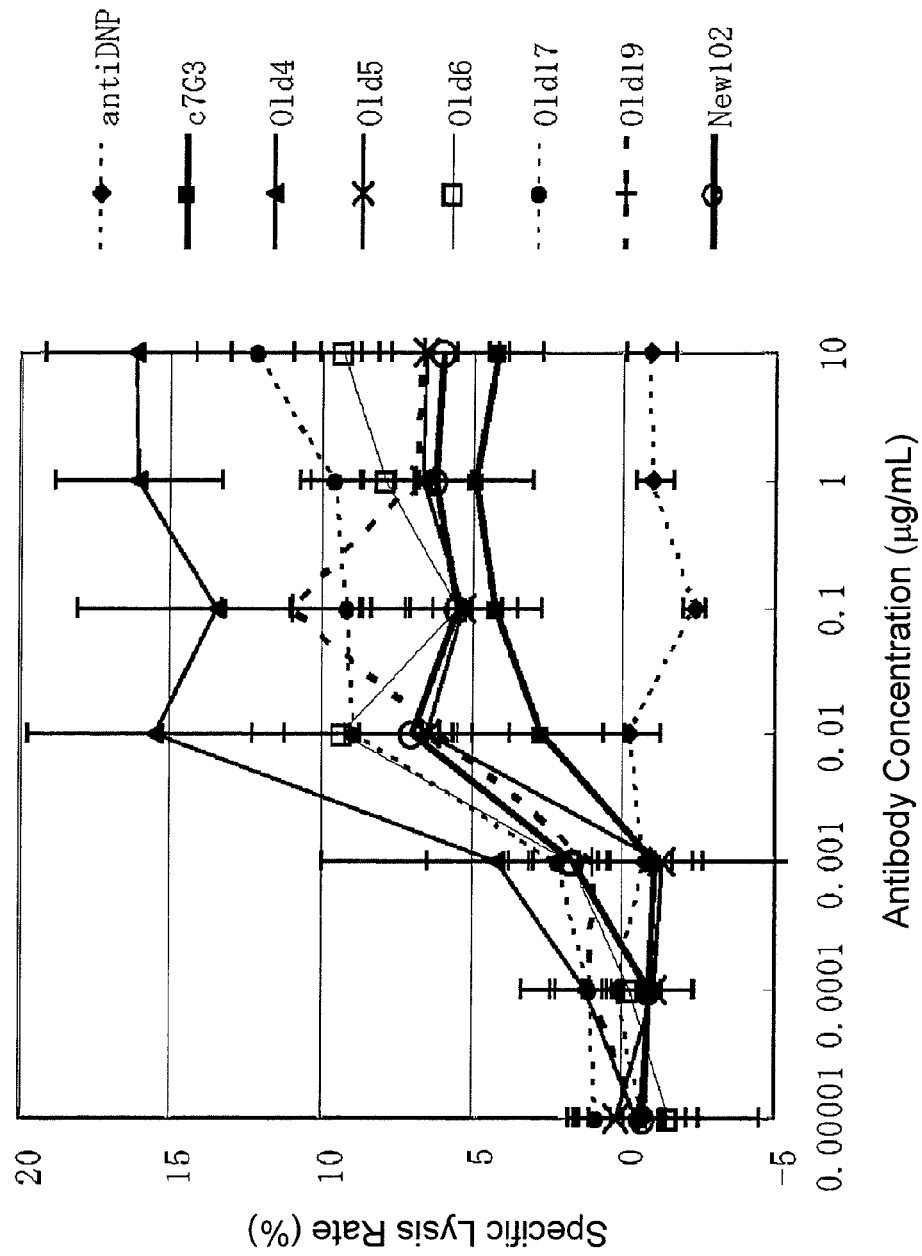
FIGS. 8 and 9 are results of ADCC test for IL-3Rα expressing cell lines using anti-IL-3Rα antibody. PBMC not cultured with IL-2 was used in FIG. 8, and PBMC cultured with IL-2 was used in FIG. 9.
Figure 9:
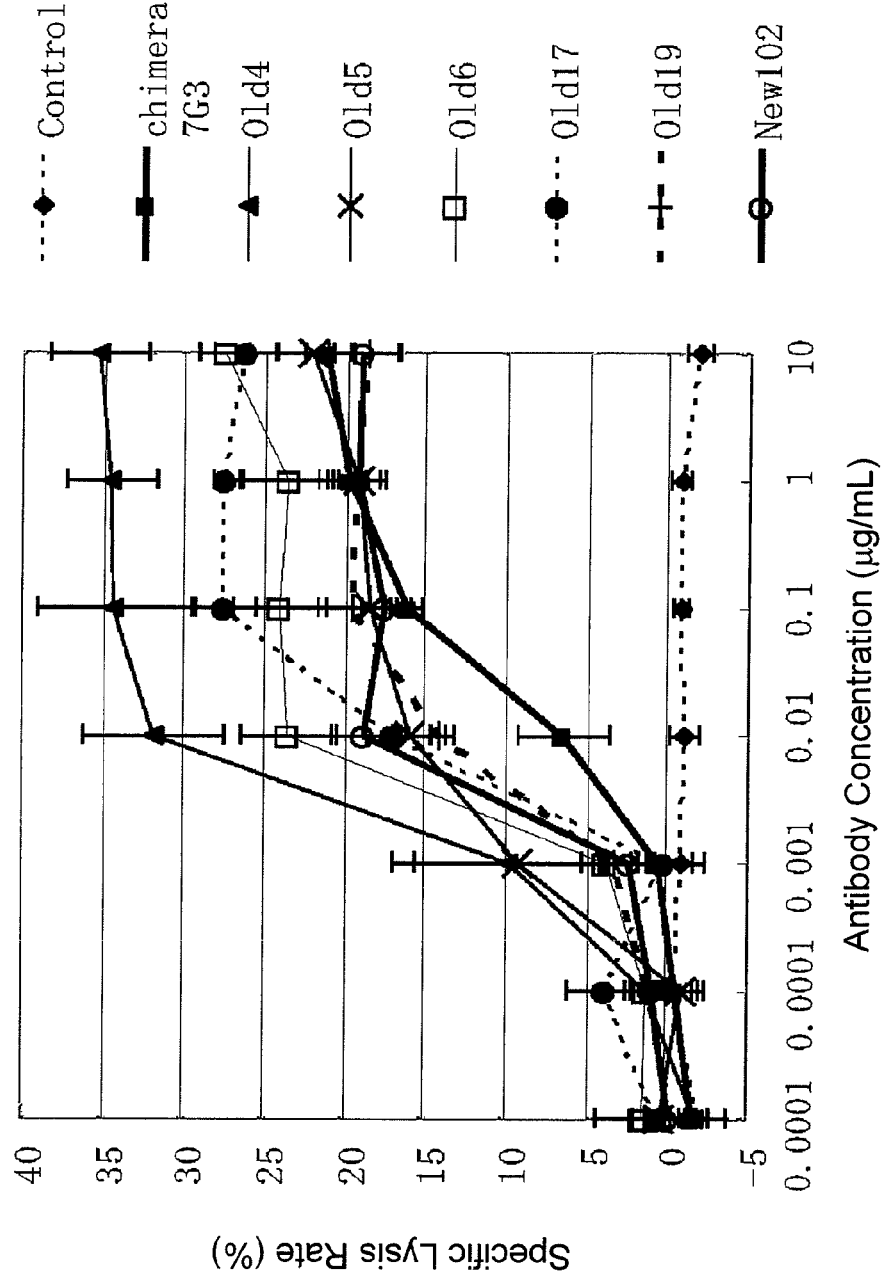

The results are shown in FIG. 8 and FIG. 9. In each IL-3Rα antibodies, the ADCC activity for the target cell was found depending on the concentration. Also, these antibodies exhibited higher ADCC activity than the chimeric 7G3 antibody as a control. This shows that the IL-3Rα antibody exhibit high ADCC activity for IL-3Rα expression cells and has a possibility of a treatment in which drug efficacy is a removal of the IL-3Rα positive cell.

Example 12

Affinity Test of Anti-IL-3Rα Antibody to Monkey IL-3Rα Protein

Regarding the presence or absence of binding of the thus obtained anti-human IL-3Rα antibody to monkey IL-3Rα, whether or not the anti-human IL-3Rα antibody prepared in Example 7 binds to the *Macaca fascicularis* IL-3Rα forced expression cell prepared in Example 1 was analyzed using flow cytometry.

Specifically, 2×10⁵ cells of the monkey IL-3Rα forced expression L929 cell were allowed to react with 100 μl so that a final concentration of 10 μg/ml, of the anti-human IL-3Rα antibody at 4° C. for 30 minutes. The antibodies used are anti-dinitrophenol (DNP) human IgG1 antibody (manufactured by this firm) as a negative control and Old4, Old5, Old17, Old19, New102 and chimeric 7G3 antibodies. Thereafter, this was washed 3 times using a staining medium (Dulbecco's PBS supplemented with 2% fetal bovine serum, 2 mM EDTA and 0.05% NaN₃). Next, a PE-labeled anti-human antibody λ chain specific antibody (Southern Bio) was allowed to undergo the reaction in the staining medium at a final concentration of 1 μg/ml and washed 3 times with the staining medium in the same manner. Finally, the cells were mixed with the staining medium and whether the presence or absence of PE positive was analyzed by flow cytometry.

Figure 10:
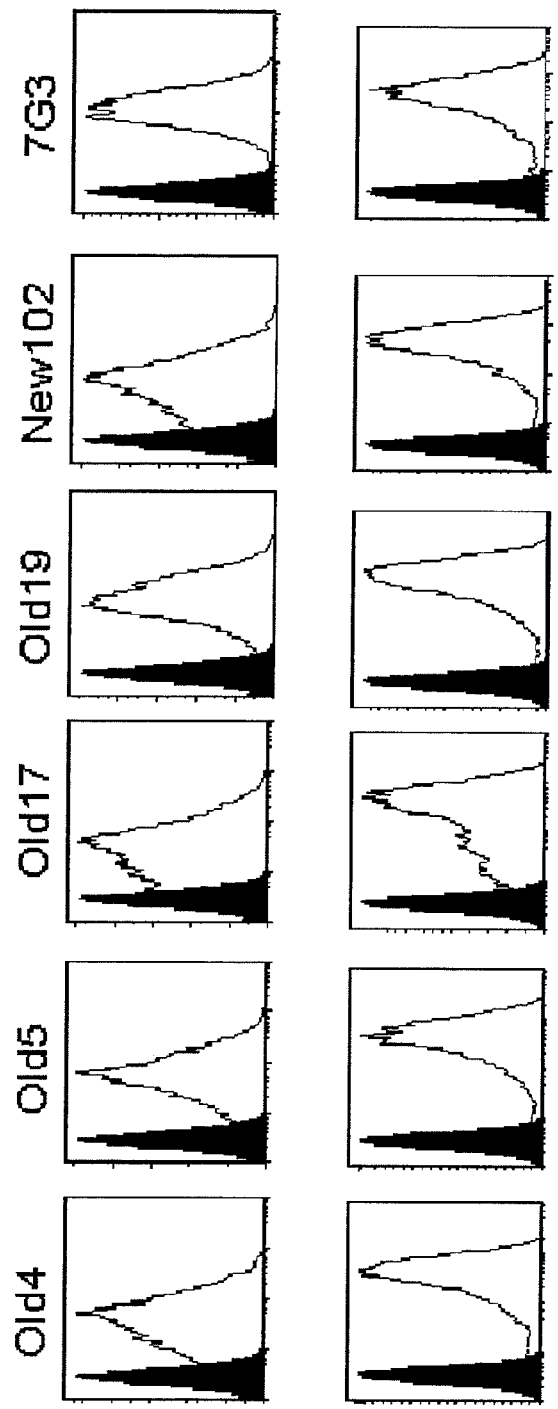
FIG. 10 is a result of flow cytometry analysis of cells expressing a *Macaca fascicularis* IL-3Rα by anti-IL-3Rα antibody and a PE-labeled anti-human IgG secondary antibody. The upper column shows the cells expressing *Macaca fascicularis* IL-3Rα, and the lower column shows the cells expressing human IL-3Rα.

The results are shown in FIG. 10. It was found that the anti-human IL-3Rα human antibodies, Old4, Old5, Old17, Old19, New102 and chimeric 7G3 antibodies, react with the *Macaca fascicularis* IL-3Rα.

Example 13

Detailed Epitope Analysis of Anti-Human IL-3Rα Human Antibodies (Preparation of IL-3α/GM-CSFRα Chimeric Protein Expression Cell)

In order to carry out further detailed epitope analysis of IL-3Rα antibodies, a chimeric protein in which a region smaller than the domain of IL-3Rα extra-membrane region was replaced by GM-CSFRα was expressed in a cell and affinity of each anti-IL-3Rα antibody to the cell was analyzed. In brief, firstly, a region considered to be positioned at outside based on a three dimensional structure prediction of IL-3Rα molecule was determined, secondly, vectors which express IL-3Rα molecules in which the small region was replaced by GM-CSFRα were respectively constructed, thirdly, these were forcedly expressed in HEK293F cell and fourthly, whether or not each anti-IL-3Rα antibody labeled with fluorescence dye binds thereto was observed by flow cytometry.

(Domain Mapping of IL-3α)

Among the 3 domains divided according to Example 7, A and B domains which were recognized by the obtained antibodies Old19 and New102 were selected and analyzed in detail. Based on the three dimensional structure of IL-4 receptor alpha chain (IL-4Rα, CD124) (PDB: 3BPNC; Chain C, Crystal Structure of the I14-I14r-Il3ra Ternary Complex), three dimensional structure of IL-3Rα was subjected to homology modeling using SWISS-MODEL (http://swissmodel.expasy.org// SWISS-MODEL.html). The predicted IL-3Rα protein structure was visualized using a graphic software RasMol (http://rasmol.org/) and 7 regions considered to be positioned at extracellular amino acid region of IL-3Rα molecule were determined (FIG. 4).

In order to specify epitope of anti-human IL-3Rα human antibody, a protein in which corresponding regions of GM-CSFRα were replaced by the 6 regions of IL-3Rα divided as described in the above was prepared and expressed on the cell membrane, and the presence or absence of binding of antibodies was determined.

Using the IL-3RA-Flag/pEGFP-N1 plasmid DNA as a template, amplification was carried out by a PCR method which uses PrimeSTAR(R) HS DNA polymerase (TAKARA BIO INC.). Regarding the PCR, a two step reaction at 98° C. 10 seconds-68° C. 5 minutes was carried out 25 cycles. The PCR primers used are as follows.

```
Region 1 Deficiency;
                                   (SEQ ID NO: 149)
   CD123-Fw21:  CGTGGAACCCGCAGTGAACAATAGCTATT (SEQ ID NO: 150)
   CD123-Re21:  ACTCTGTTCTTTTTAACACACTCGATATCG Region 3 Deficiency;
                                   (SEQ ID NO: 151)
   CD123-Fw22:  CTTTATCCAAATAACAGTGGGAAGCCTTG (SEQ ID NO: 152)
   CD123-Re22:  CAGTTTCTGTTGGAATGGTGGGTTGGCCACT Region 4 Deficiency;
                                   (SEQ ID NO: 153)
   CD123-Fw23:  AGGGAGGGTACCGGTGCGGAGAATCTGACCTGCT (SEQ ID NO: 154)
   CD123-Re23:  TCCTGAATTTGGATAGAAGAGGATCCACGTGG Region 5 Deficiency;
                                   (SEQ ID NO: 155)
   CD123-Fw24:  GGTCCGACGGCCCCCGCGGACGTCCAGTA (SEQ ID NO: 156)
   CD123-Re24:  CCTCGCCCAGGTACAGCTCAAGAAATCCACGT Region 6 Deficiency;
                                   (SEQ ID NO: 157)
   CD123-Fw25:  ACGGAACCAGCGCAGCCTTCGGTATCCCCT (SEQ ID NO: 158)
   CD123-Re25:  TAACCAGAAAGTGGGAACTTTGAGAACC Region 7 Deficiency;
                                   (SEQ ID NO: 159)
   CD123-Fw26:  TCTTTGATTCATTTGTCGTCTTTTCACA (SEQ ID NO: 160)
   CD123-Re26:  ATTGGATGCCGAAGGCTGCGCTCCTGCCC
```

The thus obtained PCR product was subjected to 0.8% agarose gel electrophoresis (135 V, 15 minutes, TAE buffer). DNA was visualized by ethidium bromide staining After confirming the amplification, purification was carried out using Wizard SV Gel and PCR Clean-Up System. The thus obtained DNA was subjected to phosphorylation using polynucleotide kinase (New England Biolabs) and to ethanol precipitation and then a part thereof was allowed to undergo the reaction using TaKaRa Ligation Kit. Regarding the transformation, a ligation sample and DH10B competent cell were mixed and spread on an LB plate (containing kanamycin). A plasmid DNA was extracted from the thus obtained colony by the Miniprep method and digested with XhoI and NotI and the insert was verified.

(Flow cytometry analysis of IL-3Rα/GM-CSFRα chimeric protein expression cell using labeled anti-IL-3Rα antibody)

HEK293T cell was used in the preparation of IL-3Rα/GM-CSFRα chimeric protein expression cell. The plasmid DNA obtained in the above was introduced as an expression vector into the HEK293T. HEK293T introduced with the expression vector was cultured under an environment of 5% CO₂ and 37° C. and used in the flow cytometry analysis 2 days after the introduction.

Each of Alexa Flour488-labeled human antibodies or commercially available FITC-labeled anti-IL-3Rα mouse antibodies (7G3 and 9F5: both available from BD Biosciences, 6H6: from Acris Antibodies) at a concentration of 1 μg/ml was allowed to react for 30 minutes on ice with 100,000 to 1,000,000 cells of the chimeric protein expression cell. A staining medium (Dulbecco's PBS containing 2% fetal calf serum, 2 mM EDTA and 0.05% NaN₃) was used for diluting the antibodies and cells. Next, the cells reacted with each antibody were washed 3 times with the staining medium, and whether or not the labeled antibody bound to the cells was confirmed by flow cytometry.

Figure 3:
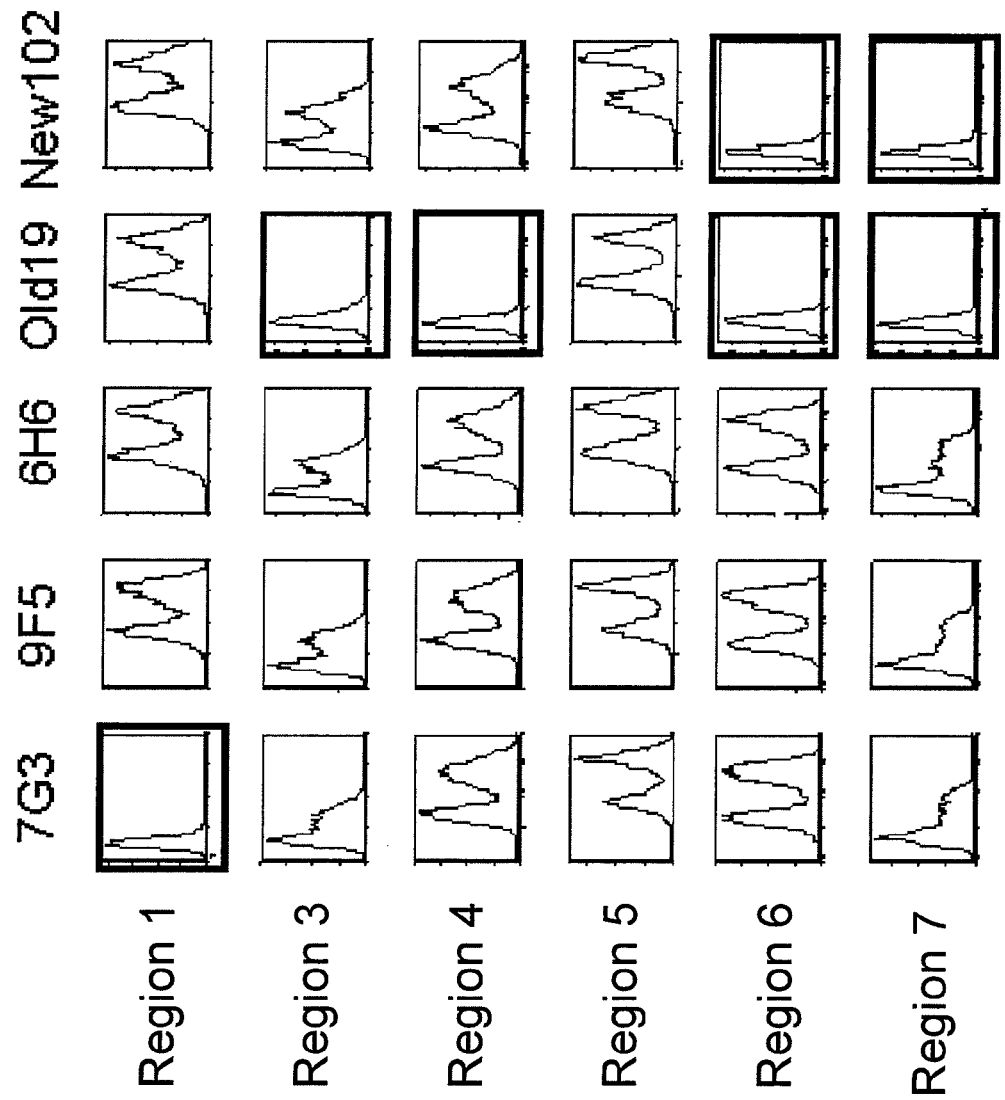
FIG. 3 is a result of a flow cytometry analysis of a cell expressing an IL-3Rα/GM-CSFRα chimeric protein using a labeled anti-IL-3Rα antibody.

The results are shown in FIG. 3. The reaction of the antibody c7G3 disappeared only in the case of the protein expression cell in which the region 1 was replaced by GM-CSFRα. Reaction of the Old19 disappeared in the case of the protein expression cell in which the region 3 and region 4 in A domain and region 6 and region 7 in B domain were replaced by GM-CSFRα. Reaction of the New102 disappeared in the case of the protein expression cell in which the region 6 and region 7 of B domain was replaced by GM-CSFRα.

Based on the above, it was shown a possibility that the antibody Old19 recognized the regions 3 and 4 of A domain and regions 6 and 7 of B domain, and the antibody New102 recognized the regions 6 and 7 of B domain. The above results are summarized as Table 4.

TABLE 4

| Region (domain) | Replacing sequence | 7G3 | 9F5 | 6H6 | Old19 | New102 |
| --- | --- | --- | --- | --- | --- | --- |
| Region 1 (A) | 55-DADYSMP-61 | − | ++ | ++ | ++ | ++ |
| Region 3 (A) | 91-STWILFPE-98 | ++ | ++ | ++ | − | ++ |
| Region 4 (A-B) | 97-PENSGKPWA-104 | ++ | ++ | ++ | − | ++ |
| Region 5 (B) | 122-CSWAVGPG-128 | ++ | ++ | ++ | ++ | ++ |
| Region 6 (B) | 182-ILVRGRS-188 | ++ | ++ | ++ | − | − |
| Region 7 (B) | 192-GIPCTDK-198 | ++ | ++ | ++ | − | − |

Industrial Applicability

According to the invention, there is provided an antibody to human IL-3Rα protein (another name: human CD123) and a therapeutic agent and a diagnostic agent for myelocytic malignant tumors, particularly acute myeloid leukemia (AML), which comprises a human IL-3Rα antibody as an active ingredient.

Free Text of Sequence Listing
SEQ ID NO: 3: IL-3Rα_Fw primer
SEQ ID NO: 4: IL-3Rα_Re primer
SEQ ID NO: 5: IL-3Rα_seqF1 primer
SEQ ID NO: 6: Insert (MfeI from NotI)
SEQ ID NO: 7: Rhe123Fw1 primer
SEQ ID NO: 8: Rhe123Rv1 primer
SEQ ID NO: 9: T7 primer
SEQ ID NO: 10: SP6 primer
SEQ ID NO: 11: Insert (MfeI to NotI) of *Macaca fascicularis* IL-3Rα
SEQ ID NO: 12: Insert (MfeI to NotI) of *Macaca mulatta* IL-3Rα
SEQ ID NO: 13: hIL-3Rαsol-FLAG-NotI primer
SEQ ID NO: 14: Insert (MfeI to NotI)
SEQ ID NO: 15: hh-6 primer
SEQ ID NO: 16: hh-3 primer
SEQ ID NO: 17: hh-4 primer
SEQ ID NO: 18: Old4 heavy chain specific primer Fw
SEQ ID NO: 19: Old4 heavy chain specific primer Rv
SEQ ID NO: 20: Old5 heavy chain specific primer Fw
SEQ ID NO: 21: Old5 heavy chain specific primer Rv
SEQ ID NO: 22: Old17 heavy chain specific primer Fw
SEQ ID NO: 23: Old17 heavy chain specific primer Rv
SEQ ID NO: 24: Old19 heavy chain specific primer Fw
SEQ ID NO: 25: Old19 heavy chain specific primer Rv
SEQ ID NO: 26: New102 heavy chain specific primer Fw
SEQ ID NO: 27: New102 heavy chain specific primer Rv
SEQ ID NO: 28: Old6 heavy chain specific primer Fw
SEQ ID NO: 29: Old6 heavy chain specific primer Rv
SEQ ID NO: 30: mH_Rv1 primer
SEQ ID NO: 31: mH_Rv2 primer
SEQ ID NO: 32: 7G3 heavy chain specific primer Fw
SEQ ID NO: 33: 7G3 heavy chain specific primer Rv
SEQ ID NO: 34: hk-2 primer
SEQ ID NO: 35: hk-6 primer
SEQ ID NO: 36: Old4 light chain specific primer Fw
SEQ ID NO: 37: Old4 light chain specific primer Rv
SEQ ID NO: 38: Old5 light chain specific primer Fw
SEQ ID NO: 39: Old5 light chain specific primer Rv
SEQ ID NO: 40: Old17 light chain specific primer Fw
SEQ ID NO: 41: Old17 light chain specific primer Rv
SEQ ID NO: 42: Old19 light chain specific primer Fw
SEQ ID NO: 43: Old19 light chain specific primer Rv
SEQ ID NO: 44: New102 light chain specific primer Fw
SEQ ID NO: 45: New102 light chain specific primer Rv
SEQ ID NO: 46: Old6 light chain specific primer Fw
SEQ ID NO: 47: Old6 light chain specific primer Rv
SEQ ID NO: 48: mK_Rv1 primer
SEQ ID NO: 49: mK_Rv2 primer
SEQ ID NO: 50: 7G3 light chain specific primer Fw
SEQ ID NO: 51: 7G3 light chain specific primer Rv
SEQ ID NO: 80: hCD116Fw-MfeI primer
SEQ ID NO: 81: hCD116Rv-NotI primer
SEQ ID NO: 82: hCD116Fw-MfeI primer
SEQ ID NO: 83: hCD116Rv-NotI primer
SEQ ID NO: 84: hCD116Fw-MfeI primer
SEQ ID NO: 85: hCD116Rv-NotI primer
SEQ ID NO: 86: hCD116SeqFw1 primer
SEQ ID NO: 87: hCD116SeqFw2 primer
SEQ ID NO: 88: hCD116SeqRv1 primer
SEQ ID NO: 89: T7 primer
SEQ ID NO: 90: hCD123-C-FLAG-R1 primer
SEQ ID NO: 91: IL-3Rα_Fw primer
SEQ ID NO: 92: C-FLAG-NotR2 primer
SEQ ID NO: 93: pEGFP-N-1-Fw primer
SEQ ID NO: 94: pEGFP-N-1-Re primer
SEQ ID NO: 95: pEGFP-N-1-Fw primer
SEQ ID NO: 96: pEGFP-N1-Re primer
SEQ ID NO: 97: CD123R11pEGFPN1 primer
SEQ ID NO: 98: CD123F11 primer
SEQ ID NO: 99: CD123R12-2 primer
SEQ ID NO: 100: CD123F12-2 primer
SEQ ID NO: 101: CD123R13 primer
SEQ ID NO: 102: CD123F13 primer
SEQ ID NO: 103: pEGFP-N-1-Fw primer
SEQ ID NO: 104: pEGFP-N1-Re primer
SEQ ID NO: 105: GM-CSFRF11 primer
SEQ ID NO: 106: GM-CSFRR11 primer
SEQ ID NO: 107: GM-CSFRF12 primer
SEQ ID NO: 108: GM-CSFRR12 primer
SEQ ID NO: 109: GM-CSFRF13 primer
SEQ ID NO: 110: GM-CSFRR13 primer
SEQ ID NO: 111: pEGFP-N-1-Fw primer
SEQ ID NO: 112: pEGFP-N-1-Re primer
SEQ ID NO: 149: CD123-Fw21 primer SEQ ID NO: 150: CD123-Re21 primer
SEQ ID NO: 151: CD123-Fw22 primer
SEQ ID NO: 152: CD123-Re22 primer
SEQ ID NO: 153: CD123-Fw23 primer
SEQ ID NO: 154: CD123-Re23 primer
SEQ ID NO: 155: CD123-Fw24 primer SEQ ID NO: 156: CD123-Re24 primer
SEQ ID NO: 157: CD123-Fw25 primer
SEQ ID NO: 158: CD123-Re25 primer
SEQ ID NO: 159: CD123-Fw26 primer
SEQ ID NO: 160: CD123-Re26 primer

---

The invention claimed is:

1. An isolated antibody to a human IL-3Rα chain, which does not inhibit IL-3 signaling and binds to B domain of the human IL-3Rα chain but does not bind to C domain of the human IL-3Rα chain, wherein the antibody comprises heavy chain complementarity determining regions ("CDR") 1 to 3 of SEQ ID NOs: 125 to 127 and light chain CDR 1 to 3 of SEQ IDS NOs: 143 to 145.

2. The antibody according to claim 1, which shows a specific lysis rate of 10% at an antibody concentration of 0.01 μg/ml, by a Colon-26/hCD123 antibody-dependent cellular cytotoxicity assay method using peripheral blood mononuclear cells cultured with IL-2.

3. The antibody according to claim 1, which comprises a heavy chain variable region comprising an amino acid sequence from glutamine (Q) at position 20 to serine (S) at position 138 in the amino acid sequence of SEQ ID NO:69 and a light chain variable region comprising an amino acid sequence from aspartic acid (D) at position 23 to lysine (K) at position 129 in the amino acid sequence of SEQ ID NO:71.

4. A pharmaceutical composition comprising the IL-3Rα antibody according to claim 1 as an active ingredient and a pharmaceutically acceptable carrier.

5. A composition comprising the IL-3Rα antibody according to claim 1.

6. A method for producing an antibody to a human IL-3Rα chain, comprising culturing a host cell containing a polynucleotide encoding the antibody in cell culture under conditions allowing the expression of the antibody and recovering the antibody from the cell culture,
wherein said antibody does not inhibit IL-3 signaling and binds to B domain of the human IL-3Rα chain but does not bind to C domain of the human IL-3Rα chain, and wherein the antibody comprises a heavy chain variable region having at least 95% sequence identity to the amino acid sequence of residues 20-138 of SEQ ID NO: 69, and a light chain variable region having at least 95% sequence identity to the amino acid sequence of residues 23-129 of SEQ ID NO: 71.

7. A method for producing an antibody to a human IL-3Rα chain, comprising culturing a host cell containing a polynucleotide encoding the antibody in cell culture under conditions allowing the expression of the antibody and recovering the antibody from the cell culture,
wherein said antibody does not inhibit IL-3 signaling and binds to B domain of the human IL-3Rα chain but does not bind to C domain of the human IL-3Rα chain, and wherein said polynucleotide encodes a heavy chain variable region comprising amino acid residues 20-138 of SEQ ID NO: 69 and a light chain variable region comprising amino acid residues 23-129 of SEQ ID NO: 71.

* * * * *

SEQUENCE LISTING

<160> NUMBER OF SEQ ID NOS: 160

<210> SEQ ID NO 1
<211> LENGTH: 378
<212> TYPE: PRT
<213> ORGANISM: Homo sapiens

<400> SEQUENCE: 1

```
Met Val Leu Leu Trp Leu Thr Leu Leu Leu Ile Ala Leu Pro Cys Leu
1               5                   10                  15

Leu Gln Thr Lys Glu Asp Pro Asn Pro Ile Thr Asn Leu Arg Met
            20                  25                  30

Lys Ala Lys Ala Gln Gln Leu Thr Trp Asp Leu Asn Arg Asn Val Thr
        35                  40                  45

Asp Ile Glu Cys Val Lys Asp Ala Asp Tyr Ser Met Pro Ala Val Asn
    50                  55                  60

Asn Ser Tyr Cys Gln Phe Gly Ala Ile Ser Leu Cys Glu Val Thr Asn
65                  70                  75                  80

Tyr Thr Val Arg Val Ala Asn Pro Pro Phe Ser Thr Trp Ile Leu Phe
                85                  90                  95

Pro Glu Asn Ser Gly Lys Pro Trp Ala Gly Ala Glu Asn Leu Thr Cys
            100                 105                 110

Trp Ile His Asp Val Asp Phe Leu Ser Cys Ser Trp Ala Val Gly Pro
        115                 120                 125

Gly Ala Pro Ala Asp Val Gln Tyr Asp Leu Tyr Leu Asn Val Ala Asn
    130                 135                 140

Arg Arg Gln Gln Tyr Glu Cys Leu His Tyr Lys Thr Asp Ala Gln Gly
145                 150                 155                 160

Thr Arg Ile Gly Cys Arg Phe Asp Asp Ile Ser Arg Leu Ser Ser Gly
                165                 170                 175

Ser Gln Ser Ser His Ile Leu Val Arg Gly Arg Ser Ala Ala Phe Gly
            180                 185                 190

Ile Pro Cys Thr Asp Lys Phe Val Val Phe Ser Gln Ile Glu Ile Leu
        195                 200                 205

Thr Pro Pro Asn Met Thr Ala Lys Cys Asn Lys Thr His Ser Phe Met
    210                 215                 220

His Trp Lys Met Arg Ser His Phe Asn Arg Lys Phe Arg Tyr Glu Leu
225                 230                 235                 240

Gln Ile Gln Lys Arg Met Gln Pro Val Ile Thr Glu Gln Val Arg Asp
                245                 250                 255

Arg Thr Ser Phe Gln Leu Leu Asn Pro Gly Thr Tyr Thr Val Gln Ile
            260                 265                 270

Arg Ala Arg Glu Arg Val Tyr Glu Phe Leu Ser Ala Trp Ser Thr Pro
        275                 280                 285

Gln Arg Phe Glu Cys Asp Gln Glu Gly Ala Asn Thr Arg Ala Trp
    290                 295                 300

Arg Thr Ser Leu Leu Ile Ala Leu Gly Thr Leu Leu Ala Leu Val Cys
305                 310                 315                 320
```

```
Val Phe Val Ile Cys Arg Arg Tyr Leu Val Met Gln Arg Leu Phe Pro
                325                 330                 335

Arg Ile Pro His Met Lys Asp Pro Ile Gly Asp Ser Phe Gln Asn Asp
            340                 345                 350

Lys Leu Val Val Trp Glu Ala Gly Lys Ala Gly Leu Glu Glu Cys Leu
            355                 360                 365

Val Thr Glu Val Gln Val Val Gln Lys Thr
            370                 375

<210> SEQ ID NO 2
<211> LENGTH: 308
<212> TYPE: PRT
<213> ORGANISM: Homo sapiens

<400> SEQUENCE: 2

Met Val Leu Leu Trp Leu Thr Leu Leu Ile Ala Leu Pro Cys Leu
1               5                   10                  15

Leu Gln Thr Lys Glu Asp Pro Asn Pro Ile Thr Asn Leu Arg Met
            20                  25                  30

Lys Ala Lys Ala Gln Gln Leu Thr Trp Asp Leu Asn Arg Asn Val Thr
            35                  40                  45

Asp Ile Glu Cys Val Lys Asp Ala Asp Tyr Ser Met Pro Ala Val Asn
50                  55                  60

Asn Ser Tyr Cys Gln Phe Gly Ala Ile Ser Leu Cys Glu Val Thr Asn
65                  70                  75                  80

Tyr Thr Val Arg Val Ala Asn Pro Pro Phe Ser Thr Trp Ile Leu Phe
                85                  90                  95

Pro Glu Asn Ser Gly Lys Pro Trp Ala Gly Ala Glu Asn Leu Thr Cys
                100                 105                 110

Trp Ile His Asp Val Asp Phe Leu Ser Cys Ser Trp Ala Val Gly Pro
            115                 120                 125

Gly Ala Pro Ala Asp Val Gln Tyr Asp Leu Tyr Leu Asn Val Ala Asn
            130                 135                 140

Arg Arg Gln Gln Tyr Glu Cys Leu His Tyr Lys Thr Asp Ala Gln Gly
145                 150                 155                 160

Thr Arg Ile Gly Cys Arg Phe Asp Asp Ile Ser Arg Leu Ser Ser Gly
                165                 170                 175

Ser Gln Ser Ser His Ile Leu Val Arg Gly Arg Ser Ala Ala Phe Gly
            180                 185                 190

Ile Pro Cys Thr Asp Lys Phe Val Val Phe Ser Gln Ile Glu Ile Leu
            195                 200                 205

Thr Pro Pro Asn Met Thr Ala Lys Cys Asn Lys Thr His Ser Phe Met
210                 215                 220

His Trp Lys Met Arg Ser His Phe Asn Arg Lys Phe Arg Tyr Glu Leu
225                 230                 235                 240

Gln Ile Gln Lys Arg Met Gln Pro Val Ile Thr Glu Gln Val Arg Asp
                245                 250                 255

Arg Thr Ser Phe Gln Leu Leu Asn Pro Gly Thr Tyr Thr Val Gln Ile
            260                 265                 270

Arg Ala Arg Glu Arg Val Tyr Glu Phe Leu Ser Ala Trp Ser Thr Pro
            275                 280                 285

Gln Arg Phe Glu Cys Asp Gln Glu Glu Gly Ala Asn Thr Arg Ala Trp
            290                 295                 300

Arg Thr Ser Leu
305
```

```
<210> SEQ ID NO 3
<211> LENGTH: 34
<212> TYPE: DNA
<213> ORGANISM: Artificial
<220> FEATURE:
<223> OTHER INFORMATION: primer IL-3RA_Fw

<400> SEQUENCE: 3
cggcaattgc caccatggtc ctcctttggc tcac                                34

<210> SEQ ID NO 4
<211> LENGTH: 31
<212> TYPE: DNA
<213> ORGANISM: Artificial
<220> FEATURE:
<223> OTHER INFORMATION: IL-3RA_Re

<400> SEQUENCE: 4
attgcggccg ctcaagtttt ctgcacgacc t                                   31

<210> SEQ ID NO 5
<211> LENGTH: 20
<212> TYPE: DNA
<213> ORGANISM: Artificial
<220> FEATURE:
<223> OTHER INFORMATION: primer IL-3RA_seqF1

<400> SEQUENCE: 5
gtcttcacta caaaacggat                                                20

<210> SEQ ID NO 6
<211> LENGTH: 1156
<212> TYPE: DNA
<213> ORGANISM: Artificial
<220> FEATURE:
<223> OTHER INFORMATION: insert sequence

<400> SEQUENCE: 6
caattgccac catggtcctc ctttggctca cgctgctcct gatcgccctg ccctgtctcc    60
tgcaaacgaa ggaagatcca aacccaccaa tcacgaacct aaggatgaaa gcaaaggctc   120
agcagttgac ctgggacctt aacagaaatg tgaccgatat cgagtgtgtt aaagacgccg   180
actattctat gccggcagtg aacaatagct attgccagtt tggagcaatt tccttatgtg   240
aagtgaccaa ctacaccgtc cgagtggcca cccaccattt ctccacgtgg atcctcttcc   300
ctgagaacag tgggaagcct tgggcaggtg cggagaatct gacctgctgg attcatgacg   360
tggatttctt gagctgcagc tgggcggtag gcccgggggc ccccgcggac gtccagtacg   420
acctgtactt gaacgttgcc aacaggcgtc aacagtacga gtgtcttcac tacaaaacgg   480
atgctcaggg aacacgtatc gggtgtcgtt tcgatgacat ctctcgactc tccagcggtt   540
ctcaaagttc ccacatcctg gtgcggggca ggagcgcagc cttcggtatc ccctgcacag   600
ataagtttgt cgtctttttca cagattgaga tattaactcc acccaacatg actgcaaagt   660
gtaataagac acattccttt atgcactgga aaatgagaag tcatttcaat cgcaaatttc   720
gctatgagct tcagatacaa agagaatgc agcctgtaat cacagaacag gtcagagaca   780
gaacctcctt ccagctactc aatcctggaa cgtacacagt acaaataaga gcccgggaaa   840
gagtgtatga attcttgagc gcctggagca ccccccagcg cttcgagtgc gaccaggagg   900
agggcgcaaa cacacgtgcc tggcggacgt cgctgctgat cgcgctgggg acgtgctggg   960
ccctggtctg tgtcttcgtg atctgcagaa ggtatctggt gatgcagaga ctcttcccc   1020
```

```
gcatccctca catgaaagac cccatcggtg acagcttcca aaacgacaag ctggtggtct    1080
gggaggcggg caaagccggc ctggaggagt gtctggtgac tgaagtacag gtcgtgcaga    1140
aaacttgagc ggccgc                                                   1156

<210> SEQ ID NO 7
<211> LENGTH: 38
<212> TYPE: DNA
<213> ORGANISM: Artificial
<220> FEATURE:
<223> OTHER INFORMATION: primer Rhe123Fw1

<400> SEQUENCE: 7
cggcaattgc caccatgacc ctcctttggc tgacgctg                                38

<210> SEQ ID NO 8
<211> LENGTH: 38
<212> TYPE: DNA
<213> ORGANISM: Artificial
<220> FEATURE:
<223> OTHER INFORMATION: primer Rhe123Rv1

<400> SEQUENCE: 8
tatattgcgg ccgctcaagt tttctccacc acctgcac                                38

<210> SEQ ID NO 9
<211> LENGTH: 20
<212> TYPE: DNA
<213> ORGANISM: Artificial
<220> FEATURE:
<223> OTHER INFORMATION: primer T7

<400> SEQUENCE: 9
taatacgact cactataggg                                                    20

<210> SEQ ID NO 10
<211> LENGTH: 19
<212> TYPE: DNA
<213> ORGANISM: Artificial
<220> FEATURE:
<223> OTHER INFORMATION: primer SP6

<400> SEQUENCE: 10
gatttaggtg acactatag                                                     19

<210> SEQ ID NO 11
<211> LENGTH: 1156
<212> TYPE: DNA
<213> ORGANISM: Artificial
<220> FEATURE:
<223> OTHER INFORMATION: insert sequence

<400> SEQUENCE: 11
caattgccac catgaccctc ctttggctga cgctgctcct ggtcgccacg ccctgtctcc      60
tgcaaacgaa ggaggatcca aatgcaccaa tcaggaatct aaggatgaaa gaaaaggctc     120
agcagttgat gtgggacctg aacagaaacg tgaccgacgt ggagtgtatc aaaggcaccg     180
actattctat gccggcaatg aacaacagct attgccagtt cggagccatt tccttatgtg     240
aagtgaccaa ctacaccgtc cgagtggcca gtccccgtt ctccacgtgg atcctcttcc      300
ctgagaacag tgggacgcct caggcaggcg cggagaatct gacctgctgg gttcatgacg     360
tggatttctt gagctgcagc tgggtggcag gccggcggc cccgctgac gtccagtacg       420 acctgtactt gaacaatccc aacagccacg aacagtacag gtgccttcac tacaaaacgg     480
```

```
atgctcgggg aacacagatc gggtgtcggt tcgatgacat cgctcgactc tcccgcggtt      540
ctcaaagttc ccacatcctg gtgaggggca ggagcgcagc cgtcagtatc ccctgcacag      600
ataagtttgt cttcttttca cagattgaga gattaactcc acccaacatg actggagagt      660
gtaatgagac acattccttc atgcactgga aaatgaaaag tcatttcaat cgcaaattcc      720
gctatgagct tcggatccaa aagagaatgc agcctgtaag gacagaacag gtcagagaca      780
caacctcctt ccagctaccc aatcctggaa cgtacacagt gcaaataaga gcccgggaaa      840
cagtgtatga attcttgagt gcctggagca ccccccagcg cttcgagtgc gaccaggagg      900
agggcgcgag ctcgcgtgcc tggcggacgt cgctgctgat cgcgctgggg acgctgctgg      960
ccttgctctg tgtgttcctc atctgcagaa ggtatctggt gatgcagagg ctgtttcccc     1020
gcatcccaca catgaaagac cccatcggtg acaccttcca acaggacaag ctggtggtct     1080
gggaggcggg caaagccggc ctggaggagt gtctggtgtc tgaagtgcag gtggtggaga     1140
aaacttgagc ggccgc                                                     1156

<210> SEQ ID NO 12
<211> LENGTH: 1156
<212> TYPE: DNA
<213> ORGANISM: Artificial
<220> FEATURE:
<223> OTHER INFORMATION: insert sequence

<400> SEQUENCE: 12
caattgccac catgaccctc ctttggctga cgctgctcct ggtcgccacg ccctgtctcc       60
tgcaaaccaa ggaggatcca aatgcaccaa tcaggaatct aaggatgaaa gaaaaggctc      120
agcagttgat gtgggacctg aacagaaacg tgaccgacgt ggagtgtatc aaaggcaccg      180
actattctat gccggcaatg aacgacagct attgccagtt cggagccatt tccttatgtg      240
aagtgaccaa ctacaccgtc cgagtggcca gtcctccgtt ctccacgtgg atcctcttcc      300
ctgagaacag tgggacgcct cgggcaggcg cggagaattt gacctgctgg gttcatgacg      360
tggatttctt gagctgcagc tgggtggtag gccggcggc ccccgctgac gtccagtacg      420
acctgtactt gaacaatccc aacagccacg aacagtacag gtgccttcgc tacaaaacgg      480
atgctcgggg aacacagatc gggtgtcggt tcgatgacat cgctcgactc tcccgcggtt      540
ctcaaagttc ccacatcctg gtgaggggca ggagcgcagc cgtcagtatc ccctgcacag      600
ataagtttgt cttcttttca cagattgaga gattaactcc acccaacatg actggagagt      660
gtaatgagac acattccttc atgcactgga aaatgaaaag tcatttcaat cgcaaattcc      720
actatgagct tcggatccaa aagagaatgc agcctgtaag gacagaacag gtcagagaca      780
caacctcctt ccagctaccc aatcctggaa cgtacacagt gcaaataaga gcccgggaaa      840
cagtgtatga attcttgagt gcctggagca ccccccagcg cttcgagtgc gaccaggagg      900
agggcgcgag ctcgcgtgcc tggcggacgt cgctgctgat cgcgctgggg acgctgctgg      960
ccttgctctg tgtgttcctc atctgcagaa ggtatctggt gatgcagagg ctgtttcccc     1020
gcatcccaca catgaaagac cccatcggtg acaccttcca acaggacaag ctggtggtct     1080
gggaggcggg caaagccggc ctggaggagt gtctggtgtc tgaagtgcag gtggtggaga     1140
aaacttgagc ggccgc                                                    1156

<210> SEQ ID NO 13
<211> LENGTH: 58
<212> TYPE: DNA
<213> ORGANISM: Artificial
<220> FEATURE:
```

<223> OTHER INFORMATION: primer hIL-3RAsol-FLAG-NotI

<400> SEQUENCE: 13

```
attgcggccg ctcacttatc gtcgtcatcc ttgtagtccc gccaggcacg tgtgtttg        58
```

<210> SEQ ID NO 14
<211> LENGTH: 961
<212> TYPE: DNA
<213> ORGANISM: Artificial
<220> FEATURE:
<223> OTHER INFORMATION: insert seqence

<400> SEQUENCE: 14

```
caattgccac catggtcctc ctttggctca cgctgctcct gatcgccctg ccctgtctcc        60
tgcaaacgaa ggaagatcca aacccaccaa tcacgaacct aaggatgaaa gcaaaggctc       120
agcagttgac ctgggacctt aacagaaatg tgaccgatat cgagtgtgtt aaagacgccg       180
actattctat gccggcagtg aacaatagct attgccagtt tggagcaatt tccttatgtg       240
aagtgaccaa ctacaccgtc cgagtggcca acccaccatt ctccacgtgg atcctcttcc       300
ctgagaacag tgggaagcct tgggcaggtg cggagaatct gacctgctgg attcatgacg       360
tggatttctt gagctgcagc tgggcggtag gcccgggggc ccccgcggac gtccagtacg       420
acctgtactt gaacgttgcc aacaggcgtc aacagtacga gtgtcttcac tacaaaacgg       480
atgctcaggg aacacgtatc gggtgtcgtt tcgatgacat ctctcgactc tccagcggtt       540
ctcaaagttc ccacatcctg gtgcgggca ggagcgcagc cttcggtatc ccctgcacag       600
ataagtttgt cgtcttttca cagattgaga tattaactcc acccaacatg actgcaaagt       660
gtaataagac acattccttt atgcactgga aaatgagaag tcatttcaat cgcaaatttc       720
gctatgagct tcagatacaa aagagaatgc agcctgtaat cacagaacag gtcagagaca       780
gaacctcctt ccagctactc aatcctgaaa cgtacacagt acaaataaga gcccgggaaa       840
gagtgtatga attcttgagc gcctggagca cccccccagcg cttcgagtgc gaccaggagg       900
agggcgcaaa cacacgtgcc tggcgggact acaaggatga cgacgataag tgagcggccg       960
c                                                                      961
```

<210> SEQ ID NO 15
<211> LENGTH: 27
<212> TYPE: DNA
<213> ORGANISM: Artificial
<220> FEATURE:
<223> OTHER INFORMATION: primer hh-6

<400> SEQUENCE: 15

```
ggtccgggag atcatgaggg tgtcctt                                           27
```

<210> SEQ ID NO 16
<211> LENGTH: 26
<212> TYPE: DNA
<213> ORGANISM: Artificial
<220> FEATURE:
<223> OTHER INFORMATION: primer hh-3

<400> SEQUENCE: 16

```
gtgcacgccg ctggtcaggg cgcctg                                            26
```

<210> SEQ ID NO 17
<211> LENGTH: 23
<212> TYPE: DNA
<213> ORGANISM: Artificial
<220> FEATURE:

-continued

<223> OTHER INFORMATION: primer hh-4

<400> SEQUENCE: 17
ggtgccaggg ggaagaccga tgg                                           23

<210> SEQ ID NO 18
<211> LENGTH: 49
<212> TYPE: DNA
<213> ORGANISM: Artificial
<220> FEATURE:
<223> OTHER INFORMATION: primer Fw spcific for Old4 Heavy chain

<400> SEQUENCE: 18
agagagagag gtcgaccacc atggactgga cctggaggtt cctctttgt               49

<210> SEQ ID NO 19
<211> LENGTH: 40
<212> TYPE: DNA
<213> ORGANISM: Artificial
<220> FEATURE:
<223> OTHER INFORMATION: primer Rv specific for Old4 heavy chain

<400> SEQUENCE: 19
agagagagag gctagctgaa gagacggtga ccattgtccc                         40

<210> SEQ ID NO 20
<211> LENGTH: 49
<212> TYPE: DNA
<213> ORGANISM: Artificial
<220> FEATURE:
<223> OTHER INFORMATION: primer Fw specific for Old5 heavy chain

<400> SEQUENCE: 20
agagagagag gtcgaccacc atggactgga cctggaggtt cctctttgt               49

<210> SEQ ID NO 21
<211> LENGTH: 40
<212> TYPE: DNA
<213> ORGANISM: Artificial
<220> FEATURE:
<223> OTHER INFORMATION: primer Rv specific for Old5 heavy chain

<400> SEQUENCE: 21
agagagagag gctagctgaa gagacggtga ccattgtccc                         40

<210> SEQ ID NO 22
<211> LENGTH: 49
<212> TYPE: DNA
<213> ORGANISM: Artificial
<220> FEATURE:
<223> OTHER INFORMATION: primer Fw specific for Old17 Heavy chain

<400> SEQUENCE: 22
agagagagag gtcgaccacc atggactgga cctggaggtt cctctttgt               49

<210> SEQ ID NO 23
<211> LENGTH: 41
<212> TYPE: DNA
<213> ORGANISM: Artificial
<220> FEATURE:
<223> OTHER INFORMATION: primer Rv specific for Old 17 heavy chain

<400> SEQUENCE: 23
agagagagag gctagctgag gagacggtga caagggttcc c                       41

<210> SEQ ID NO 24

-continued

```
<211> LENGTH: 49
<212> TYPE: DNA
<213> ORGANISM: Artificial
<220> FEATURE:
<223> OTHER INFORMATION: primer Fw specific for Old19 heavy chain

<400> SEQUENCE: 24
agagagagag gtcgaccacc atggactgga cctggaggtt cctctttgt            49

<210> SEQ ID NO 25
<211> LENGTH: 39
<212> TYPE: DNA
<213> ORGANISM: Artificial
<220> FEATURE:
<223> OTHER INFORMATION: primer Rv specific for Old19 heavy chain

<400> SEQUENCE: 25
agagagagag gctagctgag gagacggtga ccagggttc                       39

<210> SEQ ID NO 26
<211> LENGTH: 49
<212> TYPE: DNA
<213> ORGANISM: Artificial
<220> FEATURE:
<223> OTHER INFORMATION: primer Fw specific for New102 Heavy chain

<400> SEQUENCE: 26
agagagagag gtcgaccacc atggactgga cctggaggtt cctctttgt            49

<210> SEQ ID NO 27
<211> LENGTH: 38
<212> TYPE: DNA
<213> ORGANISM: Artificial
<220> FEATURE:
<223> OTHER INFORMATION: primer Rv specific for New102 heavy chain

<400> SEQUENCE: 27
agagagagag gctagctgag gagacggtga ccagggtt                        38

<210> SEQ ID NO 28
<211> LENGTH: 41
<212> TYPE: DNA
<213> ORGANISM: Artificial
<220> FEATURE:
<223> OTHER INFORMATION: primer Fw specific for Old6 heavy chain

<400> SEQUENCE: 28
agagagagag gtcgacccac catggaactg gggctccgct g                    41

<210> SEQ ID NO 29
<211> LENGTH: 39
<212> TYPE: DNA
<213> ORGANISM: Artificial
<220> FEATURE:
<223> OTHER INFORMATION: primer Rv specific for Old6 heavy chain

<400> SEQUENCE: 29
agagagagag gctagctgag gagacggtga ccagggttc                       39

<210> SEQ ID NO 30
<211> LENGTH: 32
<212> TYPE: DNA
<213> ORGANISM: Artificial
<220> FEATURE:
<223> OTHER INFORMATION: primer mH_Rv1

<400> SEQUENCE: 30
```

-continued

```
attttgtcga cckyggtsyt gctggcyggg tg                              32
```

<210> SEQ ID NO 31
<211> LENGTH: 30
<212> TYPE: DNA
<213> ORGANISM: Artificial
<220> FEATURE:
<223> OTHER INFORMATION: primer mH_Rv2

<400> SEQUENCE: 31

```
gcacacyrct ggacagggat ccagagttcc                                30
```

<210> SEQ ID NO 32
<211> LENGTH: 44
<212> TYPE: DNA
<213> ORGANISM: Artificial
<220> FEATURE:
<223> OTHER INFORMATION: primer Fw specific for 7G3 heavy chain

<400> SEQUENCE: 32

```
agagagagag gtcgaccacc atgggatgga gctggatctt tctc                 44
```

<210> SEQ ID NO 33
<211> LENGTH: 40
<212> TYPE: DNA
<213> ORGANISM: Artificial
<220> FEATURE:
<223> OTHER INFORMATION: primer Rv specific for 7G3 heavy chain

<400> SEQUENCE: 33

```
agagagagag gctagctgca gagacagtga ccagagtccc                      40
```

<210> SEQ ID NO 34
<211> LENGTH: 26
<212> TYPE: DNA
<213> ORGANISM: Artificial
<220> FEATURE:
<223> OTHER INFORMATION: primer hk-2

<400> SEQUENCE: 34

```
gttgaagctc tttgtgacgg gcgagc                                    26
```

<210> SEQ ID NO 35
<211> LENGTH: 26
<212> TYPE: DNA
<213> ORGANISM: Artificial
<220> FEATURE:
<223> OTHER INFORMATION: primer hk-6

<400> SEQUENCE: 35

```
tggcgggaag atgaagacag atggtg                                    26
```

<210> SEQ ID NO 36
<211> LENGTH: 45
<212> TYPE: DNA
<213> ORGANISM: Artificial
<220> FEATURE:
<223> OTHER INFORMATION: primer Fw specific for Old4 light chain

<400> SEQUENCE: 36

```
agagagagag atctctcacc atggacatga gggtccccgc tcagc                45
```

<210> SEQ ID NO 37
<211> LENGTH: 40
<212> TYPE: DNA
<213> ORGANISM: Artificial
<220> FEATURE:

<223> OTHER INFORMATION: primer Rv specific for Old4 light chain

<400> SEQUENCE: 37
agagagagag cgtacgtttg atctccagct tggtcccctg                    40

<210> SEQ ID NO 38
<211> LENGTH: 45
<212> TYPE: DNA
<213> ORGANISM: Artificial
<220> FEATURE:
<223> OTHER INFORMATION: primer Fw specific for Old5 light chain

<400> SEQUENCE: 38
agagagagag atctctcacc atggacatga gggtccccgc tcagc              45

<210> SEQ ID NO 39
<211> LENGTH: 40
<212> TYPE: DNA
<213> ORGANISM: Artificial
<220> FEATURE:
<223> OTHER INFORMATION: primer Rv specific for Old5 light chain

<400> SEQUENCE: 39
agagagagag cgtacgtttg atctccagct tggtcccctg                    40

<210> SEQ ID NO 40
<211> LENGTH: 44
<212> TYPE: DNA
<213> ORGANISM: Artificial
<220> FEATURE:
<223> OTHER INFORMATION: primer Fw specific for Old17 light chain

<400> SEQUENCE: 40
agagagagag atctctcacc atggacatga gggtcctcgc tcag               44

<210> SEQ ID NO 41
<211> LENGTH: 40
<212> TYPE: DNA
<213> ORGANISM: Artificial
<220> FEATURE:
<223> OTHER INFORMATION: primer Rv specific for light chain

<400> SEQUENCE: 41
agagagagag cgtacgtttg atctccagct tggtcccctg                    40

<210> SEQ ID NO 42
<211> LENGTH: 44
<212> TYPE: DNA
<213> ORGANISM: Artificial
<220> FEATURE:
<223> OTHER INFORMATION: primer Fw specific for Old19 light chain

<400> SEQUENCE: 42
agagagagag atctctcacc atggacatga gggtcctcgc tcag               44

<210> SEQ ID NO 43
<211> LENGTH: 42
<212> TYPE: DNA
<213> ORGANISM: Artificial
<220> FEATURE:
<223> OTHER INFORMATION: primer Rv specific for Old19 light chain

<400> SEQUENCE: 43
agagagagag cgtacgtttg atttccacct tggtcccttg gc                 42

<210> SEQ ID NO 44

```
<211> LENGTH: 44
<212> TYPE: DNA
<213> ORGANISM: Artificial
<220> FEATURE:
<223> OTHER INFORMATION: primer Fw specific for New102 light chain

<400> SEQUENCE: 44
agagagagag atctctcacc atggacatga gggtcctcgc tcag                    44

<210> SEQ ID NO 45
<211> LENGTH: 40
<212> TYPE: DNA
<213> ORGANISM: Artificial
<220> FEATURE:
<223> OTHER INFORMATION: primer Rv specific for New102 light chain

<400> SEQUENCE: 45
agagagagag cgtacgtttg atctccagct tggtcccctg                         40

<210> SEQ ID NO 46
<211> LENGTH: 44
<212> TYPE: DNA
<213> ORGANISM: Artificial
<220> FEATURE:
<223> OTHER INFORMATION: primer Fw specific for Old6 light chain

<400> SEQUENCE: 46
gagagagaga tctctcacca tggacatgag ggtccccgct cagc                    44

<210> SEQ ID NO 47
<211> LENGTH: 42
<212> TYPE: DNA
<213> ORGANISM: Artificial
<220> FEATURE:
<223> OTHER INFORMATION: primer Rv specific for Old6 light chain

<400> SEQUENCE: 47
agagagagag cgtacgtttg atatccactt tggtcccagg gc                      42

<210> SEQ ID NO 48
<211> LENGTH: 30
<212> TYPE: DNA
<213> ORGANISM: Artificial
<220> FEATURE:
<223> OTHER INFORMATION: primer mK_Rv1

<400> SEQUENCE: 48
ttgaagctct tgacaatggg tgaagttgat                                    30

<210> SEQ ID NO 49
<211> LENGTH: 30
<212> TYPE: DNA
<213> ORGANISM: Artificial
<220> FEATURE:
<223> OTHER INFORMATION: primer mK_Rv2

<400> SEQUENCE: 49
gtaggtgctg tctttgctgt cctgatcagt                                    30

<210> SEQ ID NO 50
<211> LENGTH: 44
<212> TYPE: DNA
<213> ORGANISM: Artificial
<220> FEATURE:
<223> OTHER INFORMATION: primer Fw specific for 7G3 light chain

<400> SEQUENCE: 50
```

```
agagagagag agatctcacc atggaatcac agactcaggt cctc                      44

<210> SEQ ID NO 51
<211> LENGTH: 40
<212> TYPE: DNA
<213> ORGANISM: Artificial
<220> FEATURE:
<223> OTHER INFORMATION: primer Rv specific for 7G3 light chain

<400> SEQUENCE: 51
agagagagag cgtacgtttt atttccagct tggtcccccc                           40

<210> SEQ ID NO 52
<211> LENGTH: 443
<212> TYPE: DNA
<213> ORGANISM: Homo sapiens

<400> SEQUENCE: 52
gacccgtcga ccaccatgga ctggacctgg aggttcctct tgtggtggc agcagctaca      60 ggtgtccagt cccaggtcca gctgctacag tctggggctg aggtgaagaa gcctgggtcc    120
tcggtgaagg tctcatgcaa ggcttctgga ggcaccttca gcacctatgc tatcagctgg    180
gtgcgacagg cccctggaca agggcttgag tggatgggag ggatcatccc tatctttggt    240
atagtaaact acgcacagaa gttccagggc agagtcacga ttaccgcgga cgaatccacg    300
agtacagcct acatggaact gagcagcctg agatctgagg acacggccgt gtattattgt    360
gcgagagggg ggggctcggg cccagatgtt cttgatatct ggggccaagg gacaatggtc    420
accgtctctt cagctagcac caa                                            443

<210> SEQ ID NO 53
<211> LENGTH: 143
<212> TYPE: PRT
<213> ORGANISM: Homo sapiens
<220> FEATURE:
<221> NAME/KEY: misc_feature
<222> LOCATION: (143)..(143)
<223> OTHER INFORMATION: Xaa can be any naturally occurring amino acid

<400> SEQUENCE: 53

Met Asp Trp Thr Trp Arg Phe Leu Phe Val Val Ala Ala Thr Gly
 1               5                  10                  15

Val Gln Ser Gln Val Gln Leu Leu Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Thr Tyr Ala Ile Ser Trp Val Arg Gln Ala Pro Gly Gln Gly Leu
    50                  55                  60

Glu Trp Met Gly Gly Ile Ile Pro Ile Phe Gly Ile Val Asn Tyr Ala
65                  70                  75                  80

Gln Lys Phe Gln Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
               100                 105                 110

Tyr Tyr Cys Ala Arg Gly Gly Gly Ser Gly Pro Asp Val Leu Asp Ile
           115                 120                 125

Trp Gly Gln Gly Thr Met Val Thr Val Ser Ser Ala Ser Thr Xaa
       130                 135                 140

<210> SEQ ID NO 54
<211> LENGTH: 412
```

```
<212> TYPE: DNA
<213> ORGANISM: Homo sapiens

<400> SEQUENCE: 54
cacagatctc tcaccatgga catgagggtc cccgctcagc tcctggggct cctgctgctc      60
tggctcccag gtgccagatg tgtcatctgg atgacccagt ctccatcctt actctctgca     120
tctacaggag acagagtcac catcagttgt cggatgagtc agggcattag gagttattta     180
gcctggtatc agcaaaaacc agggaaagcc cctgagctcc tgatctatgc tgcatccact     240
ttgcaaagtg gggtcccatc aaggttcagt ggcagtggat ctgggacaga tttcactctc     300
accatcagca gcctgcagtc tgaagatttt gcaacttatt actgtcaaca gtattatagt     360
ttcccgtaca cttttggcca ggggaccaag ctggagatca aacgtacggt gg             412

<210> SEQ ID NO 55
<211> LENGTH: 133
<212> TYPE: PRT
<213> ORGANISM: Homo sapiens
<220> FEATURE:
<221> NAME/KEY: misc_feature
<222> LOCATION: (133)..(133)
<223> OTHER INFORMATION: Xaa can be any naturally occurring amino acid

<400> SEQUENCE: 55

Met Asp Met Arg Val Pro Ala Gln Leu Leu Gly Leu Leu Leu Leu Trp
1               5                   10                  15

Leu Pro Gly Ala Arg Cys Val Ile Trp Met Thr Gln Ser Pro Ser Leu
            20                  25                  30

Leu Ser Ala Ser Thr Gly Asp Arg Val Thr Ile Ser Cys Arg Met Ser
        35                  40                  45

Gln Gly Ile Arg Ser Tyr Leu Ala Trp Tyr Gln Gln Lys Pro Gly Lys
    50                  55                  60

Ala Pro Glu Leu Leu Ile Tyr Ala Ala Ser Thr Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Ser Glu Asp Phe Ala Thr Tyr Tyr Cys Gln Gln
            100                 105                 110

Tyr Tyr Ser Phe Pro Tyr Thr Phe Gly Gln Gly Thr Lys Leu Glu Ile
        115                 120                 125

Lys Arg Thr Val Xaa
    130

<210> SEQ ID NO 56
<211> LENGTH: 433
<212> TYPE: DNA
<213> ORGANISM: Homo sapiens

<400> SEQUENCE: 56
gtcgaccacc atggactgga cctggaggtt cctctttgtg gtggcagcag ctacaggtgt      60
ccagtcccag gtccagctgg tgcagtctgg ggctgaggtg aagaagcctg gtcctcggt     120 gaaggtctca tgcaaggctt ctggaggcac cttcagcacc tatgctatca gctgggtgcg     180
acaggcccct ggacaagggc ttgagtggat ggggggctc atccctatct ttgatataga     240
aaactacgca cagaagttcc agggcagagt cacgattacc gcggacgaat ccacgagcac     300
agtctatatg gaactgagca gcctgagatc tgaggacacg gccatgtatt actgtgcgag     360 agggggggggt tcgggccctg atgttcttga tatctggggc caagggacaa tggtcaccgt     420
```

<210> SEQ ID NO 57
<211> LENGTH: 141
<212> TYPE: PRT
<213> ORGANISM: Homo sapiens

<400> SEQUENCE: 57

Met Asp Trp Thr Trp Arg Phe Leu Phe Val Val Ala Ala Ala Thr Gly
1               5                   10                  15

Val Gln Ser Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Thr Tyr Ala Ile Ser Trp Val Arg Gln Ala Pro Gly Gln Gly Leu
    50                  55                  60

Glu Trp Met Gly Gly Leu Ile Pro Ile Phe Asp Ile Glu Asn Tyr Ala
65                  70                  75                  80

Gln Lys Phe Gln Gly Arg Val Thr Ile Thr Ala Asp Glu Ser Thr Ser
                85                  90                  95

Thr Val Tyr Met Glu Leu Ser Ser Leu Arg Ser Glu Asp Thr Ala Met
            100                 105                 110

Tyr Tyr Cys Ala Arg Gly Gly Gly Ser Gly Pro Asp Val Leu Asp Ile
        115                 120                 125

Trp Gly Gln Gly Thr Met Val Thr Val Ser Ser Ala Ser
    130                 135                 140

<210> SEQ ID NO 58
<211> LENGTH: 412
<212> TYPE: DNA
<213> ORGANISM: Homo sapiens

<400> SEQUENCE: 58
cacagatctc tcaccatgga catgagggtc cccgctcagc tcctggggct cctgctgctc      60
tggctcccag gtgccagatg tgtcatctgg atgacccagt ctccatcctt actctctgca    120
tctacaggag acagagtcac catcagttgt cggatgagtc agggcattag agtttattta    180
gcctggtatc agcaaaaacc agggaaagcc cctgagctcc tgatctatgc tgcatcccact   240 ttgcaaagtg gggtcccatc aaggttcagt ggcagtggat ctgggacaga tttcactctc    300
accatcagca gcctgcagtc tgaagatttt gcaacttatt actgtcaaca gtattatagt    360
ttcccgtaca cttttggcca ggggaccaag ctggagatca aacgtacggt gg            412

<210> SEQ ID NO 59
<211> LENGTH: 133
<212> TYPE: PRT
<213> ORGANISM: Homo sapiens
<220> FEATURE:
<221> NAME/KEY: misc_feature
<222> LOCATION: (133)..(133)
<223> OTHER INFORMATION: Xaa can be any naturally occurring amino acid

<400> SEQUENCE: 59

Met Asp Met Arg Val Pro Ala Gln Leu Leu Gly Leu Leu Leu Leu Trp
1               5                   10                  15

Leu Pro Gly Ala Arg Cys Val Ile Trp Met Thr Gln Ser Pro Ser Leu
            20                  25                  30

Leu Ser Ala Ser Thr Gly Asp Arg Val Thr Ile Ser Cys Arg Met Ser
        35                  40                  45

```
Gln Gly Ile Arg Ser Tyr Leu Ala Trp Tyr Gln Gln Lys Pro Gly Lys
        50                  55                  60

Ala Pro Glu Leu Leu Ile Tyr Ala Ala Ser Thr Leu Gln Ser Gly Val
 65                  70                  75                  80

Pro Ser Arg Phe Ser Gly Ser Gly Ser Gly Thr Asp Phe Thr Leu Thr
                    85                  90                  95

Ile Ser Ser Leu Gln Ser Glu Asp Phe Ala Thr Tyr Tyr Cys Gln Gln
                100                 105                 110

Tyr Tyr Ser Phe Pro Tyr Thr Phe Gly Gln Gly Thr Lys Leu Glu Ile
            115                 120                 125

Lys Arg Thr Val Xaa
        130

<210> SEQ ID NO 60
<211> LENGTH: 438
<212> TYPE: DNA
<213> ORGANISM: Homo sapiens

<400> SEQUENCE: 60
gacccgtcga ccaccatgga ctggacctgg aggttcctct tgtggtggc agcagctaca       60 ggtgtccagt cccaggtcca gctggtgcag tctggggctg aggtgaagaa gcctgggtcc     120
tcggtgaagg tctcctgcaa gacttctgga ggcaccttca gcaactttgc tatcagctgg     180
gtgcgacagg cccctggaca agggcttgag tggatgggag ggatcatccc tatctttggt     240
tcaacaaact acgcacagaa gttccagggc agagtcacga ttaacgcgga cgaatccacg     300
agcacagcct acatggagct gagcagtctg agatctgagg acacggccgt gtattactgt     360
gcgggtggag acaaatatgg tccttactac tttcactact ggggccaggg aacccttgtc     420
accgtctcct cagctagc                                                   438

<210> SEQ ID NO 61
<211> LENGTH: 141
<212> TYPE: PRT
<213> ORGANISM: Homo sapiens

<400> SEQUENCE: 61

Met Asp Trp Thr Trp Arg Phe Leu Phe Val Val Ala Ala Ala Thr Gly
  1               5                  10                  15

Val Gln Ser Gln Val Gln Leu Val Gln Ser Gly Ala Glu Val Lys Lys
                 20                  25                  30

Pro Gly Ser Ser Val Lys Val Ser Cys Lys Thr Ser Gly Gly Thr Phe
             35                  40                  45

Ser Asn Phe Ala Ile Ser Trp Val Arg Gln Ala Pro Gly Gln Gly Leu
         50                  55                  60

Glu Trp Met Gly Gly Ile Ile Pro Ile Phe Gly Ser Thr Asn Tyr Ala
 65                  70                  75                  80

Gln Lys Phe Gln Gly Arg Val Thr Ile Asn Ala Asp Glu Ser Thr Ser
                 85                  90                  95

Thr Ala Tyr Met Glu Leu Ser Ser Leu Arg Ser Glu Asp Thr Ala Val
            100                 105                 110

Tyr Tyr Cys Ala Gly Gly Asp Lys Tyr Gly Pro Tyr Tyr Phe His Tyr
        115                 120                 125

Trp Gly Gln Gly Thr Leu Val Thr Val Ser Ser Ala Ser
    130                 135                 140

<210> SEQ ID NO 62
<211> LENGTH: 407
```

```
<212> TYPE: DNA
<213> ORGANISM: Homo sapiens

<400> SEQUENCE: 62
agatctctca ccatggacat gagggtcctc gctcagctcc tggggctcct gctgctctgt      60
ttcccaggtg ccagatgtga catccagatg acccagtctc catcctcact gtctgcatct     120
gtaggagaca gagtcaccat cacttgtcgg gcgagtcagg gtattagcag ctggttagcc     180
tggtatcagc agaaaccaga gaaagcccct aagtccctga tctatgctgc atccagtttg     240
caaagtgggg tcccatcaag gttcagcggc agtggatctg ggacagattt cactctcacc     300
atcagcagcc tgcagcctga agattttgca acttattact gccaacagta taatagttac     360
ccgtacactt ttggccaggg gaccaagctg gagatcaaac gtacggt                   407

<210> SEQ ID NO 63
<211> LENGTH: 132
<212> TYPE: PRT
<213> ORGANISM: Homo sapiens
<220> FEATURE:
<221> NAME/KEY: misc_feature
<222> LOCATION: (132)..(132)
<223> OTHER INFORMATION: Xaa can be any naturally occurring amino acid

<400> SEQUENCE: 63

Met Asp Met Arg Val Leu Ala Gln Leu Gly Leu Leu Leu Leu Cys
1               5                  10                  15

Phe Pro Gly Ala Arg Cys Asp Ile Gln Met Thr Gln Ser Pro Ser
                20                  25                  30

Leu Ser Ala Ser Val Gly Asp Arg Val Thr Ile Thr Cys Arg Ala Ser
        35                  40                  45

Gln Gly Ile Ser Ser Trp Leu Ala Trp Tyr Gln Lys Pro Glu Lys
    50                  55                  60

Ala Pro Lys Ser Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Asn Ser Tyr Pro Tyr Thr Phe Gly Gln Gly Thr Lys Leu Glu Ile
        115                 120                 125

Lys Arg Thr Xaa
    130

<210> SEQ ID NO 64
<211> LENGTH: 437
<212> TYPE: DNA
<213> ORGANISM: Homo sapiens

<400> SEQUENCE: 64
tcgaccccat ggactggacc tggaggttcc tctttgtggt ggcagcagct acaggtgtcc      60
agtcccaggt ccagctggtg cagtctgggg ctgaggtgaa gaagcctggg tcctcggtga     120
aggtctcctg caaggcttct ggaggcacct tcagcagcta tgctatcagc tgggtgcgac     180
aggcccctgg acaagggctt gagtgggtgg gagggatcat ccctatcttt ggtacagcaa     240
actacgcaca gaagttccag ggcagagtca cgattaccgc ggacgaatcc acgagcacag     300
cctacatgga gctgagcagc ctgagatctg aggacacggc cgtgtattac tgtgcgagag     360
gacacaaata tggcccctac tactttgact actggggcca gggaaccctg gtcaccgtct     420
```

-continued cctcagctag caccaag　　　　　　　　　　　　　　　　　　　　　　　　437

<210> SEQ ID NO 65
<211> LENGTH: 143
<212> TYPE: PRT
<213> ORGANISM: Homo sapiens

<400> SEQUENCE: 65

Met Asp Trp Thr Trp Arg Phe Leu Phe Val Val Ala Ala Ala Thr Gly
1               5                   10                  15

Val Gln Ser Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Ser Tyr Ala Ile Ser Trp Val Arg Gln Ala Pro Gly Gln Gly Leu
    50                  55                  60

Glu Trp Val Gly Gly Ile Ile Pro Ile Phe Gly Thr Ala Asn Tyr Ala
65                  70                  75                  80

Gln Lys Phe Gln Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly His Lys Tyr Gly Pro Tyr Tyr Phe Asp Tyr
        115                 120                 125

Trp Gly Gln Gly Thr Leu Val Thr Val Ser Ser Ala Ser Thr Lys
    130                 135                 140

<210> SEQ ID NO 66
<211> LENGTH: 411
<212> TYPE: DNA
<213> ORGANISM: Homo sapiens

<400> SEQUENCE: 66
agatctctca ccatggacat gagggtcctc gctcagctcc tggggctcct gctgctctgt    60
ttcccaggtg ccagatgtga catccagatg acccagtctc catcctcact gtctgcatct   120
gtaggagaca gagtcaccat cacttgtcgg gcgagtcagg gtattagcag ctggttagcc   180
tggtatcagc agaaaccaga gaagccccct aagtccctga tctatgctgc atccagtttg   240
caaagtgggg tcccatcaag gttcagcggc agtggatctg ggacagattt cactctcacc   300
atcagcagcc tgcagcctga agattttgca acttattact gccaacagta taatagttac   360
cctcggacgt tcggccaagg gaccaaggtg gaaatcaaac gtacggtggc t           411

<210> SEQ ID NO 67
<211> LENGTH: 133
<212> TYPE: PRT
<213> ORGANISM: Homo sapiens

<400> SEQUENCE: 67

Met Asp Met Arg Val Leu Ala Gln Leu Leu Gly Leu Leu Leu Leu Cys
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Trp Leu Ala Trp Tyr Gln Gln Lys Pro Glu Lys
    50                  55                  60

Ala Pro Lys Ser Leu Ile Tyr Ala Ala Ser Ser Leu Gln Ser Gly Val

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
            85                  90                  95

Tyr Asn Ser Tyr Pro Arg Thr Phe Gly Gln Gly Thr Lys Val Glu Ile
        100                 105                 110

Lys Arg Thr Val Ala
    115                 120                 125

130

<210> SEQ ID NO 68
<211> LENGTH: 435
<212> TYPE: DNA
<213> ORGANISM: Homo sapiens

<400> SEQUENCE: 68
tcgaccacca tggactggac ctggaggttc ctctttgtgg tggcagcagc tacaggtgtc      60
cagtcccagg tccagctggt gcagtctggg gctgaggtga agaagcctgg atcctcggtg     120
aaggtctcct gcatggcttc aggaggcacc gtcagcagct acgctatcag ctgggtgcga     180
caggcccctg gacaagggct tgagtggatg ggagagatca tccctatctt tggtatagta     240
aactacgcac agaagttcca gggcagagtc acgattaccg cggacgaatc cacgaacaca     300
gcctacatgg agctgagcag cctgagatct gaggacacgg ccatatatta ctgtgcgaga     360
gagacagcag tggctggtat tcttggttac tggggccagg gaaccctggt caccgtctcc     420
tcagctagca ccaag                                                      435

<210> SEQ ID NO 69
<211> LENGTH: 142
<212> TYPE: PRT
<213> ORGANISM: Homo sapiens

<400> SEQUENCE: 69

Met Asp Trp Thr Trp Arg Phe Leu Phe Val Val Ala Ala Ala Thr Gly
1               5                   10                  15

Val Gln Ser Gln Val Gln Leu Val Gln Ser Gly Ala Glu Val Lys Lys
            20                  25                  30

Pro Gly Ser Ser Val Lys Val Ser Cys Met Ala Ser Gly Gly Thr Val
        35                  40                  45

Ser Ser Tyr Ala Ile Ser Trp Val Arg Gln Ala Pro Gly Gln Gly Leu
    50                  55                  60

Glu Trp Met Gly Glu Ile Ile Pro Ile Phe Gly Ile Val Asn Tyr Ala
65                  70                  75                  80

Gln Lys Phe Gln Gly Arg Val Thr Ile Thr Ala Asp Glu Ser Thr Asn
            85                  90                  95

Thr Ala Tyr Met Glu Leu Ser Ser Leu Arg Ser Glu Asp Thr Ala Ile
        100                 105                 110

Tyr Tyr Cys Ala Arg Glu Thr Ala Val Ala Gly Ile Leu Gly Tyr Trp
    115                 120                 125

Gly Gln Gly Thr Leu Val Thr Val Ser Ser Ala Ser Thr Lys
130                 135                 140

<210> SEQ ID NO 70
<211> LENGTH: 414
<212> TYPE: DNA
<213> ORGANISM: Homo sapiens

<400> SEQUENCE: 70

```
agatctctca ccatggacat gagggtcctc gctcagctcc tggggctcct gctgctctgt    60
ttcccaggtg ccagatgtga catccagatg acccagtctc catcctcact gtctgcatct   120
gtaggagaca gagtcaccat cacttgtcgg gcgagtcagg gtattagcag ctggttagcc   180
tggtatcagc agaaaccaga gaaagcccct aagtccctga tctatgctgc atccagtttg   240
caaagtgggg tcccatcaag gttcagcggc agtggatctg ggacagattt cactctcacc   300
atcagcagcc tgcagcctga agattttgca acttattact gccaacagta taatagttac   360
ccgtacactt ttggccaggg gaccaagctg gagatcaaac gtacggtggc tgca         414
```

<210> SEQ ID NO 71
<211> LENGTH: 134
<212> TYPE: PRT
<213> ORGANISM: Homo sapiens

<400> SEQUENCE: 71

Met Asp Met Arg Val Leu Ala Gln Leu Leu Gly Leu Leu Leu Leu Cys
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Trp Leu Ala Trp Tyr Gln Gln Lys Pro Glu Lys
    50                  55                  60

Ala Pro Lys Ser Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Asn Ser Tyr Pro Tyr Thr Phe Gly Gln Gly Thr Lys Leu Glu Ile
        115                 120                 125

Lys Arg Thr Val Ala Ala
    130

<210> SEQ ID NO 72
<211> LENGTH: 423
<212> TYPE: DNA
<213> ORGANISM: Homo sapiens

<400> SEQUENCE: 72

```
cgacccacca tggaactggg gctccgctgg gttttccttg ttgctatttt agaaggtgtc    60
cagtgtgagg tgcagttggt ggagtctggg ggaggcctgg tcaagcctgg ggggtccctg   120
agactctcct gtgcagcctc tggattcacc ttcagtagcc ataacatgaa ctgggtccgc   180
caggctccag ggaaggggct ggagtgggtc tcatccatta gtagtagtag tagttacata   240
tattatgcag actcagtgaa gggccgattc accatctcca gagacaacgc caagaactca   300
ctgtatctgc aaatgaacag cctgagagcc gaggacacgg ctgtgtatta ctgtgcgaga   360
gaggactggg gctactttga ctactggggc cagggaaccc tggtcaccgt ctcctcagct   420
agc                                                                423
```

<210> SEQ ID NO 73
<211> LENGTH: 140
<212> TYPE: PRT
<213> ORGANISM: Homo sapiens

```
<400> SEQUENCE: 73

Met Glu Leu Gly Leu Arg Trp Val Phe Leu Val Ala Ile Leu Glu Gly
1               5                   10                  15

Val Gln Cys Glu Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser His Asn Met Asn Trp Val Arg Gln Ala Pro Gly Lys Gly Leu
    50                  55                  60

Glu Trp Val Ser Ser Ile Ser Ser Ser Ser Tyr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Gly Asp Trp Gly Tyr Phe Asp Tyr Trp Gly Gln
        115                 120                 125

Gly Thr Leu Val Thr Val Ser Ser Ala Ser Thr Lys
    130                 135                 140

<210> SEQ ID NO 74
<211> LENGTH: 407
<212> TYPE: DNA
<213> ORGANISM: Homo sapiens

<400> SEQUENCE: 74
agatctctca ccatggacat gagggtcccc gctcagctcc tggggcttct gctgctctgg    60
ctcccaggtg ccagatgtgc catccagttg acccagtctc catcctccct gtctgcatct   120
gtaggagaca gagtcaccat cacttgccgg gcaagtcagg gcattagcag tgatttagcc   180
tggtatcagc agaaaccagg gaaagctcct aagctcctga tctatgatgc ctccagtttg   240
gaaagtgggg tcccatcaag gttcagcggc agtggatctg ggacagattt cactctcacc   300
atcagcagcc tgcagcctga agattttgca acttattact gtcaacagtt taatagttac   360
ccattcactt tcggccctgg gaccaaagtg gatatcaaac gtacggt                 407

<210> SEQ ID NO 75
<211> LENGTH: 134
<212> TYPE: PRT
<213> ORGANISM: Homo sapiens

<400> SEQUENCE: 75

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Asp Leu Ala Trp Tyr Gln Gln Lys Pro Gly Lys
    50                  55                  60

Ala Pro Lys Leu Leu Ile Tyr Asp Ala Ser Ser Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110
```

```
Phe Asn Ser Tyr Pro Phe Thr Phe Gly Pro Gly Thr Lys Val Asp Ile
            115                 120                 125
Lys Arg Thr Val Ala Ala
    130
```

<210> SEQ ID NO 76
<211> LENGTH: 433
<212> TYPE: DNA
<213> ORGANISM: Homo sapiens

<400> SEQUENCE: 76

| | | | | | |
|---|---|---|---|---|---|
| gtcgaccacc | atgggatgga | gctggatctt | tctctttctc | gtgtcaggaa | ctggaggtgt | 60 |
| cctctctgag | gtccagctgc | aacagtctgg | acctgagctg | gtgaagcctg | ggcttcagt | 120 |
| aaagatgtcc | tgcaaggctt | ctggatacac | cttcactgac | tactacatga | agtgggtgaa | 180 |
| acagagccat | ggaaagagcc | ttgagtggat | tggagatatt | attcctagca | atggtgccac | 240 |
| tttctacaac | cagaagttca | agggcaaggc | cactttgact | gtggacagat | cctccagcac | 300 |
| agcctacatg | cacctcaaca | gcctgacatc | tgaggactct | gcagtctatt | actgtacaag | 360 |
| atcgcattta | ctgcgggcct | cctggtttgc | ttactggggc | caagggactc | tggtcactgt | 420 |
| ctctgcagct | agc | | | | | 433 |

<210> SEQ ID NO 77
<211> LENGTH: 141
<212> TYPE: PRT
<213> ORGANISM: Homo sapiens

<400> SEQUENCE: 77

```
Met Gly Trp Ser Trp Ile Phe Leu Phe Leu Val Ser Gly Thr Gly Gly
1               5                   10                  15
Val Leu Ser Glu Val Gln Leu Gln Gln Ser Gly Pro Glu Leu Val Lys
                20                  25                  30
Pro Gly Ala Ser Val Lys Met Ser Cys Lys Ala Ser Gly Tyr Thr Phe
            35                  40                  45
Thr Asp Tyr Tyr Met Lys Trp Val Lys Gln Ser His Gly Lys Ser Leu
        50                  55                  60
Glu Trp Ile Gly Asp Ile Ile Pro Ser Asn Gly Ala Thr Phe Tyr Asn
65                  70                  75                  80
Gln Lys Phe Lys Gly Lys Ala Thr Leu Thr Val Asp Arg Ser Ser Ser
                85                  90                  95
Thr Ala Tyr Met His Leu Asn Ser Leu Thr Ser Glu Asp Ser Ala Val
            100                 105                 110
Tyr Tyr Cys Thr Arg Ser His Leu Leu Arg Ala Ser Trp Phe Ala Tyr
        115                 120                 125
Trp Gly Gln Gly Thr Leu Val Thr Val Ser Ala Ala Ser
    130                 135                 140
```

<210> SEQ ID NO 78
<211> LENGTH: 412
<212> TYPE: DNA
<213> ORGANISM: Homo sapiens

<400> SEQUENCE: 78

| | | | | | |
|---|---|---|---|---|---|
| agatctcacc | atggaatcac | agactcaggt | cctcatgtcc | ctgctgttct | gggtatctgg | 60 |
| tacctgtggg | gactttgtga | tgacacagtc | tccatcctcc | ctgactgtga | cagcaggaga | 120 |
| gaaggtcact | atgagctgca | agtctagtca | gagtctgtta | aacagtggaa | atcaaaagaa | 180 |
| ctacttgacc | tggtatctgc | agaaaccagg | gcagcctcct | aaattgttga | tctattgggc | 240 |

```
atccactagg gaatctgggg tccctgatcg cttcacaggc agtggatctg gaacagattt    300
cactctcacc atcagcagtg tgcaggctga agacctggca gtttattact gtcagaatga    360
ttatagttat ccgtacacgt tcggagggg gaccaagctg gaaataaaac gt             412
```

<210> SEQ ID NO 79
<211> LENGTH: 134
<212> TYPE: PRT
<213> ORGANISM: Homo sapiens

<400> SEQUENCE: 79

```
Met Glu Ser Gln Thr Gln Val Leu Met Ser Leu Leu Phe Trp Val Ser
1               5                   10                  15

Gly Thr Cys Gly Asp Phe Val Met Thr Gln Ser Pro Ser Ser Leu Thr
            20                  25                  30

Val Thr Ala Gly Glu Lys Val Thr Met Ser Cys Lys Ser Ser Gln Ser
        35                  40                  45

Leu Leu Asn Ser Gly Asn Gln Lys Asn Tyr Leu Thr Trp Tyr Leu Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Asn Asp Tyr Ser Tyr Pro Tyr Thr Phe Gly Gly Gly Thr
        115                 120                 125

Lys Leu Glu Ile Lys Arg
    130
```

<210> SEQ ID NO 80
<211> LENGTH: 37
<212> TYPE: DNA
<213> ORGANISM: Artificial
<220> FEATURE:
<223> OTHER INFORMATION: primer hCD116Fw-MfeI

<400> SEQUENCE: 80

```
cggcaattgc caccatgctt ctcctggtga caagcct                              37
```

<210> SEQ ID NO 81
<211> LENGTH: 31
<212> TYPE: DNA
<213> ORGANISM: Artificial
<220> FEATURE:
<223> OTHER INFORMATION: primer hCD116Rv-NotI

<400> SEQUENCE: 81

```
attgcggccg ctcaggtaat ttccttcacg g                                    31
```

<210> SEQ ID NO 82
<211> LENGTH: 37
<212> TYPE: DNA
<213> ORGANISM: Artificial
<220> FEATURE:
<223> OTHER INFORMATION: primer hCD116Fw-MfeI

<400> SEQUENCE: 82

```
cggcaattgc caccatgctt ctcctggtga caagcct                              37
```

<210> SEQ ID NO 83

```
<211> LENGTH: 31
<212> TYPE: DNA
<213> ORGANISM: Artificial
<220> FEATURE:
<223> OTHER INFORMATION: primer hCD116Rv-NotI

<400> SEQUENCE: 83
attgcggccg ctcaggtaat ttccttcacg g                             31

<210> SEQ ID NO 84
<211> LENGTH: 37
<212> TYPE: DNA
<213> ORGANISM: Artificial
<220> FEATURE:
<223> OTHER INFORMATION: primer hCD116Fw-MfeI

<400> SEQUENCE: 84
cggcaattgc caccatgctt ctcctggtga caagcct                       37

<210> SEQ ID NO 85
<211> LENGTH: 31
<212> TYPE: DNA
<213> ORGANISM: Artificial
<220> FEATURE:
<223> OTHER INFORMATION: primer hCD116Rv-NotI

<400> SEQUENCE: 85
attgcggccg ctcaggtaat ttccttcacg g                             31

<210> SEQ ID NO 86
<211> LENGTH: 20
<212> TYPE: DNA
<213> ORGANISM: Artificial
<220> FEATURE:
<223> OTHER INFORMATION: primer hCD116SeqFw1

<400> SEQUENCE: 86
tgaactgtac ctgggcgagg                                          20

<210> SEQ ID NO 87
<211> LENGTH: 20
<212> TYPE: DNA
<213> ORGANISM: Artificial
<220> FEATURE:
<223> OTHER INFORMATION: primer hCD116SeqFw2

<400> SEQUENCE: 87
ctggcacgga aaacctactg                                          20

<210> SEQ ID NO 88
<211> LENGTH: 20
<212> TYPE: DNA
<213> ORGANISM: Artificial
<220> FEATURE:
<223> OTHER INFORMATION: primer hCD116SeqRv1

<400> SEQUENCE: 88
cctgaatttg gataaagcag                                          20

<210> SEQ ID NO 89
<211> LENGTH: 20
<212> TYPE: DNA
<213> ORGANISM: Artificial
<220> FEATURE:
<223> OTHER INFORMATION: primer T7

<400> SEQUENCE: 89
```

-continued

```
taatacgact cactataggg                                              20

<210> SEQ ID NO 90
<211> LENGTH: 40
<212> TYPE: DNA
<213> ORGANISM: Artificial
<220> FEATURE:
<223> OTHER INFORMATION: primer hCD123-C-FLAG-R1

<400> SEQUENCE: 90
tcgtcatcgt ccttgtagtc agttttctgc acgacctgta                        40

<210> SEQ ID NO 91
<211> LENGTH: 34
<212> TYPE: DNA
<213> ORGANISM: Artificial
<220> FEATURE:
<223> OTHER INFORMATION: primer IL-3RA_Fw

<400> SEQUENCE: 91
cggcaattgc caccatggtc ctcctttggc tcac                              34

<210> SEQ ID NO 92
<211> LENGTH: 39
<212> TYPE: DNA
<213> ORGANISM: Artificial
<220> FEATURE:
<223> OTHER INFORMATION: primer C-FLAG-NotR2

<400> SEQUENCE: 92
aaaagcggcc gctcacttgt cgtcatcgtc cttgtagtc                         39

<210> SEQ ID NO 93
<211> LENGTH: 20
<212> TYPE: DNA
<213> ORGANISM: Artificial
<220> FEATURE:
<223> OTHER INFORMATION: primer pEGFP-N1-Fw

<400> SEQUENCE: 93
cgtgtacggt gggaggtcta                                              20

<210> SEQ ID NO 94
<211> LENGTH: 19
<212> TYPE: DNA
<213> ORGANISM: Artificial
<220> FEATURE:
<223> OTHER INFORMATION: primer pEGFP-N1-Re

<400> SEQUENCE: 94
tttatgtttc aggttcagg                                               19

<210> SEQ ID NO 95
<211> LENGTH: 20
<212> TYPE: DNA
<213> ORGANISM: Artificial
<220> FEATURE:
<223> OTHER INFORMATION: primer pEGFP-N1-Fw

<400> SEQUENCE: 95
cgtgtacggt gggaggtcta                                              20

<210> SEQ ID NO 96
<211> LENGTH: 19
<212> TYPE: DNA
<213> ORGANISM: Artificial
<220> FEATURE:
```

<223> OTHER INFORMATION: primer pEGFP-N1-Re

<400> SEQUENCE: 96
tttatgtttc aggttcagg                                              19

<210> SEQ ID NO 97
<211> LENGTH: 28
<212> TYPE: DNA
<213> ORGANISM: Artificial
<220> FEATURE:
<223> OTHER INFORMATION: primer CD123R11pEGFPN1

<400> SEQUENCE: 97
aaaggtaccg aattcgaagc ttgagctc                                    28

<210> SEQ ID NO 98
<211> LENGTH: 27
<212> TYPE: DNA
<213> ORGANISM: Artificial
<220> FEATURE:
<223> OTHER INFORMATION: primer CD123F11

<400> SEQUENCE: 98
aaaggtaccg ggaagccttg ggcaggt                                     27

<210> SEQ ID NO 99
<211> LENGTH: 30
<212> TYPE: DNA
<213> ORGANISM: Artificial
<220> FEATURE:
<223> OTHER INFORMATION: primer CD123R12-2

<400> SEQUENCE: 99
aaaggtacca ctgttctcag ggaagaggat                                  30

<210> SEQ ID NO 100
<211> LENGTH: 29
<212> TYPE: DNA
<213> ORGANISM: Artificial
<220> FEATURE:
<223> OTHER INFORMATION: primer CD123F12-2

<400> SEQUENCE: 100
aaaggtaccc agattgagat attaactcc                                   29

<210> SEQ ID NO 101
<211> LENGTH: 27
<212> TYPE: DNA
<213> ORGANISM: Artificial
<220> FEATURE:
<223> OTHER INFORMATION: primer CD123R13

<400> SEQUENCE: 101
aaaggtacct gaaaagacga caaactt                                     27

<210> SEQ ID NO 102
<211> LENGTH: 27
<212> TYPE: DNA
<213> ORGANISM: Artificial
<220> FEATURE:
<223> OTHER INFORMATION: primer CD123F13

<400> SEQUENCE: 102
aaaggtacct cgctgctgat cgcgctg                                     27

<210> SEQ ID NO 103

```
<211> LENGTH: 20
<212> TYPE: DNA
<213> ORGANISM: Artificial
<220> FEATURE:
<223> OTHER INFORMATION: primer pEGFP-N1-Fw

<400> SEQUENCE: 103
cgtgtacggt gggaggtcta                                                    20

<210> SEQ ID NO 104
<211> LENGTH: 19
<212> TYPE: DNA
<213> ORGANISM: Artificial
<220> FEATURE:
<223> OTHER INFORMATION: primer pEGFP-N1-Re

<400> SEQUENCE: 104
tttatgtttc aggttcagg                                                     19

<210> SEQ ID NO 105
<211> LENGTH: 33
<212> TYPE: DNA
<213> ORGANISM: Artificial
<220> FEATURE:
<223> OTHER INFORMATION: primer GM-CSFRF11

<400> SEQUENCE: 105
aaaggtaccg ccaccatgct tctcctggtg aca                                     33

<210> SEQ ID NO 106
<211> LENGTH: 27
<212> TYPE: DNA
<213> ORGANISM: Artificial
<220> FEATURE:
<223> OTHER INFORMATION: primer GM-CSFRR11

<400> SEQUENCE: 106
aaaggtacct gaatttggat aaagcag                                            27

<210> SEQ ID NO 107
<211> LENGTH: 27
<212> TYPE: DNA
<213> ORGANISM: Artificial
<220> FEATURE:
<223> OTHER INFORMATION: primer GM-CSFRF12

<400> SEQUENCE: 107
aaaggtaccg gaagggaggg taccgct                                            27

<210> SEQ ID NO 108
<211> LENGTH: 27
<212> TYPE: DNA
<213> ORGANISM: Artificial
<220> FEATURE:
<223> OTHER INFORMATION: primer GM-CSFRR12

<400> SEQUENCE: 108
aaaggtaccc tttgtgtcca aaagtga                                            27

<210> SEQ ID NO 109
<211> LENGTH: 27
<212> TYPE: DNA
<213> ORGANISM: Artificial
<220> FEATURE:
<223> OTHER INFORMATION: primer GM-CSFRF13

<400> SEQUENCE: 109
```

```
aaaggtacca aaatagaacg attcaac                                              27

<210> SEQ ID NO 110
<211> LENGTH: 27
<212> TYPE: DNA
<213> ORGANISM: Artificial
<220> FEATURE:
<223> OTHER INFORMATION: primer GM-CSFRR13

<400> SEQUENCE: 110
aaaggtacca atgtacacag agccgag                                              27

<210> SEQ ID NO 111
<211> LENGTH: 20
<212> TYPE: DNA
<213> ORGANISM: Artificial
<220> FEATURE:
<223> OTHER INFORMATION: primer pEGFP-N1-Fw

<400> SEQUENCE: 111
cgtgtacggt gggaggtcta                                                      20

<210> SEQ ID NO 112
<211> LENGTH: 19
<212> TYPE: DNA
<213> ORGANISM: Artificial
<220> FEATURE:
<223> OTHER INFORMATION: primer pEGFP-N1-Re

<400> SEQUENCE: 112
tttatgtttc aggttcagg                                                       19

<210> SEQ ID NO 113
<211> LENGTH: 5
<212> TYPE: PRT
<213> ORGANISM: Homo sapiens

<400> SEQUENCE: 113

Thr Tyr Ala Ile Ser
1               5

<210> SEQ ID NO 114
<211> LENGTH: 17
<212> TYPE: PRT
<213> ORGANISM: Homo sapiens

<400> SEQUENCE: 114

Gly Ile Ile Pro Ile Phe Gly Ile Val Asn Tyr Ala Gln Lys Phe Gln
1               5                   10                  15

Gly

<210> SEQ ID NO 115
<211> LENGTH: 11
<212> TYPE: PRT
<213> ORGANISM: Homo sapiens

<400> SEQUENCE: 115

Gly Gly Gly Ser Gly Pro Asp Val Leu Asp Ile
1               5                   10

<210> SEQ ID NO 116
<211> LENGTH: 5
<212> TYPE: PRT
<213> ORGANISM: Homo sapiens

<400> SEQUENCE: 116
```

```
Thr Tyr Ala Ile Ser
1               5

<210> SEQ ID NO 117
<211> LENGTH: 17
<212> TYPE: PRT
<213> ORGANISM: Homo sapiens

<400> SEQUENCE: 117

Gly Leu Ile Pro Ile Phe Asp Ile Glu Asn Tyr Ala Gln Lys Phe Gln
1               5                   10                  15

Gly

<210> SEQ ID NO 118
<211> LENGTH: 11
<212> TYPE: PRT
<213> ORGANISM: Homo sapiens

<400> SEQUENCE: 118

Gly Gly Gly Ser Gly Pro Asp Val Leu Asp Ile
1               5                   10

<210> SEQ ID NO 119
<211> LENGTH: 5
<212> TYPE: PRT
<213> ORGANISM: Homo sapiens

<400> SEQUENCE: 119

Asn Phe Ala Ile Ser
1               5

<210> SEQ ID NO 120
<211> LENGTH: 17
<212> TYPE: PRT
<213> ORGANISM: Homo sapiens

<400> SEQUENCE: 120

Gly Ile Ile Pro Ile Phe Gly Ser Thr Asn Tyr Ala Gln Lys Phe Gln
1               5                   10                  15

Gly

<210> SEQ ID NO 121
<211> LENGTH: 11
<212> TYPE: PRT
<213> ORGANISM: Homo sapiens

<400> SEQUENCE: 121

Gly Asp Lys Tyr Gly Pro Tyr Tyr Phe His Tyr
1               5                   10

<210> SEQ ID NO 122
<211> LENGTH: 5
<212> TYPE: PRT
<213> ORGANISM: Homo sapiens

<400> SEQUENCE: 122

Ser Tyr Ala Ile Ser
1               5

<210> SEQ ID NO 123
<211> LENGTH: 17
<212> TYPE: PRT
<213> ORGANISM: Homo sapiens
```

```
<400> SEQUENCE: 123

Gly Ile Ile Pro Ile Phe Gly Thr Ala Asn Tyr Ala Gln Lys Phe Gln
1               5                   10                  15

Gly

<210> SEQ ID NO 124
<211> LENGTH: 11
<212> TYPE: PRT
<213> ORGANISM: Homo sapiens

<400> SEQUENCE: 124

Gly His Lys Tyr Gly Pro Tyr Tyr Phe Asp Tyr
1               5                   10

<210> SEQ ID NO 125
<211> LENGTH: 5
<212> TYPE: PRT
<213> ORGANISM: Homo sapiens

<400> SEQUENCE: 125

Ser Tyr Ala Ile Ser
1               5

<210> SEQ ID NO 126
<211> LENGTH: 17
<212> TYPE: PRT
<213> ORGANISM: Homo sapiens

<400> SEQUENCE: 126

Glu Ile Ile Pro Ile Phe Gly Ile Val Asn Tyr Ala Gln Lys Phe Gln
1               5                   10                  15

Gly

<210> SEQ ID NO 127
<211> LENGTH: 10
<212> TYPE: PRT
<213> ORGANISM: Homo sapiens

<400> SEQUENCE: 127

Glu Thr Ala Val Ala Gly Ile Leu Gly Tyr
1               5                   10

<210> SEQ ID NO 128
<211> LENGTH: 5
<212> TYPE: PRT
<213> ORGANISM: Homo sapiens

<400> SEQUENCE: 128

Ser His Asn Met Asn
1               5

<210> SEQ ID NO 129
<211> LENGTH: 17
<212> TYPE: PRT
<213> ORGANISM: Homo sapiens

<400> SEQUENCE: 129

Ser Ile Ser Ser Ser Ser Ser Tyr Ile Tyr Tyr Ala Asp Ser Val Lys
1               5                   10                  15

Gly

<210> SEQ ID NO 130
<211> LENGTH: 7
```

```
<212> TYPE: PRT
<213> ORGANISM: Homo sapiens

<400> SEQUENCE: 130

Glu Asp Trp Gly Tyr Phe Asp
1               5

<210> SEQ ID NO 131
<211> LENGTH: 11
<212> TYPE: PRT
<213> ORGANISM: Homo sapiens

<400> SEQUENCE: 131

Arg Met Ser Gln Gly Ile Arg Ser Tyr Leu Ala
1               5                   10

<210> SEQ ID NO 132
<211> LENGTH: 7
<212> TYPE: PRT
<213> ORGANISM: Homo sapiens

<400> SEQUENCE: 132

Ala Ala Ser Thr Leu Gln Ser
1               5

<210> SEQ ID NO 133
<211> LENGTH: 9
<212> TYPE: PRT
<213> ORGANISM: Homo sapiens

<400> SEQUENCE: 133

Gln Gln Tyr Tyr Ser Phe Pro Tyr Thr
1               5

<210> SEQ ID NO 134
<211> LENGTH: 11
<212> TYPE: PRT
<213> ORGANISM: Homo sapiens

<400> SEQUENCE: 134

Arg Met Ser Gln Gly Ile Arg Ser Tyr Leu Ala
1               5                   10

<210> SEQ ID NO 135
<211> LENGTH: 7
<212> TYPE: PRT
<213> ORGANISM: Homo sapiens

<400> SEQUENCE: 135

Ala Ala Ser Thr Leu Gln Ser
1               5

<210> SEQ ID NO 136
<211> LENGTH: 9
<212> TYPE: PRT
<213> ORGANISM: Homo sapiens

<400> SEQUENCE: 136

Gln Gln Tyr Tyr Ser Phe Pro Tyr Thr
1               5

<210> SEQ ID NO 137
<211> LENGTH: 11
<212> TYPE: PRT
<213> ORGANISM: Homo sapiens
```

```
<400> SEQUENCE: 137

Arg Ala Ser Gln Gly Ile Ser Ser Trp Leu Ala
1               5                   10

<210> SEQ ID NO 138
<211> LENGTH: 7
<212> TYPE: PRT
<213> ORGANISM: Homo sapiens

<400> SEQUENCE: 138

Ala Ala Ser Ser Leu Gln Ser
1               5

<210> SEQ ID NO 139
<211> LENGTH: 9
<212> TYPE: PRT
<213> ORGANISM: Homo sapiens

<400> SEQUENCE: 139

Gln Gln Tyr Asn Ser Tyr Pro Tyr Thr
1               5

<210> SEQ ID NO 140
<211> LENGTH: 11
<212> TYPE: PRT
<213> ORGANISM: Homo sapiens

<400> SEQUENCE: 140

Arg Ala Ser Gln Gly Ile Ser Ser Trp Leu Ala
1               5                   10

<210> SEQ ID NO 141
<211> LENGTH: 7
<212> TYPE: PRT
<213> ORGANISM: Homo sapiens

<400> SEQUENCE: 141

Ala Ala Ser Ser Leu Gln Ser
1               5

<210> SEQ ID NO 142
<211> LENGTH: 9
<212> TYPE: PRT
<213> ORGANISM: Homo sapiens

<400> SEQUENCE: 142

Gln Gln Tyr Asn Ser Tyr Pro Arg Thr
1               5

<210> SEQ ID NO 143
<211> LENGTH: 11
<212> TYPE: PRT
<213> ORGANISM: Homo sapiens

<400> SEQUENCE: 143

Arg Ala Ser Gln Gly Ile Ser Ser Trp Leu Ala
1               5                   10

<210> SEQ ID NO 144
<211> LENGTH: 7
<212> TYPE: PRT
<213> ORGANISM: Homo sapiens

<400> SEQUENCE: 144

Ala Ala Ser Ser Leu Gln Ser
```

<210> SEQ ID NO 145
<211> LENGTH: 9
<212> TYPE: PRT
<213> ORGANISM: Homo sapiens

<400> SEQUENCE: 145

Gln Gln Tyr Asn Ser Tyr Pro Tyr Thr
1               5

<210> SEQ ID NO 146
<211> LENGTH: 11
<212> TYPE: PRT
<213> ORGANISM: Homo sapiens

<400> SEQUENCE: 146

Arg Ala Ser Gln Gly Ile Ser Ser Asp Leu Ala
1               5                   10

<210> SEQ ID NO 147
<211> LENGTH: 7
<212> TYPE: PRT
<213> ORGANISM: Homo sapiens

<400> SEQUENCE: 147

Asp Ala Ser Ser Leu Glu Ser
1               5

<210> SEQ ID NO 148
<211> LENGTH: 9
<212> TYPE: PRT
<213> ORGANISM: Homo sapiens

<400> SEQUENCE: 148

Gln Gln Phe Asn Ser Tyr Pro Phe Thr
1               5

<210> SEQ ID NO 149
<211> LENGTH: 29
<212> TYPE: DNA
<213> ORGANISM: Artificial
<220> FEATURE:
<223> OTHER INFORMATION: primer CD123-Fw21

<400> SEQUENCE: 149
cgtggaaccc gcagtgaaca atagctatt                                    29

<210> SEQ ID NO 150
<211> LENGTH: 30
<212> TYPE: DNA
<213> ORGANISM: Artificial
<220> FEATURE:
<223> OTHER INFORMATION: primer CD123-Re21

<400> SEQUENCE: 150
actctgttct ttttaacaca ctcgatatcg                                   30

<210> SEQ ID NO 151
<211> LENGTH: 29
<212> TYPE: DNA
<213> ORGANISM: Artificial
<220> FEATURE:
<223> OTHER INFORMATION: primer CD123-Fw22

<400> SEQUENCE: 151
ctttatccaa ataacagtgg gaagccttg                                         29

<210> SEQ ID NO 152
<211> LENGTH: 31
<212> TYPE: DNA
<213> ORGANISM: Artificial
<220> FEATURE:
<223> OTHER INFORMATION: primer CD123-Re22

<400> SEQUENCE: 152
cagtttctgt tggaatggtg ggttggccac t                                      31

<210> SEQ ID NO 153
<211> LENGTH: 34
<212> TYPE: DNA
<213> ORGANISM: Artificial
<220> FEATURE:
<223> OTHER INFORMATION: primer CD123-Fw23

<400> SEQUENCE: 153
agggagggta ccggtgcgga aatctgacc tgct                                    34

<210> SEQ ID NO 154
<211> LENGTH: 32
<212> TYPE: DNA
<213> ORGANISM: Artificial
<220> FEATURE:
<223> OTHER INFORMATION: primer CD123-Re23

<400> SEQUENCE: 154
tcctgaattt ggatagaaga ggatccacgt gg                                     32

<210> SEQ ID NO 155
<211> LENGTH: 29
<212> TYPE: DNA
<213> ORGANISM: Artificial
<220> FEATURE:
<223> OTHER INFORMATION: primer CD123-Fw24

<400> SEQUENCE: 155
ggtccgacgg cccccgcgga cgtccagta                                         29

<210> SEQ ID NO 156
<211> LENGTH: 32
<212> TYPE: DNA
<213> ORGANISM: Artificial
<220> FEATURE:
<223> OTHER INFORMATION: primer CD123-Re24

<400> SEQUENCE: 156
cctcgcccag gtacagctca agaaatccac gt                                     32

<210> SEQ ID NO 157
<211> LENGTH: 30
<212> TYPE: DNA
<213> ORGANISM: Artificial
<220> FEATURE:
<223> OTHER INFORMATION: primer CD123-Fw25

<400> SEQUENCE: 157
acggaaccag cgcagccttc ggtatcccct                                        30

<210> SEQ ID NO 158
<211> LENGTH: 28
<212> TYPE: DNA
<213> ORGANISM: Artificial
<220> FEATURE:

-continued

```
<223> OTHER INFORMATION: primer CD123-Re25

<400> SEQUENCE: 158
taaccagaaa gtgggaactt tgagaacc                                28

<210> SEQ ID NO 159
<211> LENGTH: 28
<212> TYPE: DNA
<213> ORGANISM: Artificial
<220> FEATURE:
<223> OTHER INFORMATION: primer CD123-Fw26

<400> SEQUENCE: 159
tctttgattc atttgtcgtc ttttcaca                                28

<210> SEQ ID NO 160
<211> LENGTH: 29
<212> TYPE: DNA
<213> ORGANISM: Artificial
<220> FEATURE:
<223> OTHER INFORMATION: primer CD123-Re26

<400> SEQUENCE: 160
attggatgcc gaaggctgcg ctcctgccc                               29
```